United States Patent
Adema et al.

(10) Patent No.: US 6,479,638 B1
(45) Date of Patent: Nov. 12, 2002

(54) ANTIBODIES THAT SPECIFICALLY BIND DNAX LEUKOCYTE ASSOCIATED IMMUNOGLOBULIN-LIKE RECERPTOR

(75) Inventors: Gosse Jan Adema, Groesbeek; Linde Meyaard, Amsterdam, both of (NL); Daniel M. Gorman, Newark, CA (US); Terrill K. McClanahan, Sunnyvale, CA (US); Sandra M. Zurawski, San Juan Bautista, CA (US); Gerard Zurawski, San Juan Bautista, CA (US); Lewis L. Lanier, Los Altos, CA (US); Joseph H. Phillips, Jr., Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/546,049

(22) Filed: Apr. 10, 2000

Related U.S. Application Data

(62) Division of application No. 08/985,950, filed on Dec. 5, 1997, now Pat. No. 6,140,076.
(60) Provisional application No. 60/032,252, filed on Dec. 6, 1996, provisional application No. 60/033,181, filed on Dec. 16, 1996, and provisional application No. 60/041,279, filed on Mar. 21, 1997.

(51) Int. Cl.⁷ .......................... C07K 16/00; C07K 2/00; C07K 14/00
(52) U.S. Cl. ..................... 530/387.1; 530/300; 530/350; 530/387.9; 530/389.1; 530/391.1; 530/391.3
(58) Field of Search ................................ 530/300, 350, 530/387.1, 387.9, 388.1, 389.1, 391.1, 391.3

(56) References Cited

U.S. PATENT DOCUMENTS 5,314,992 A 5/1994 Guyre et al. ................. 530/350

FOREIGN PATENT DOCUMENTS

| JP | 04187084 | 7/1992 |
| WO | WO 95/29236 | 11/1995 |
| WO | WO 96/34880 | 11/1996 |

OTHER PUBLICATIONS

Mariana C. Castells, et al., *J. Biological Chemistry*, 269(11):8393–8401, 1994. "Cloning of the gp49B Gene of the Immunoglobulin Superfamily and Demonstration That One of Its Two Products Is an Early–expresed Mast Cell Surface Protein Originally Described as gp49*".

Marco Colonna and Jacqueline Samaridis, *SCIENCE*, 268:405–408, Apr. 21, 1998. "Cloning of Immunoglobulin–Superfamily Members Associated with HLA–C and HLA–B Recognition by Human Natural Killer Cells".

M. Colonna and J. Samaridis, *GenBank*, Entrez Browser Protein Query, Accession No. 1171729, Database source: *Swiss–Prot*, Accession No. P43630, Nov. 1, 1995. "Cloning of Immunoglobulin–Superfamily Members Associated with HLA–C and HLA–B Recognition by Human Natural Killer Cells".

M. Colonna, et al., *Transplantation Proceedings*, 28(6):3035, Dec. 1996. "Human Killer Inhibitory Receptors: Specificity for HLA–Class 1 Molecules and Mechanisms of Signal Transduction".

L. Hillier, et al., *Gen Bank*, Accession No. H26010, Jul. 10, 1995. "The WashU–Merck EST Project".

David G. Jackson, et al., *Eur. J. Immunol.*, 22(5):1157–1163, 1992. "Molecular cloning of a novel member of the immunoglobulin gene superfamily homologous to the polymeric immunoglobulin receptor".

Vladimír Korínek, et al., *Immunogenetics*, 33(2):108–112, Feb. 1, 1991. "The human leukocyte antigen CD48 (MEM–102) is closely related to the activation marker Blast–1".

Eric O. Long, et al., *Immunology Today*, 17(2):100, Feb. 1996. "Inhibitory MHC class 1 receptors and T cells: a standard nomenclature".

Charles R. Maliszewski, et al., *J. Exp. Med.*, 172:1665–1672, Dec. 1990. "Expression Cloning of a Human Fc Receptor for IgA".

Linde Meyaard, et al., *Immunity*, 7:283–290, Aug. 1997. "LAIR–1, a Novel Inhibitory Receptor Expressed on Human Mononuclear Leukocytes".

Li Shen, et al., *J. Immunology*, 152:4080–4086, 1994. "Lipopolysaccharide and Cytokine Augmentation of Human Monocyte IgA Receptor Expression and Function".

Y. Sibille, et al., *Eur. Respir. J.*, 7:1111–1119, 1994. "Fc alpha–receptor expression on the myelomonocytic cell line THP–1: comparison with human alveolar macrophages".

J. Samaridis and M. Colonna, *GenBank*, Entrez Browser Nucleotide Query, Accession No. U82279, Mar. 27, 1997. "Cloning of novel immunoglobulin–superfamily receptors expressed on human myeloid and lymphoid cells. Structural evidence for new stimulatory and inhibitory pathways".

Robert Strausberg, *GenBank*, Accession No. AA572674, Sep. 12, 1997. "National Cancer Institute, Cancer Genome Anatomy Project (CGAP), Tumor Gene Index".

WashU–Merck no. yw77c11.s1, *GenBank*, Accession No. N26404, Dec. 29, 1995.

Gaiping Zhang, et al., *Journal of Immunology.*, 155:1534–1541, 1995. "Identification of a Novel Class of Mammalian Fcγ Receptor".

*Primary Examiner*—Elizabeth Kemmerer
*Assistant Examiner*—Bridget E. Bunner
(74) *Attorney, Agent, or Firm*—Edwin P. Ching; Tom Brody; Sheela Mohan-Peterson

(57) ABSTRACT

Nucleic acids encoding various monocyte cell proteins from a primate, reagents related thereto, including specific antibodies, and purified proteins are described. Methods of using reagents relating to nucleic acids encoding monocyte cell proteins, and diagnostic kits, are also provided.

5 Claims, No Drawings

ANTIBODIES THAT SPECIFICALLY BIND DNAX LEUKOCYTE ASSOCIATED IMMUNOGLOBULIN-LIKE RECEPTOR

This filing is a divisional of U.S. Ser. No. 08/985,950, filed Dec. 5, 1997, now U.S. Pat. No. 6,140,076, which is a conversion of, and claims benefit of and priority to, provisional U.S. Patent Applications U.S. Ser. No. 60/032,252, filed Dec. 6, 1996; U.S. Ser. No. 60/033,181, filed Dec. 16, 1996; and U.S. Ser. No. 60/041,279, filed Mar. 21, 1997, each of which is incorporated herein by reference.

FIELD OF THE INVENTION

The present invention contemplates compositions related to genes found in monocyte cells, cells which function in the immune system. These genes function in controlling development, differentiation, and/or physiology of the mammalian immune system. In particular, the application provides nucleic acids, proteins, antibodies, and methods of using them.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology,* Little, Brown and Co., Boston, Mass.; and Paul (ed.) (1993) *Fundamental Immunology* (3d ed.) Raven Press, N.Y.

Monocytes are phagocytic cells that belong to the mononuclear phagocyte system and reside in the circulation. See Roitt (ed) *Encyclopedia of Immunology* Academic Press, San Diego. These cells originate in the bone marrow and remain only a short time in the marrow compartment once they differentiate. They then enter the circulation and can remain there for a relatively long period of time, e.g., a few days. The monocytes can enter the tissues and body cavities by the process designated diapedesis, where they differentiate into macrophages and possibly into dendritic cells. In an inflammatory response, the number of monocytes in the circulation may double, and many of the increased number of monocytes diapedese to the site of inflammation.

Antigen presentation refers to the cellular events in which a proteinaceous antigen is taken up, processed by antigen presenting cells (APC), and then recognized to initiate an immune response. The most active antigen presenting cells have been characterized as the macrophages, which are direct developmental products from monocytes; dendritic cells; and certain B cells.

Macrophages are found in most tissues and are highly active in internalization of a wide variety of protein antigens and microorganisms. They have a highly developed endocytic activity, and secrete many products important in the initiation of an immune response. For this reason, it is believed that many genes expressed by monocytes or induced by monocyte activation are likely to be important in antigen uptake, processing, presentation, or regulation of the resulting immune response.

However, monocytes are poorly characterized, both in terms of proteins they express, and many of their functions and mechanisms of action, including their activated states. In particular, the processes and mechanisms related to the initiation of an immune response, including antigen processing and presentation, remain unclear. The absence of knowledge about the structural, biological, and physiological properties of these cells limits their understanding. Thus, medical conditions where regulation, development, or physiology of antigen presenting cells is unusual remain unmanageable.

SUMMARY OF THE INVENTION

The present invention is based, in part, upon the discovery of various genes isolated from activated monocytes. These molecules have been designated FDF03 (a type I transmembrane protein with Ig-like extracellular portion); YE01 (an Fc gamma/alpha-like receptor); and KTE03 class (cell surface receptors exhibiting Ig-like domains), represented by YYB01, YYB04 related, KLM63, KLM66, and KLM67 embodiments.

The invention provides various compositions of matter selected from: a substantially pure or recombinant FDF03 protein or peptide exhibiting at least about 85% sequence identity over a length of at least about 12 amino acids to mature SEQ ID NO: 2 or 4; a natural sequence FDF03 of SEQ ID NO: 2 or 4; a fusion protein comprising FDF03 sequence; a substantially pure or recombinant YE01 protein or peptide exhibiting at least about 85% sequence identity over a length of at least about 12 amino acids to mature SEQ ID NO: 6, 8, or 10; a natural sequence YE01 of SEQ ID NO: 6, 8, or 10; a fusion protein comprising YE01 sequence; a substantially pure or recombinant KTE03 protein or peptide exhibiting at least about 85% sequence identity over a length of at least about 12 amino acids to SEQ ID NO: 12, 14, 16, 18, 20, or 22; a natural sequence KTE03 of SEQ ID NO: 12, 14, 16, 18, 20, or 22; or a fusion protein comprising KTE03 sequence. Preferably, the substantially pure or isolated protein comprises a segment exhibiting sequence identity to a corresponding portion of a FDF03, YE01, or KTE03, wherein: the homology is at least about 90% identity and the portion is at least about 9 amino acids; the homology is at least about 80% identity and the portion is at least about 17 amino acids; or the homology is at least about 70% identity and the portion is at least about amino acids. In other forms, the invention provides such composition of matter, wherein the: FDF03 comprises a mature sequence of Table 1; YE01 comprises a mature sequence of Table 2; KTE03 comprises a mature sequence of Table 3; or the protein or peptide: is from a warm blooded animal selected from a mammal, including a primate or rodent; comprises at least one polypeptide segment of SEQ ID NO: 2, 4, 6, 8, 10, 12, 14, 16, 18, 20, or 22; exhibits a plurality of portions exhibiting the identity; is a natural allelic variant of FDF03, YE01, or KTE03; has a length at least about 30 amino acids; exhibits at least two non-overlapping epitopes which are specific for a mammalian FDF03, YE01, or KTE03; exhibits a sequence identity at least about 90% over a length of at least about 20 amino acids to a rodent FDF03, YE01, or KTE03; exhibits at least two non-overlapping epitopes which are specific for a primate FDF03, YE01, or KTE03; exhibits a sequence identity at least about 90% over a length of at least about 20 amino acids to a primate FDF03, YE01, or KTE03; is glycosylated; has a molecular weight of at least 7 kD with natural glycosylation; is a synthetic polypeptide; is attached to a solid substrate; is conjugated to another chemical moiety; is a 5-fold or less substitution from natural sequence; or is a deletion or insertion variant from a natural sequence.

Other compositions include those comprising: a sterile FDF03 protein or peptide;the FDF03 protein or peptide and a carrier, wherein the carrier is: an aqueous compound, including water, saline, and/or buffer; and/or formulated for oral, rectal, nasal, topical, or parenteral administration; a sterile YE01 protein or peptide; the YE01 protein or peptide and a carrier, wherein the carrier is: an aqueous compound, including water, saline, and/or buffer; and/or formulated for oral, rectal, nasal, topical, or parenteral administration; a sterile KTE03 protein or peptide; or the KTE03 protein or peptide and a carrier, wherein the carrier is: an aqueous compound, including water, saline, and/or buffer; and/or formulated for oral, rectal, nasal, topical, or parenteral administration.

In fusion protein embodiments, the invention provides those which comprise: mature protein sequence of Table 1, 2, or 3; a detection or purification tag, including a FLAG, His6, or Ig sequence; or sequence of another cell surface protein.

Various kits include those comprising a protein or polypeptide, and: a compartment comprising the protein or polypeptide; and/or instructions for use or disposal of reagents in the kit.

Antibodies and binding compounds include those comprising an antigen binding portion from an antibody, which specifically binds to a natural FDF03, YE01, or KTE03 protein, wherein: the protein is a primate protein; the binding compound is an Fv, Fab, or Fab2 fragment; the binding compound is conjugated to another chemical moiety; or the antibody: is raised against a peptide sequence of a mature polypeptide of Table 1, 2, or 3; is raised against a mature FDF03, YE01, or KTE03; is raised to a purified FDF03, YE01, or KTE03; is immunoselected; is a polyclonal antibody; binds to a denatured FDF03, YE01, or KTE03; exhibits a Kd to antigen of at least 30 $\mu$M; is attached to a solid substrate, including a bead or plastic membrane; is in a sterile composition; or is detectably labeled, including a radioactive or fluorescent label. A kit comprising the binding compound is provided including, e.g., the binding compound and: a compartment comprising the binding compound; and/or instructions for use or disposal of reagents in the kit. Preferably, the kit is capable of making a qualitative or quantitative analysis.

Various other compositions include those comprising: a sterile binding compound; or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding a protein or peptide or fusion protein as described, wherein: the protein is from a mammal, including a primate; or the nucleic acid: encodes an antigenic peptide sequence of Table 1, 2, or 3; encodes a plurality of antigenic peptide sequences of Table 1, 2, or 3; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding the protein; or is a PCR primer, PCR product, or mutagenesis primer.

Various cells are provided, including those comprising a described recombinant nucleic acid. Preferably, the cell is: a prokaryotic cell; a eukaryotic cell; a bacterial cell; a yeast cell; an insect cell; a mammalian cell; a mouse cell; a primate cell; or a human cell. Kits with such nucleic acids include those with the nucleic acid and: a compartment comprising the nucleic acid; a compartment further comprising a FDF03, YE01, or KTE03 protein or polypeptide; and/or instructions for use or disposal of reagents in the kit. Preferably, the kit is capable of making a qualitative or quantitative analysis.

Other nucleic acids include those which: hybridize under wash conditions of 30° C. and less than 2M salt to the coding portions of SEQ ID NO: 1 or 3; hybridize under wash conditions of 30° C. and less than 2 M salt to the coding portions of SEQ ID NO: 5, 7, or 9; hybridize under wash conditions of 30° C. and less than 2M salt to the coding portions of SEQ ID NO: 11, 13, 15, 17, 19, or 21; exhibit at least about 85% identity over a stretch of at least about 30 nucleotides to a primate FDF03; exhibit at least about 85% identity over a stretch of at least about 30 nucleotides to a primate YE01; or exhibit at least about 85% identity over a stretch of at least about 30 nucleotides to a primate KTE03. In preferred embodiments, the wash conditions are at 45° C. and/or 500 mM salt; or at 55° C. and/or 150 mM salt; or the identity is at least 90% and/or the stretch is at least 55 nucleotides; or the identity is at least 95% and/or the stretch is at least 75 nucleotides.

The invention further provides a method of modulating physiology or development of a cell or tissue culture cell comprising contacting the cell with an agonist or antagonist of a FDF03, YE01, or KTE03. In preferred embodiments, the cell is a leukocyte, and the antagonist is to YE01 and is a monoclonal antibody which binds to DLAIR-1.

DETAILED DESCRIPTION

Outline

I. General
II. Definitions
III. Nucleic Acids
IV. Making Proteins
V. Antibodies
VI. Purified Proteins
VII. Physical Variants
VIII. Binding Agent:Monocyte Protein Complexes
IX. Uses
X. Kits
XI. Binding Partner Isolation I. General The present invention provides DNA sequences encoding mammalian proteins expressed on monocytes. For a review of monocytes and their functions, see, e.g., Gallin, et al. (eds. 1988) *Inflammation: Basic Principles and Clinical Correlates* Raven Press, NY; van Furth (ed. 1985) *Mononuclear Phaaocvtes: Characteristics, Physiology and Function* Martinus Nijhoff, Dordrecht, Netherlands.

Specific human embodiments of these proteins are provided below. The descriptions below are directed, for exemplary purposes, to human monocyte genes, but are likewise applicable to structurally, e.g., sequence, related embodiments from other sources or mammalian species, including polymorphic or individual variants. These will include, e.g., proteins which exhibit a relatively few changes in sequence, e.g., less than about 5%, and number, e.g., less than 20 residue substitutions, typically less than 15, preferably less than 10, and more preferably less than 5 substitutions. These will also include versions which are truncated from full length, as described, and fusion proteins containing substantial segments of these sequences.

II. Definitions

The term "binding composition" refers to molecules that bind with specificity to a these monocyte proteins, e.g., in an antibody-antigen interaction, or compounds, e.g., proteins, which specifically associate with the respective protein. Typically, the association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protein with structural modifications, or may be a wholly unrelated molecule, e.g., which has a molecular shape which interacts with the appropriate interacting determinants. The variants may serve as agonists or antagonists of the protein, see, e.g., Goodman, et al. (eds.) (1990) *Goodman & Gilman's: The Pharmacological Bases of Therapeutics* (8th ed.) Pergamon Press, Tarrytown, N.Y.

The term "binding agent:monocyte protein complex", as used herein, refers to a complex of a binding agent and the monocyte protein. Specific binding of the binding agent means that the binding agent has a specific binding site that recognizes a site on the respective monocyte protein. For example, antibodies raised to the monocyte protein and recognizing an epitope on the monocyte protein are capable of forming a binding agent:monocyte protein complex by specific binding. Typically, the formation of a binding agent:monocyte protein complex allows the measurement of monocyte protein in a mixture of other proteins and biologics. The term "antibody:monocyte protein complex" refers to a binding agent:monocyte protein complex in which the binding agent is an antibody. The antibody may be monoclonal, polyclonal or even an antigen binding fragment of an antibody.

"Homologous" nucleic acid sequences, when compared, exhibit significant similarity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. An isolated nucleic acid will generally be a homogeneous composition of molecules, but will, in some embodiments, contain minor heterogeneity. This heterogeneity is typically found at the polymer ends or portions not critical to a desired biological function or activity.

As used herein, the term "monocyte protein" shall encompass, when used in a protein context, a protein having amino acid sequences as shown in SEQ ID NO: 2 or 4; 6, 8, or 10; or 12, 14, 16, 18, 20, or 22, or a significant fragment of such a protein. It refers to a polypeptide which interacts with the respective monocyte protein specific binding components. These binding components, e.g., antibodies, typically bind to the monocyte protein with high affinity, e.g., at least about 100 nM, usually better than about 30 nM, preferably better than about 10 nM, and more preferably at better than about 3 nM.

The term "polypeptide" or "protein" as used herein includes a significant fragment or segment of said monocyte protein, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Fragment or size limitations applicable for comparison to one group, e.g., to the FDF03, do not necessarily imply similar size limitations on fragments for the others.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1–3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the protein.

"Substantially pure" typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1 or 3; 5, 7, or 9; or 11, 13, 15, 17, 19, or 21. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa (1984) Nucl. Acids Res. 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

Counterpart monocyte proteins from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human monocyte protein immunogen with the amino acid sequence depicted in SEQ ID NO: 2 can be selected to obtain antibodies specifically immunoreactive with that monocyte protein and not with other proteins. These antibodies recognize proteins highly similar to the homologous human monocyte protein.

III. Nucleic Acids

These monocyte genes are specifically expressed on dendritic cells. The preferred embodiments, as disclosed, will be useful in standard procedures to isolate genes from other species, e.g., warm blooded animals, such as birds and mammals. Cross hybridization will allow isolation of related proteins from individuals, strains, or species. A number of different approaches are available successfully to isolate a suitable nucleic acid clone based upon the information provided herein. Southern blot hybridization studies should identify homologous genes in other species under appropriate hybridization conditions.

Purified protein or defined peptides are useful for generating antibodies by standard methods, as described below. Synthetic peptides or purified protein can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference. Alternatively, a CD protein binding composition can be useful as a specific binding reagent, and advantage can be taken of its specificity of binding, for, e.g., purification of a monocyte protein.

The specific binding composition can be used for screening an expression library made from a cell line which expresses the respective monocyte protein. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

TABLE 1

Sequence encoding a human FDF03 protein, containing Ig domains. The putative coding region runs from about 154 to 1062. See SEQ ID NO: 1 and 2. This 1249 bp clone was isolated from a monocyte cell library. A putative (hydrophobic) signal sequence runs from -19 to about -1; a putative transmembrane (hydrophobic) segment runs from about 178 to 199. The extracellular region is probably about 170 amino acids, with a potential Ig-like domain structure; the intracellular region is about 80 residues. Sequence analysis indicates similarity to GenBank clones H26010 and R50327 from humans.

GTTTGGGGAA GGCTCCTGGC CCCCACAGCC CTCTTCGGAG CCTGAGCCCG GCTCTCCTCA    60

CTCACCTCAA CCCCCAGGCG GCCCCTCCAC AGGGCCCCTC TCCTGCCTGG ACGGCTCTGC   120

TABLE 1-continued

```
TGGTCTCCCC GTCCCCTGGA AGAACAAG GCC ATG GGT CGG CCC CTG CTG CTG          174
                                    Met Gly Arg Pro Leu Leu Leu
                                    -19              -15

CCC CTA CTG CCC CTG CTG CTG CCG CCA GCA TTT CTG CAG CCT AGT GGC          222
Pro Leu Leu Pro Leu Leu Leu Pro Ala Phe Leu Gln Pro Ser Gly
        -10              -5                   1

TCC ACA GGA TCT GGT CCA AGC TAC CTT TAT GGG GTC ACT CAA CCA AAA          270
Ser Thr Gly Ser Gly Pro Ser Tyr Leu Tyr Gly Val Thr Gln Pro Lys
 5               10                  15                  20

CAC CTC TCA GCC TCC ATG GGT GGC TCT GTG GAA ATC CCC TTC TCC TTC          318
His Leu Ser Ala Ser Met Gly Gly Ser Val Glu Ile Pro Phe Ser Phe
                 25                  30                  35

TAT TAC CCC TGG GAG TTA GCC ACA GCT CCC GAC GTG AGA ATA TCC TGG          366
Tyr Tyr Pro Trp Glu Leu Ala Thr Ala Pro Asp Val Arg Ile Ser Trp
             40                  45                  50

AGA CGG GGC CAC TTC CAC GGG CAG TCC TTC TAC AGC ACA AGG CCG CCT          414
Arg Arg Gly His Phe His Gly Gln Ser Phe Tyr Ser Thr Arg Pro Pro
             55                  60                  65

TCC ATT CAC AAG GAT TAT GTG AAC CGG CTC TTT CTG AAC TGG ACA GAG          462
Ser Ile His Lys Asp Tyr Val Asn Arg Leu Phe Leu Asn Trp Thr Glu
         70                  75                  80

GGT CAG AAG AGC GGC TTC CTC AGG ATC TCC AAC CTG CAG AAG CAG GAC          510
Gly Gln Lys Ser Gly Phe Leu Arg Ile Ser Asn Leu Gln Lys Gln Asp
 85                  90                  95                 100

CAG TCT GTG TAT TTC TGC CGA GTT GAG CTG GAC ACA CGG AGC TCA GGG          558
Gln Ser Val Tyr Phe Cys Arg Val Glu Leu Asp Thr Arg Ser Ser Gly
                105                 110                 115

AGG CAG CAG TGG CAG TCC ATC GAG GCC ACC AAA CTC TCC ATC ACC CAG          606
Arg Gln Gln Trp Gln Ser Ile Glu Gly Thr Lys Leu Ser Ile Thr Gln
            120                 125                 130

GCT GTC ACG ACC ACC ACC CAG AGG CCC AGC AGC ATG ACT ACC ACC TGG          654
Ala Val Thr Thr Thr Thr Gln Arg Pro Ser Ser Met Thr Thr Thr Trp
            135                 140                 145

AGG CTC AGT AGC ACA ACC ACC ACA ACC GGC CTC AGG GTC ACA CAG GGC          702
Arg Leu Ser Ser Thr Thr Thr Thr Gly Leu Arg Val Thr Gln Gly
        150                 155                 160

AAA CGA CGC TCA GAC TCT TGG CAC ATA AGT CTG GAG ACT GCT GTG GGG          750
Lys Arg Arg Ser Asp Ser Trp His Ile Ser Leu Glu Thr Ala Val Gly
165                 170                 175                 180

GTG GCA GTG GCT GTC ACT GTG CTC GGA ATC ATG ATT TTG GGA CTG ATC          798
Val Ala Val Ala Val Thr Val Leu Gly Ile Met Ile Leu Gly Leu Ile
                185                 190                 195

TGC CTC CTC AGG TGG AGG AGA AGG AAA GGT CAG CAG CGG ACT AAA GCC          846
Cys Leu Leu Arg Trp Arg Arg Arg Lys Gly Gln Gln Arg Thr Lys Ala
            200                 205                 210

ACA ACC CCA GCC AGG GAA CCC TTC CAA AAC ACA GAG GAG CCA TAT GAG          894
Thr Thr Pro Ala Arg Glu Pro Phe Gln Asn Thr Glu Glu Pro Tyr Glu
            215                 220                 225

AAT ATC AGG AAT GAA GGA CAA AAT ACA GAT CCC AAG CTA AAT CCC AAG          942
Asn Ile Arg Asn Glu Gly Gln Asn Thr Asp Pro Lys Leu Asn Pro Lys
        230                 235                 240

GAT GAC GGC ATC GTA TAT GCT TCC CTT GCC CTC TCC AGC TCC ACC TCA          990
Asp Asp Gly Ile Val Tyr Ala Ser Leu Ala Leu Ser Ser Ser Thr Ser
245                 250                 255                 260

CCC AGA GCA CCT CCC AGC CAC CGT CCC CTC AAG AGC CCC CAG AAC GAG         1038
Pro Arg Ala Pro Pro Ser His Arg Pro Leu Lys Ser Pro Gln Asn Glu
                265                 270                 275

ACC CTG TAC TCT GTC TTA AAG GCC TAACCAATGG ACAGCCCTCT CAAGACTGAA        1092
Thr Leu Tyr Ser Val Leu Lys Ala
```

TABLE 1-continued

```
                280
TGGTGAGGCC AGGTACAGTG GCGCACACCT GTAATCCCAG CTACTCTGAA GCCTGAGGCA  1152

GAATCAAGTG AGCCCAGGAG TTCAGGGCCA GCTTTGATAA TGGAGCGAGA TGCCATCTCT  1212

AGTTAAAAAT ATATATTAAC AATAAAGTAA CAAATTT                           1249
```

A mouse counterpart partial sequence is (SEQ ID NO: 3 and 4):

```
CCCCAGTGTC CCTAGACAGA GCATCCTTGC CTTCCTGATG GCTTTGCTGA TCTCGCTTCC   60

CTGGAGGGAC TCCAGCC ATG GCT CAG GTC CTG CTT CTG CTC TCA TCA GGC    110
                   Met Ala Gln Val Leu Leu Leu Leu Ser Ser Gly
                    1               5                       10

TGT CTG CAT GCT GGA AAT TCA GAA AGA TAC AAC AGA AAA AAT GGC TTT   158
Cys Leu His Ala Gly Asn Ser Glu Arg Tyr Asn Arg Lys Asn Gly Phe
            15                  20                  25

GGG GTC AAC CAA CCT GAA CGC TGC TCT GGA GTC CAG GGT GGC TCC ATC   206
Gly Val Asn Gln Pro Glu Arg Cys Ser Gly Val Gln Gly Gly Ser Ile
            30                  35                  40

GAC ATC CCC TTC TCC TTC TAT TTC CCC TGG AAG TTG GCC AAG GAT CCA   254
Asp Ile Pro Phe Ser Phe Tyr Phe Pro Trp Lys Leu Ala Lys Asp Pro
        45                  50                  55

CAG ATG AGC ATA GCC TGG AAA TGG AAC GAT TTC CAT GGG GAA GTC ATC   302
Gln Met Ser Ile Ala Trp Lys Trp Lys Asp Phe His Gly Glu Val Ile
 60                  65                  70                  75

TAC AAC TCC TCC CTG CCT TTC ATA CAT GAG CAC TTC AAG GGC CGG CTC   350
Tyr Asn Ser Ser Leu Pro Phe Ile His Glu His Phe Lys Gly Arg Leu
                 80                  85                  90

ATC CTG AAC TGG ACA CAG GGT CAG AC                                376
Ile Leu Asn Trp Thr Gln Gly Gln
                 95
``` partial human mouse alignment:

```
hu MGRPLLLPLLPLLLPPAFLQPSGSTGSGPSYLYGVTQPKHLSASMGGSVEIPFSFYYPWE
mo MAQVLLLLSSGCLHAGNSERYNRKNG------FGVNQPERCSGVQGGSIDIPFSFYFPWK hu LATAPDVRISWRRGHFHGQSFYSTRPPSIHKDYVNRLFLNWTEGQKSGFLRISNLQK...
mo LAKDPQMSIAWKWKDFHGEVIYNSSLPFIHEHFKGRLILNWTQGQ...
```

TABLE 2

Sequence encoding a protein related to Ig family members, designated YE01, isolated from an activated monocyte cell library. See SEQ ID NO: 5 and 6. Signal sequence is indicated. Nucleotide 1247 may be C or T. Sequence analysis suggests YE01 is a member of the Ig superfamily of receptors, and is closely related to the CD8 family, which contain a V1J-type fold, particularly the Fc receptors alpha and/or gamma. Because it contains an ITAM-like motif, the protein may well be a monocyte version of the KIR proteins, the killer Inhibitory Receptors, which send a negative signal to inhibit killer cell function. This protein may share similar function in inhibiting monocyte effector function, e.g., antigen presentation or subsequent response initiation. A mouse counterpart is probably encoded in the EST W55567.

```
ACCGGTCCGG AATTCCCGGG TCGACCCACG CGTCCGGGAA GCCCCATAGG CAGGAGGCCC   60

CCGGGCAGCA CATCCTGTCT GCTTGTGTCT GCTGCAGAGT TCTGTCCTTG CATTGGTGCG  120

CCTCAGGCCA GGCTGCACTG CTGGGACCTG GCCC ATG TCT CCC CAC CCC ACC     172
                                       Met Ser Pro His Pro Thr
                                       -21 -20

GCC CTC CTG GGC CTA GTG CTC TGC CTG GCC CAG ACC ATC CAC ACG CAG   220
Ala Leu Leu Gly Leu Val Leu Cys Leu Ala Gln Thr Ile His Thr Gln
-15                 -10                  -5                   1
```

TABLE 2-continued

```
GAG GAA GAT CTG CCC AGA CCC TCC ATC TCG GCT GAG CCA GGC ACC GTG      268
Glu Glu Asp Leu Pro Arg Pro Ser Ile Ser Ala Glu Pro Gly Thr Val
          5                   10                  15

ATC CCC CTG GGG AGC CAT GTG ACT TTC GTG TGC CGG GGC CCG GTT GGG      316
Ile Pro Leu Gly Ser His Val Thr Phe Val Cys Arg Gly Pro Val Gly
         20                  25                  30

GTT CAA ACA TTC CGC CTC GAG AGG GAG AGT AGA TCC ACA TAC AAT CAT      364
Val Gln Thr Phe Arg Leu Glu Arg Glu Ser Arg Ser Thr Tyr Asn Asp
         35                  40                  45

ACT GAA GAT GTG TCT CAA GCT AGT CCA TCT GAG TCA GAG GCC AGA TTC      412
Thr Glu Asp Val Ser Gln Ala Ser Pro Ser Glu Ser Glu Ala Arg Phe
50                  55                  60                  65

CGC ATT GAC TCA GTA AGT GAA GGA AAT GCC GGG CCT TAT CGC TGC ATC      460
Arg Ile Asp Ser Val Ser Glu Cly Asn Ala Gly Pro Tyr Arg Cys Ile
                    70                  75                  80

TAT TAT AAG CCC CCT AAA TGG TCT GAG CAG AGT GAC TAC CTG GAG CTG      508
Tyr Tyr Lys Pro Pro Lys Trp Ser Glu Gln Ser Asp Tyr Leu Glu Leu
                85                  90                  95

CTG GTG AAA GAA ACC TCT GGA GGC CCG GAC TCC CCG GAC ACA GAG CCC      556
Leu Val Lys Glu Thr Ser Gly Gly Pro Asp Ser Pro Asp Thr Glu Pro
            100                 105                 110

GGC TCC TCA GCT GGA CCC ACG CAG AGG CCG TCG GAC AAC AGT CAC AAT      604
Gly Ser Ser Ala Gly Pro Thr Gln Arg Pro Ser Asp Asn Ser His Asn
        115                 120                 125

GAG CAT GCA CCT GCT TCC CAA GGC CTG AAA GCT GAG CAT CTG TAT ATT      652
Glu His Ala Pro Ala Ser Gln Gly Leu Lys Ala Glu His Leu Tyr Ile
130                 135                 140                 145

CTC ATC GGG GTC TCA GTG GTC TTC CTC TTC TGT CTC CTC CTC CTG GTC      700
Leu Ile Gly Val Ser Val Val Phe Leu Phe Cys Leu Leu Leu Leu Val
                    150                 155                 160

CTC TTC TGC CTC CAT CGC CAG AAT CAG ATA AAG CAG GGG CCC CCC AGA      748
Leu Phe Cys Leu His Arg Gln Asn Gln Ile Lys Gln Gly Pro Pro Arg
                165                 170                 175

AGC AAG GAC GAG GAG CAG AAG CCA CAG CAG AGG CCT GAC CTG GCT GTT      796
Ser Lys Asp Glu Glu Gln Lys Pro Gln Gln Arg Pro Asp Leu Ala Val
            180                 185                 190

GAT GTT CTA GAG AGG ACA GCA GAC AAG GCC ACA GTC AAT GGA CTT CCT      844
Asp Val Leu Glu Arg Thr Ala Asp Lys Ala Thr Val Asn Gly Leu Pro
        195                 200                 205

GAG AAG GAC AGA GAG ACG GAC ACC TCC GCC CTG GCT GCA GGG AGT TCC      892
Glu Lys Asp Arg Glu Thr Asp Thr Ser Ala Leu Ala Ala Gly Ser Ser
210                 215                 220                 225

CAG GAG GTC ACG TAT GCT CAG CTG GAC CAC TGG GCC CTC ACA CAG AGG      940
Gln Glu Val Thr Tyr Ala Gln Leu Asp His Trp Ala Leu Thr Gln Arg
                    230                 235                 240

ACA GCC CGG GCT GTG TCC CCA CAG TCC ACA AAG CCC ATC GCC GAG TCC      988
Thr Ala Arg Ala Val Ser Pro Gln Ser Thr Lys Pro Met Ala Glu Ser
                245                 250                 255

ATC ACG TAT GCA GCC GTT GCC AGA CAC TGACCCCATA CCCACCTGGC           1035
Ile Thr Tyr Ala Ala Val Ala Arg His
            260                 265

CTCTGCACCT GAGGGTAGAA AGTCACTCTA GGAAAAGCCT GAAGCAGCCA TTTGGAAGGC  1095

TTCCTGTTGG ATTCCTCTTC ATCTAGAAAG CCAGCCAGGC AGCTGTCCTG GAGACAAGAG  1155

CTGGAGACTG GAGGTTTCTA ACCAGCATCC AGAAGGTTCG TTAGCCAGGT GGTCCCTTCT  1215

ACAATCGGAC AGCTCCTTGG ACAGACTGTT TCTCAGTTAT TTCCAAAAAC CCAGCTACAG  1275

TTCC                                                               1279
```

TABLE 2-continued

A similar gene was cloned by expressing cloning using
a monoclonal antibody DX26, which was raised against the immunogen
of human NK cell clone NK681.D5, and selected for inhibiting
killing by NK cell clones of Fc receptor bearing target cells
(SP2/0). SEQ ID NO: 7 and 8.

```
AAAGGCTGCA GAGTTCTCTC CTTGCATTGG TCCGCCTCAG GCCAGGCTGC ACTGCTCGGA    60

CCTGGGCC ATG TCT CCC CAC CCC ACC GCC CTC CTG GGC CTA GTG CTC TGC   110
         Met Ser Pro His Pro Thr Ala Leu Leu Gly Leu Val Leu Cys
         -21 -20              -15                     -10

CTG GCC CAG ACC ATC CAC ACG CAG GAG GAA GAT CTG CCC AGA CCC TCC    158
Leu Ala Gln Thr Ile His Thr Gln Glu Glu Asp Leu Pro Arg Pro Ser
         -5                   1                5

ATC TCG GCT GAG CCA GGC ACC GTG ATC CCC CTG GGG AGC CAT GTG ACT    206
Ile Ser Ala Glu Pro Gly Thr Val Ile Pro Leu Gly Ser His Val Thr
 10              15                  20                      25

TTC GTG TGC CGG GGC CCG GTT GGG GTT CAA ACA TTC CGC CTG GAG AGG    254
Phe Val Cys Arg Gly Pro Val Gly Val Gln Thr Phe Arg Leu Glu Arg
                 30              35                  40

GAG AGT AGA TCC ACA TAC AAT GAT ACT GAA GAT GTG TCT CAA GCT AGT    302
Glu Ser Arg Ser Thr Tyr Asn Asp Thr Glu Asp Val Ser Gln Ala Ser
             45                  50                  55

CCA TCT GAG TCA GAG GCC AGA TTC CGC ATT GAC TCA GTA AGT GAA GGA    350
Pro Ser Glu Ser Glu Ala Arg Phe Arg Ile Asp Ser Val Ser Glu Gly
         60                  65                  70

AAT GCC GGG CCT TAT CGC TCC ATC TAT TAT AAG CCC CCT AAA TGG TCT    398
Asn Ala Gly Pro Tyr Arg Cys Ile Tyr Tyr Lys Pro Pro Lys Trp Ser
     75                  80                  85

GAG CAG AGT GAC TAC CTG GAG CTG CTG GTG AAA GAA ACC TCT GGA GGC    446
Glu Gln Ser Asp Tyr Leu Glu Leu Leu Val Lys Glu Thr Ser Gly Gly
 90                  95                  100                 105

CCG GAC TCC CCG GAC ACA GAG CCC GGC TCC TCA GCT GGA CCC ACG CAG    494
Pro Asp Ser Pro Asp Thr Glu Pro Gly Ser Ser Ala Gly Pro Thr Gln
                 110                 115                 120

AGG CCG TCG GAC AAC AGT CAC AAT GAG CAT GCA CCT GCT TCC CAA GGC    542
Arg Pro Ser Asp Asn Ser His Asn Glu His Ala Pro Ala Ser Gln Gly
             125                 130                 135

CTG AAA GCT GAG CAT CTG TAT ATT CTC ATC GGG GTC TCA GTG GTC TTC    590
Leu Lys Ala Glu His Leu Tyr Ile Leu Ile Gly Val Ser Val Val Phe
         140                 145                 150

CTC TTC TGT CTC CTC CTG GTC CTC TTC TGC CTC CAT CGC CAG AAT    638
Leu Phe Cys Leu Leu Leu Val Leu Phe Cys Leu His Arg Gln Asn
     155                 160                 165

CAG ATA AAG CAG GCG CCC CCC AGA AGC AAG GAC GAG GAG CAG AAG CCA    686
Gln Ile Lys Gln Gly Pro Pro Arg Ser Lys Asp Glu Glu Gln Lys Pro
170             175                 180                     185

CAG CAG AGC CCT GAC CTG GCT GTT GAT GTT CTA GAG ACG ACA GCA GAC    734
Gln Gln Ser Pro Asp Leu Ala Val Asp Val Leu Glu Arg Thr Ala Asp
                 190                 195                 200

AAG GCC ACA GTC AAT GGA CTT CCT GAG AAG GAC AGA GAG ACG GAC ACC    782
Lys Ala Thr Val Asn Cly Leu Pro Glu Lys Asp Arg Glu Thr Asp Thr
                 205                 210                 215

TCG GCC CTG GCT GCA GGG AGT TCC CAG GAC GTG ACG TAT GCT CAG CTG    830
Ser Ala Leu Ala Ala Gly Ser Ser Gln Asp Val Thr Tyr Ala Gln Leu
             220                 225                 230

GAC CAC TGG GCC CTC ACA CAG AGG ACA GCC CGG GCT GTG TCC CCA CAG    878
Asp His Trp Ala Leu Thr Gln Arg Thr Ala Arg Ala Val Ser Pro Gln
         235                 240                 245

TCC ACA AAG CCC ATG GCC GAG TCC ATC ACG TAT GCA GCC GTT GCC ACA    926
Ser Thr Lys Pro Met Ala Glu Ser Ile Thr Tyr Ala Ala Val Ala Arg
 250                 255                 260                 265
```

TABLE 2-continued

```
CAC TGACCCCATA CCCACCTGGC CTCTGCACCT GAGGGTAGAA AGTCACTCTA        979
His

GGAAAAGCCT GAAGCAGCCA TTTGGAAGGC TTCCTGTTGG ATTCCTCTTC ATCTAGAAAG 1039

CCAGCCAGGC AGCTGTCCTG GAGACAAGAG CTGGAGACTG GAGGTTTCTA ACCAGCATCC 1099

AGAAGGTTCG TTAGCCAGGT GGTCCCTTCT ACAATCGAGC AGCTCCTTGG ACAGACTGTT 1159

TCTCAGTTAT TTCCAGAGAC CCAGCTACAG TTCCCTGGCT GTTTCTAGAC ACCCAGCTTT 1219

ATTCACCTGA CTGTTTCCAG AGACCCAGCT AAAGTCACCT GCCTGTTCTA AAGCCCCAGC 1279

TACAGCCAAT CAGCCGATTT CCTCAGCAGT GATGCCACCT CCAAGCTTGT CCTAGGTGTC 1339

TGCTGTGAAC CTCCAGTGAC CCCAGACACT TTGCTCTAAT TATCTGCCCT GCTGACCCTA 1399

AAGACCTTCC TAGAAGTCAA GAGCTAGCCT TGAGACTGTG CTATACACAC ACAGCTGAGA 1459

GCCAAGCCCA GTTCTCTGGG TTGTGCTTTA CTCCACGCAT CAATAAATAA TTTTGAAGGC 1519

CTCACATCTG GCAGCCCCAG GCCTGGTCCT GGGTGCATAG GTCTCTCGGA CCCACTCTCT 1579

GCCTTCACAG TTGTTCAAAG CTGAGTGAGG GAAACAGGAC TTACGAAAAC GTGTCAGCGT 1639

TTTCTTTTTA AAATTTAATT GATCAGGATT GTACGTAAAA AAAAAAAAAA AAAAAAAAAA 1699

AAAAAAAAAA AAAAAAAAAA AAAAAAGG                                   1728
```

Nucleic acid and putative amino acid sequence of soluble DLAIR-2. The signal sequence runs from about Met(-21) to Thr(-1) (SEQ ID NO: 9 and 10).

```
CCACGCGTCC GGGGACCGGG GCC ATG TCT CCA CAC CTC ACT GCT CTC CTG        50
                        Met Ser Pro His Leu Thr Ala Leu Leu
                        -21 -20                  -15

GGC CTA GTG CTC TGC CTG GCC CAG ACC ATC CAC ACG CAG GAG GGG GCC     98
Gly Leu Val Leu Cys Leu Ala Gln Thr Ile His Thr Gln Glu Gly Ala
        -10              -5                   1

CTT CCC AGA CCC TCC ATC TCG GCT GAG CCA GGC ACT GTG ATC TCC CCG    146
Leu Pro Arg Pro Ser Ile Ser Ala Glu Pro Gly Thr Val Ile Ser Pro
    5                10                  15                  20

GGG AGC CAT GTG ACT TTC ATG TGC CGG GGC CCG GTT GGG GTT CAA ACA    194
Gly Ser His Val Thr Phe Met Cys Arg Gly Pro Val Gly Val Gln Thr
              25                  30                  35

TTC CGC CTG GAG AGG GAG GAT AGA GCC AAG TAC AAA GAT AGT TAT AAT    242
Phe Arg Leu Glu Arg Glu Asp Arg Ala Lys Tyr Lys Asp Ser Tyr Asn
            40                  45                  50

GTG TTT CGA CTT GGT CCA TCT GAG TCA GAG GCC AGA TTC CAC ATT GAC    290
Val Phe Arg Leu Gly Pro Ser Glu Ser Glu Ala Arg Phe His Ile Asp
        55                  60                  65

TCA GTA AGT GAA GGA AAT GCC GGG CTT TAT CGC TGC CTC TAT TAT AAG    338
Ser Val Ser Glu Gly Asn Ala Gly Leu Tyr Arg Cys Leu Tyr Tyr Lys
    70                  75                  80

CCC CCT GGA TGG TCT GAG CAC AGT GAC TTC CTG GAG CTG CTG GTG AAA    386
Pro Pro Gly Trp Ser Glu His Ser Asp Phe Leu Glu Leu Leu Val Lys
85                  90                  95                 100

GGG ACT GTG CCA GGC ACT GAA GCC TCC GGA TTT GAT GCA CCA               428
Gly Thr Val Pro Gly Thr Glu Ala Ser Gly Phe Asp Ala Pro
                105                 110

TGAATGAGGA GAAATGGCCT CCCGTCTTGT GAACTTCAAT GGGGAGAAAT AATTAGAATG  488

AGCAATAGAA ATGCACAGAT GCCTATACAT ACATATACAA ATAAAAGAT ACGATTCGCA  548

AAAAAAAAAA AAAAAAGGGC                                             568
```

TABLE 3

Human KTE03 sequences, e.g., alternative splicing, encoding related proteins with homology to several NK KIR surface molecules, and to the Fc receptors gamma and alpha. YYB01 coding sequence appears to run from about 81 to 1397. The message appears to be IL-10 upregulated. See SEQ ID NO: 11 and 12. Because of significant identity of sequence which ends at specific locations, it appears that there may be splice junctions around nucleotide 36, 1264, and 1587. The YYB04 sequence provided below indicates that certain insertions of sequence lead to a frameshift and alternative carboxy terminal sequence. Moreover, certain peculiar differences in sequence suggest either sequencing errors, or a mechanism of variability generated by a mechanism perhaps analogous to hypervariable region combinations.

```
GTCGACCCAC GCGTCCGCCT CTGTCCTGCC AGCACCGAGG GCTCATCCAT CCACAGAGCA    60

GTGCAGTGGG AGGAGACGCC ATG ACC CCC ATC CTC ACG GTC CTG ATC TGT       110
                      Met Thr Pro Ile Leu Thr Val Leu Ile Cys
                       1               5                    10

CTC GGG CTG AGC CTG GAC CCC AGG ACC CAC GTG CAG GCA GGG CCC CTC     158
Leu Gly Leu Ser Leu Asp Pro Arg Thr His Val Gln Ala Gly Pro Leu
                 15                  20                  25

CCC AAG CCC ACC CTC TGG GCT GAG CCA GGC TCT GTG ATC AGG CAA GGG     206
Pro Lys Pro Thr Leu Trp Ala Glu Pro Gly Ser Val Ile Arg Gln Gly
             30                  35                  40

AGT CCT GTG ACC CTC AGG TGT CAG GGG AGC CTG GAG ACG CAG GAG TAC     254
Ser Pro Val Thr Leu Arg Cys Gln Gly Ser Leu Glu Thr Gln Glu Tyr
         45                  50                  55

CAT CTA TAT AGA GAA AAG AAA ACA GCA CTC TGG ATT ACA CGG ATC CCA     302
His Leu Tyr Arg Glu Lys Lys Thr Ala Leu Trp Ile Thr Arg Ile Pro
     60                  65                  70

CAG GAG CTT GTG AAG AAG GGC CAG TTC CCC ATC CTA TCC ATC ACC TGG     350
Gln Glu Leu Val Lys Lys Gly Gln Phe Pro Ile Leu Ser Ile Thr Trp
 75                  80                  85                  90

GAA CAT GCA GGG CGG TAT TGC TGT ATC TAT GGC AGC CAC ACT GCA GGC     398
Glu His Ala Gly Arg Tyr Cys Cys Ile Tyr Gly Ser His Thr Ala Gly
                 95                 100                 105

CTC TCA GAG AGC AGT GAC CCC CTG GAG CTG GTG GTG ACA GGA GCC TAC     446
Leu Ser Glu Ser Ser Asp Pro Leu Glu Leu Val Val Thr Gly Ala Tyr
             110                 115                 120

AGC AAA CCC ACC CTC TCA GCT CTG CCC AGC CCT GTG GTG ACC TCA GGA     494
Ser Lys Pro Thr Leu Ser Ala Leu Pro Ser Pro Val Val Thr Ser Gly
         125                 130                 135

GGG AAT GTG ACC ATC CAG TGT GAC TCA CAG GTG GCA TTT GAT GGC TTC     542
Gly Asn Val Thr Ile Gln Cys Asp Ser Gln Val Ala Phe Asp Gly Phe
     140                 145                 150

ATT CTG TGT AAG GAA GGA GAA GAT GAA CAC CCA CAA TGC CTG AAC TCC     590
Ile Leu Cys Lys Glu Gly Glu Asp Glu His Pro Gln Cys Leu Asn Ser
155                 160                 165                 170

CAT TCC CAT GCC CGT GGG TCA TCC CGG GCC ATC TTC TCC GTG GGC CCC     638
His Ser His Ala Arg Gly Ser Ser Arg Ala Ile Phe Ser Val Gly Pro
                 175                 180                 185

GTG AGC CCA AGT CGC ACG TGC TCC TAC AGG TGC TAT GGT TAT GAC TCG     686
Val Ser Pro Ser Arg Arg Trp Ser Tyr Arg Cys Tyr Gly Tyr Asp Ser
             190                 195                 200

CGC GCT CCC TAT GTG TGG TCT CTA CCC AGT CAT CTC CTG GGG CTC CTG     734
Arg Ala Pro Tyr Val Trp Ser Leu Pro Ser His Leu Leu Gly Leu Leu
         205                 210                 215

GTC CCA GCT GTT TCT AAG AAG CCA TCA CTC TCA GTG CAG CCG GGT CCT     782
Val Pro Gly Val Ser Lys Lys Pro Ser Leu Ser Val Gln Pro Gly Pro
     220                 225                 230

GTC GTG GCC CCT GGG GAG AAG CTG ACC TTC CAG TGT GGC TCT GAT GCC     830
Val Val Ala Pro Gly Glu Lys Leu Thr Phe Gln Cys Gly Ser Asp Ala
235                 240                 245                 250
```

TABLE 3-continued

```
GGC TAC GAC ACA TTT GTT CTG TAC AAG GAG TGG GGA CGT GAC TTC CTC     878
Gly Tyr Asp Arg Phe Val Leu Tyr Lys Glu Trp Gly Arg Asp Phe Leu
                255                 260                 265

CAG CGC CCT GGC CCC CAG CCC CAG GCT GGG CTC TCC CAG GCC AAC TTC     926
Gln Arg Pro Gly Arg Gln Pro Gln Ala Gly Leu Ser Gln Ala Asn Phe
                270                 275                 280

ACC CTG GGC CCT GTG AGC CGC TCC TAC GGG GGC CAG TAC ACA TGC TCC     974
Thr Leu Gly Pro Val Ser Arg Ser Tyr Gly Gly Gln Tyr Thr Cys Ser
                285                 290                 295

GGT GCA TAC AAC CTC TCC TCC GAG TGG TCG GCC CCC AGC GAC CCC CTG    1022
Gly Ala Tyr Asn Leu Ser Ser Glu Trp Ser Ala Pro Ser Asp Pro Leu
                300                 305                 310

GAC ATC CTG ATC ACA GGA CAG ATC CGT GCC AGA CCC TTC CTC TCC GTG    1070
Asp Ile Leu Ile Thr Gly Gln Ile Arg Ala Arg Pro Phe Leu Ser Val
315                 320                 325                 330

CGG CCG GGC CCC ACA GTG CGC TCA GGA GAG AAC GTG ACC CTG CTG TGT    1118
Arg Pro Gly Pro Thr Val Ala Ser Gly Glu Asn Val Thr Leu Leu Cys
                335                 340                 345

CAG TCA CAG GGA GGG ATG CAC ACT TTC CTT TTC ACC AAG GAG GGG GCA    1166
Gln Ser Gln Gly Gly Met His Thr Phe Leu Leu Thr Lys Glu Gly Ala
                350                 355                 360

GCT GAT TCC CCG CTG CGT CTA AAA TCA AAG CGC CAA TCT CAT AAG TAC    1214
Ala Asp Ser Pro Leu Arg Leu Lys Ser Lys Arg Gln Ser His Lys Tyr
                365                 370                 375

CAG GCT GAA TTC CCC ATG ACT CCT GTG ACC TCG GCC CAC GCG GGG ACC    1262
Gln Ala Glu Phe Pro Met Ser Pro Val Thr Ser Ala His Ala Gly Thr
            380                 385                 390

TAC AGG TGC TAC GGC TCA CTC AGC TCC AAC CCC TAC CTG CTG ACT CAC    1310
Tyr Arg Cys Tyr Gly Ser Leu Ser Ser Asn Pro Tyr Leu Leu Thr His
395                 400                 405                 410

CCC AGT GAC CCC CTG GAG CTC GTG GTC TCA GGA GCA GCT GAG ACC CTC    1358
Pro Ser Asp Pro Leu Glu Leu Val Val Ser Gly Ala Ala Glu Thr Leu
                415                 420                 425

AGC CCA CCA CAA AAC AAG TCC GAC TCC AAG GCT GGT GAG TGAGGAGATG     1407
Ser Pro Pro Gln Asn Lys Ser Asp Ser Lys Ala Gly Glu
                430                 435

CTTGCCGTGA TGACGCTGGG CACAGAGGGT CAGGTCCTGT CAAGAGGAGC TGGGTGTCCT 1467

GGGTGGACAT TTGAAGAATT ATATTCATTC CAACTTGAAG AATTATTCAA CACCTTTAAC 1527

AATGTATATG TGAAGTACTT TATTCTTTCA TATTTTAAAA ATAAAAGATA ATTATCCATG 1587

AAAAAAAAAA AAAAAAAAAA AAAGGGCGGC CGC                              1620
```

YYB04: Related to YYB01, apparently through alternative splicing from the same or a very highly related gene. The coding region runs from about 191 to 1493, but the initiation methionine may actually be at the numbered Met at 18. See SEQ ID NO: 13 and 14. Another transcript was isolated which contains evidence for existence of an insert of sequence TGCTACGGCT CACTCAACTC CGACCCCTAC CTGCTGTCTC ACCCCAGTGA GCCCCTGGAG CTCGTGGTCT CAGG between residues 1426 and 1427, which changes the downstream reading frame of the subsequent sequence, to encode, from residue 413, CYG SLNSD PYLLS HPSEP LELVV SGPSM GSSPP PTGPI STPAG PEDQP LTPTG SDPQS GLGRH LGVVI GILVA VVLLL LLLLL LFLIL RHRRQ GKHWT STQRK ADFQH PAGAV GPEPT DRGLQ WRSSP AADAQ EENLY AAVKD TQPED GVEMD TRAAA SEAPQ DVTYA QLHSL TLRRK ATEPP PSQER EPPAE PSIYA TLAIH. (SEQ ID NO: 15 and 16.)
This alternative sequence contains a transmembrane segment from about 478 to 500.

```
GTCGACCCAC GCGTCCGGTC AACTTTTCTT CCCCTACTTC CCTGCATTTC TCCTCTGTGC   60

TCACTGCCAC ACGCAGCTCA ACCTGGACGG CACAGCCAGA TGCGAGATGC GTCTCTGCTG  120

ATCTGAGTCT GCCTGCAGCA TGGACCTGGG TCTTCCCTGA AGCATCTCCA GGGCTGGAGG  180
```

TABLE 3-continued

```
GACGACTGCC ATG CAC CGA GGG CTC ATC CAT CCG CAG AGC AGG GCA GTG      229
           Met His Arg Gly Leu Ile His Pro Gln Ser Arg Ala Val
            1               5                  10

GGA GGA GAC GCC ATG ACC CCC ATC GTC ACA GTC CTG ATC TGT CTC GGG     277
Gly Gly Asp Ala Met Thr Pro Ile Val Thr Val Leu Ile Cys Leu Gly
 15               20                  25

CTG AGT CTG GGC CCC AGG ACC CAC GTG CAG ACA GGG ACC ATC CCC AAG     325
Leu Ser Leu Gly Pro Arg Thr His Val Gln Thr Gly Thr Ile Pro Lys
 30               35                  40                  45

CCC ACC CTG TGG GCT GAG CCA GAC TCT GTG ATC ACC CAG GGG AGT CCC     373
Pro Thr Leu Trp Ala Glu Pro Asp Ser Val Ile Thr Gln Gly Ser Pro
                 50                  55                  60

GTC ACC CTC AGT TGT CAG GGG AGC CTT GAA GCC CAG GAG TAC CGT CTA     421
Val Thr Leu Ser Cys Gln Gly Ser Leu Glu Ala Gln Glu Tyr Arg Leu
             65                  70                  75

TAT AGG GAG AAA AAA TCA GCA TCT TGG ATT ACA CGG ATA CGA CCA GAG     469
Tyr Arg Glu Lys Lys Ser Ala Ser Trp Ile Thr Arg Ile Arg Pro Glu
         80                  85                  90

CTT GTG AAG AAC GGC CAG TTC CAC ATC CCA TCC ATC ACC TGG GAA CAC     517
Leu Val Lys Asn Gly Gln Phe His Ile Pro Ser Ile Thr Trp Glu His
     95                  100                 105

ACA GGG CGA TAT GGC TGT CAG TAT TAC AGC CGC GCT CGG TGG TCT GAG     565
Thr Gly Arg Tyr Gly Cys Gln Tyr Tyr Ser Arg Ala Arg Trp Ser Glu
110                 115                 120                 125

CTC AGT GAC CCC CTG GTG CTG GTG ATG ACA GGA GCC TAC CCA AAA CCC     613
Leu Ser Asp Pro Leu Val Leu Val Met Thr Gly Ala Tyr Pro Lys Pro
                130                 135                 140

ACC CTC TCA GCC CAG CCC AGC CCT GTG GTG ACC TCA GGA GGA AGG GTG     661
Thr Leu Ser Ala Gln Pro Ser Pro Val Val Thr Ser Gly Gly Arg Val
                145                 150                 155

ACC CTC CAG TGT GAG TCA CAG GTG GCA TTT GGC GGC TTC ATT CTG TGT     709
Thr Leu Gln Cys Glu Ser Gln Val Ala Phe Gly Gly Phe Ile Leu Cys
            160                 165                 170

AAG GAA GGA GAA GAT GAA CAC CCA CAA TGC CTG AAC TCC CAG CCC CAT     757
Lys Glu Gly Glu Asp Glu His Pro Gln Cys Leu Asn Ser Gln Pro His
        175                 180                 185

GCC CGT GGG TCG TCC CGC GCC ATC TTC TCC GTG GGC CCC GTG AGC CCG     805
Ala Arg Gly Ser Ser Arg Ala Ile Phe Ser Val Gly Pro Val Ser Pro
190                 195                 200                 205

AAT CGC AGG TGG TCG CAC AGG TGC TAT GGT TAT GAC TTG AAC TCT CCC     853
Asn Arg Arg Trp Ser His Arg Cys Tyr Gly Tyr Asp Leu Asn Ser Pro
                210                 215                 220

TAT GTG TGG TCT TCA CCC AGT GAT CTC CTG GAG CTC CTG GTC CCA GGT     901
Tyr Val Trp Ser Ser Pro Ser Asp Leu Leu Glu Leu Leu Val Pro Gly
                225                 230                 235

GTT TCT AAG AAG CCA TCA CTC TCA GTG CAG CCG GGT CCT GTC GTG GCC     949
Val Ser Lys Lys Pro Ser Leu Ser Val Gln Pro Gly Pro Val Val Ala
            240                 245                 250

CCT GGG GAA AGC CTG ACC CTC CAG TGT GTC TCT GAT GTC GGC TAT GAC     997
Pro Gly Glu Ser Leu Thr Leu Gln Cys Val Ser Asp Val Gly Tyr Asp
        255                 260                 265

AGA TTT GTT CTG TAC AAG GAG GGG GAA CGT GAC CTT CGC CAG CTC CCT    1045
Arg Phe Val Leu Tyr Lys Glu Gly Glu Arg Asp Leu Arg Gln Leu Pro
270                 275                 280                 285

GGC CGG CAG CCC CAG GCT GGG CTC TCC CAC GCC AAC TTC ACC CTG GGC    1093
Gly Arg Gln Pro Gln Ala Gly Leu Ser His Ala Asn Phe Thr Leu Gly
                290                 295                 300

CCT GTG AGC CGC TCC TAC GGG GGC CAG TAC AGA TGC TAC GGT GCA TAC    1141
Pro Val Ser Arg Ser Tyr Gly Gly Gln Tyr Arg Cys Tyr Gly Ala Tyr
                305                 310                 315
```

TABLE 3-continued

```
AAC CTC TCC TCC GAG TGG TCG GCC CCC AGC GAC CCC CTG GAC ATC CTG    1189
Asn Leu Ser Ser Glu Trp Ser Ala Pro Ser Asp Pro Leu Asp Ile Leu
            320                 325                 330

ATC ACA GGA CAG ATC CAT GGC ACA CCC TTC ATC TCA GTG CAG CCA GGC    1237
Ile Thr Gly Gln Ile His Gly Thr Pro Phe Ile Ser Val Gln Pro Gly
            335                 340                 345

CCC ACA GTG GCC TCA GGA GAG AAC GTG ACC CTG CTG TGT CAG TCA TGG    1285
Pro Thr Val Ala Ser Gly Glu Asn Val Thr Leu Leu Cys Gln Ser Trp
350                 355                 360                 365

CGG CAG TTC CAC ACT TTC CTT CTG ACC AAG GCG GGA GCA GCT GAT GCC    1333
Arg Gln Phe His Thr Phe Leu Leu Thr Lys Ala Gly Ala Ala Asp Ala
            370                 375                 380

CCA CTC CGT CTA AGA TCA ATA CAC GAA TAT CCT AAG TAC CAG GCT GAA    1381
Pro Leu Arg Leu Arg Ser Ile His Glu Tyr Pro Lys Tyr Gln Ala Glu
            385                 390                 395

TTC CCC ATG AGT CCT GTG ACC TCA GCC CAC GCG GGG ACC TAC AGG ACC    1429
Phe Pro Met Ser Pro Val Thr Ser Ala His Ala Gly Thr Tyr Arg Thr
            400                 405                 410

CTC CAT GGG TTC CAG CCC CCC ACC CAC CGG TCC CAT CTC CAC ACC TGC    1477
Leu His Gly Phe Gln Pro Pro Thr His Arg Ser His Leu His Thr Cys
            415                 420                 425

AGG CCC TGAGGACCAG CCCCTCACCC CCACTGGGTC GGATCCCCAA AGTGGTCTGG     1533
Arg Pro
430

GAAGGCACCT GGGGGTTGTG ATCGGCATCT TGGTGGCCGT CGTCCTACTG CTCCTCCTCC 1593

TCCTCCTCCT CTTCCTCATC CTCCGACATC GACGTCAGGG CAAACACTGG ACATCGACCC 1653

AGAGAAAGGC TGATTTCCAA CATCCTGCAC GGGCTGTGGG CCAGAGCCC ACAGACAGAG  1713

GCCTGCAGTG GAGGTCCAGC CCAGCTGCCG ACGCCCAGGA AGAAAACCTC TATGCTGCCG 1773

TGAAGGACAC ACAGCCTGAA GATGGGGTGG AGATGGACAC TCGGGCTGCT GCATCTGAAG 1833

CCCCCCAGGA TGTGACCTAC GCCCAGCTGC ACAGCTTGAC CCTCAGACGC AAGGCAACTG 1893

AGCCTCCTCC ATCCCAGGAA AGGGAACCTC CAGCTGAGCC CAGCATTTAC GCCACCCTGG 1953

CCATCCACTA GCCCGGAGGG TACGCAGACT CCACACTCAG TAGAAGGACA CTCAGGACTG 2013

CTGAAGGCAC GGGAGCTGCC CCCAGTGGAC ACCAATGAAC CCCAGTCAGC CTGGACCCCT 2073

AACAAAGACC ATGAGGAGAT GCTGGGAACT TTGGGACTCA CTTGATTCTG CAGTGGAAAT 2133

AACTAATATC CCTACATTTT TTAATTAAAG CAACAGACTT CTCAATAATC AATGAGTTAA 2193

CCGA                                                              2197
```

| A KTE03 embodiment designated KLM63 (SEQ ID NO: 17 and 18): |
| --- |

```
AAAGAAGTCA ACTTTTCTTC CCCTACTTCC CTGCATTTCT CCTCTGTGCT CACTGCCACA   60

CGCAGCTCAA CCTGGACGGC ACAGCCAGAT GCGAGATGCG TCTCTGCTGA TCTGAGTCTG  120

CCTGCAGCAT GGACCTGGGT CTTCCCTGAA GCATCTCCAG GGCTGGAGGG ACGACTGCC   179

ATG CAC CGA GGG CTC ATC CAT CCG CAG AGC AGG GCA GTG GGA GGA GAC     227
Met His Arg Gly Leu Ile His Pro Gln Ser Arg Ala Val Gly Gly Asp
  1               5                  10                  15

GCC ATG ACC CCC ATC GTC ACA GTC CTG ATC TGT CTC GGG CTG AGT CTG     275
Ala Met Thr Pro Ile Val Thr Val Leu Ile Cys Leu Gly Leu Ser Leu
            20                  25                  30

GGC CCC AGG ACC CAC GTG CAG ACA GGG ACC ATC CCC AAG CCC ACC CTG     323
Gly Pro Arg Thr His Val Gln Thr Gly Thr Ile Pro Lys Pro Thr Leu
            35                  40                  45

TGG GCT GAG CCA GAC TCT GTG ATC ACC CAG GGG AGT CCC GTC ACC CTC     371
Trp Ala Glu Pro Asp Ser Val Ile Thr Gln Gly Ser Pro Val Thr Leu
```

TABLE 3-continued

```
           50                      55                      60
AGT TGT CAG GGG AGC CTT GAA GCC CAG GAG TAC CGT CTA TAT AGG GAG    419
Ser Cys Gln Gly Ser Leu Glu Ala Gln Glu Tyr Arg Leu Tyr Arg Glu
 65                      70                      75                      80

AAA AAA TCA GCA TCT TGG ATT ACA CGG ATA CGA CCA GAG CTT GTG AAG    467
Lys Lys Ser Ala Ser Trp Ile Thr Arg Ile Arg Pro Glu Leu Val Lys
                         85                      90                      95

AAC GGC CAG TTC CAC ATC CCA TCC ATC ACC TGG GAA CAC ACA GGG CGA    515
Asn Gly Gln Phe His Ile Pro Ser Ile Thr Trp Glu His Thr Gly Arg
                     100                     105                     110

TAT GGC TGT CAG TAT TAC AGC CGC GCT CGG TGG TCT GAG CTC AGT GAC    563
Tyr Gly Cys Gln Tyr Tyr Ser Arg Ala Arg Trp Ser Glu Leu Ser Asp
                 115                     120                     125

CCC CTG GTG CTG GTG ATG ACA GGA GCC TAC CCA AAA CCC ACC CTC TCA    611
Pro Leu Val Leu Val Met Thr Gly Ala Tyr Pro Lys Pro Thr Leu Ser
         130                     135                     140

GCC CAG CCC AGC CCT GTG GTG ACC TCA GGA GGA AGG GTG ACC CTC CAG    659
Ala Gln Pro Ser Pro Val Val Thr Ser Gly Gly Arg Val Thr Leu Gln
145                     150                     155                     160

TGT GAG TCA CAG GTG GCA TTT GGC GGC TTC ATT CTG TGT AAG GAA GGA    707
Cys Glu Ser Gln Val Ala Phe Gly Gly Phe Ile Leu Cys Lys Glu Gly
                         165                     170                     175

GAA GAT GAA CAC CCA CAA TGC CTG AAC TCC CAG CCC CAT GCC CGT GGG    755
Glu Asp Glu His Pro Gln Cys Leu Asn Ser Gln Pro His Ala Arg Gly
                     180                     185                     190

TCG TCC CGC GCC ATC TTC TCC GTG GGC CCC GTG AGC CCG AAT CGC AGG    803
Ser Ser Arg Ala Ile Phe Ser Val Gly Pro Val Ser Pro Asn Arg Arg
                 195                     200                     205

TGG TCG CAC AGG TGC TAT GGT TAT GAC TTG AAC TCT CCC TAT GTG TGG    851
Trp Ser His Arg Cys Tyr Gly Tyr Asp Leu Asn Ser Pro Tyr Val Trp
         210                     215                     220

TCT TCA CCC AGT GAT CTC CTG GAG CTC CTG GTC CCA GGT GTT TCT AAG    899
Ser Ser Pro Ser Asp Leu Leu Glu Leu Leu Val Pro Gly Val Ser Lys
225                     230                     235                     240

AAG CCA TCA CTC TCA GTG CAG CCG GGT CCT GTC GTG GCC CCT GGG GAA    947
Lys Pro Ser Leu Ser Val Gln Pro Gly Pro Val Val Ala Pro Gly Glu
                         245                     250                     255

AGC CTG ACC CTC CAG TGT GTC TCT GAT GTC GGC TAT GAC AGA TTT GTT    995
Ser Leu Thr Leu Gln Cys Val Ser Asp Val Gly Tyr Asp Arg Phe Val
                     260                     265                     270

CTG TAC AAG GAG GGG GAA CGT GAC CTT CGC CAG CTC CCT GGC CGG CAG   1043
Leu Tyr Lys Glu Gly Glu Arg Asp Leu Arg Gln Leu Pro Gly Arg Gln
                 275                     280                     285

CCC CAG GCT GGG CTC TCC CAG GCC AAC TTC ACC CTG GGC CCT GTG AGC   1091
Pro Gln Ala Gly Leu Ser Gln Ala Asn Phe Thr Leu Gly Pro Val Ser
         290                     295                     300

CGC TCC TAC GGG GGC CAG TAC AGA TGC TAC GGT GCA TAC AAC CTC TCC   1139
Arg Ser Tyr Gly Gly Gln Tyr Arg Cys Tyr Gly Ala Tyr Asn Leu Ser
305                     310                     315                     320

TCC GAG TGG TCG GCC CCC AGC GAC CCC CTG GAC ATC CTG ATC ACA GGA   1187
Ser Glu Trp Ser Ala Pro Ser Asp Pro Leu Asp Ile Leu Ile Thr Gly
                         325                     330                     335

CAG ATC CAT GGC ACA CCC TTC ATC TCA GTG CAG CCA GGC CCC ACA GTG   1235
Gln Ile His Gly Thr Pro Phe Ile Ser Val Gln Pro Gly Pro Thr Val
                     340                     345                     350

GCC TCA GGA GAG AAC GTG ACC CTG CTG TGT CAG TCA TGG CGG CAG TTC   1283
Ala Ser Gly Glu Asn Val Thr Leu Leu Cys Gln Ser Trp Arg Gln Phe
                 355                     360                     365

CAC ACT TTC CTT CTG ACC AAG GCG GGA GCA GCT GAT GCC CCA CTC CGT   1331
```

TABLE 3-continued

```
His Thr Phe Leu Leu Thr Lys Ala Gly Ala Ala Asp Ala Pro Leu Arg
    370                 375                 380

CTA AGA TCA ATA CAC GAA TAT CCT AAG TAC CAG GCT GAA TTC CCC ATG      1379
Leu Arg Ser Ile His Glu Tyr Pro Lys Tyr Gln Ala Glu Phe Pro Met
385                 390                 395                 400

AGT CCC GTG ACC TCA GCC CAC GCG GGG ACC TAC AGG TGC TAC GGC TCA      1427
Ser Pro Val Thr Ser Ala His Ala Gly Thr Tyr Arg Cys Tyr Gly Ser
                405                 410                 415

CTC AAC TCC GAC CCC TAC CTG CTG TCT CAC CCC AGT GAG CCC CTG GAG      1475
Leu Asn Ser Asp Pro Tyr Leu Leu Ser His Pro Ser Glu Pro Leu Glu
            420                 425                 430

CTC GTC GTC TCA GGA CCC TCC ATG GGT TCC AGC CCC CCA CCC ACC GGT      1523
Leu Val Val Ser Gly Pro Ser Met Gly Ser Ser Pro Pro Pro Thr Gly
        435                 440                 445

CCC ATC TCC ACA CCT GCA GGC CCT GAG GAC CAG CCC CTC ACC CCC ACT      1571
Pro Ile Ser Thr Pro Ala Gly Pro Glu Asp Gln Pro Leu Thr Pro Thr
    450                 455                 460

GGG TCG GAT CCC CAA AGT GGT CTG GGA AGG CAC CTG GGG GTT GTG ATC      1619
Gly Ser Asp Pro Gln Ser Gly Leu Gly Arg His Leu Gly Val Val Ile
465                 470                 475                 480

GGC ATC TTG GTG GCC GTC GTC CTA CTG CTC CTC CTC CTC CTC CTC CTC      1667
Gly Ile Leu Val Ala Val Val Leu Leu Leu Leu Leu Leu Leu Leu Leu
                485                 490                 495

TTC CTC ATC CTC CGA CAT CGA CGT CAG GGC AAA CAC TGG ACA TCG ACC      1715
Phe Leu Ile Leu Arg His Arg Arg Gln Gly Lys His Trp Thr Ser Thr
            500                 505                 510

CAG AGA AAG GCT GAT TTC CAA CAT CCT GCA GGG GCT GTG GGG CCA GAG      1763
Gln Arg Lys Ala Asp Phe Gln His Pro Ala Gly Ala Val Gly Pro Glu
        515                 520                 525

CCC ACA GAC AGA GGC CTG CAG TGG AGG TCC AGC CCA GCT GCC GAC GCC      1811
Pro Thr Asp Arg Gly Leu Gln Trp Arg Ser Ser Pro Ala Ala Asp Ala
    530                 535                 540

CAG GAA GAA AAC CTC TAT GCT GCC GTG AAG GAC ACA CAG CCT GAA GAT      1859
Gln Glu Glu Asn Leu Tyr Ala Ala Val Lys Asp Thr Gln Pro Glu Asp
545                 550                 555                 560

GGG GTG GAG ATG GAC ACT CGG GCT GCT GCA TCT GAA GCC CCC AGG GAT      1907
Gly Val Glu Met Asp Thr Arg Ala Ala Ala Ser Glu Ala Pro Gln Asp
                565                 570                 575

GTG ACC TAC GCC CAG CTG CAC AGC TTG ACC CTC AGA CGG AAG GCA ACT      1955
Val Thr Tyr Ala Gln Leu His Ser Leu Thr Leu Arg Arg Lys Ala Thr
            580                 585                 590

GAG CCT CCT CCA TCC CAG GAA AGG GAA CCT CCA CCT GAG CCC AGC ATC      2003
Glu Pro Pro Pro Ser Gln Glu Arg Glu Pro Pro Ala Glu Pro Ser Ile
        595                 600                 605

TAC GCC ACC CTG GCC ATC CAC TAGCCCGGAG GGTACGCAGA CTCCACACTC         2054
Tyr Ala Thr Leu Ala Ile His
    610                 615

AGTAGAAGGA GACTCAGGAC TGCTGAAGGC ACGGGAGCTG CCCCCAGTGG ACACCAATGA    2114

ACCCCAGTCA GCCTGGACCC CTAACAAAGA CCATGAGGAG ATGCTGGGAA CTTTGGGACT    2174

CACTTGATTC TGCAGTCGAA ATAACTAATA TCCCTACATT TTTTAATTAA AGCAACAGAC    2234

TTCTCAATAA TCAATGAGTT AACCGAGAAA ACTAAAATCA GAAGTAAGAA TGTGCTTTAA    2294

ACTGAATCAC AATATAAATA TTACACATCA CACAATGAAA TTGAAAAAGT ACAAACCACA    2354

AATGAAAAAA GTAGAAACGA AAAAAAAAAA AAAA                                2388
```

A KTE03 embodiment designated KLM66 (SEQ IDS NO: 19 and 20):

```
GTCAACTTTT CTTCCCCTAC TTCCCTGCAT TTCTCCTCTG TGCTCACTGC CACACGCAGC    60
```

TABLE 3-continued

```
TCAACCTGGA CGGCACAGCC AGATGCGAGA TGCGTCTCTG CTGATCTGAG TCTGCCTGCA   120

GCATGGACCT GGGTCTTCCC TGAAGCATCT CCAGGGCTGG AGGGACGACT GCC ATG     176
                                                            Met
                                                              1

CAC CGA GGG CTC ATC CAT CCG CAG AGC AGG GCA GTG GGA GGA GAC GCC   224
His Arg Gly Leu Ile His Pro Gln Ser Arg Ala Val Gly Gly Asp Ala
              5                  10                  15

ATG ACC CCC ATC GTC ACA GTC CTG ATC TGT CTC GGG CTG AGT CTG GGC   272
Met Thr Pro Ile Val Thr Val Leu Ile Cys Leu Gly Leu Ser Leu Gly
             20                  25                  30

CCC AGG ACC CAC GTG CAG ACA GGG ACC ATC CCC AAG CCC ACC CTG TGG   320
Pro Arg Thr His Val Gln Thr Gly Thr Ile Pro Lys Pro Thr Leu Trp
         35                  40                  45

GCT GAG CCA GAC TCT GTG ATC ACC CAG GGG AGT CCC GTC ACC CTC ACT   368
Ala Glu Pro Asp Ser Val Ile Thr Gln Gly Ser Pro Val Thr Leu Ser
 50                  55                  60                  65

TGT CAG GGG AGC CTT GAA GCC CAG GAG TAC CGT CTA TAT AGG GAG AAA   416
Cys Gln Gly Ser Leu Glu Ala Gln Glu Tyr Arg Leu Tyr Arg Glu Lys
                 70                  75                  80

AAA TCA GCA TCT TGG ATT ACA CGG ATA CGA CCA GAG CTT GTG AAG AAC   464
Lys Ser Ala Ser Trp Ile Thr Arg Ile Arg Pro Glu Leu Val Lys Asn
             85                  90                  95

GGC CAG TTC CAC ATC CCA TCC ATC ACC TGG GAA CAC ACA GGG CGA TAT   512
Gly Gln Phe His Ile Pro Ser Ile Thr Trp Glu His Thr Gly Arg Tyr
            100                 105                 110

GGC TGT CAG TAT TAC AGC CGC GCT CGG TGG TCT GAG CTC AGT GAC CCC   560
Gly Cys Gln Tyr Tyr Ser Arg Ala Arg Trp Ser Glu Leu Ser Asp Pro
        115                 120                 125

CTG GTG CTG GTG ATG ACA GGA GCC TAC CCA AAA CCC ACC CTC TCA GCC   608
Leu Val Leu Val Met Thr Gly Ala Tyr Pro Lys Pro Thr Leu Ser Ala
130                 135                 140                 145

CAG CCC AGC CCT GTG GTC ACC TCA GGA GGA AGG GTG ACC CTC CAG TCT   656
Gln Pro Ser Pro Val Val Thr Ser Gly Gly Arg Val Thr Leu Gln Cys
                150                 155                 160

GAG TCA CAG GTG GCA TTT GGC GGC TTC ATT CTG TGT AAG GAA GGA GAA   704
Glu Ser Gln Val Ala Phe Gly Gly Phe Ile Leu Cys Lys Glu Gly Glu
            165                 170                 175

GAT GAA CAC CCA CAA TGC CTG AAC TCC CAG CCC CAT GCC CGT GGG TCG   752
Asp Glu His Pro Gln Cys Leu Asn Ser Gln Pro His Ala Arg Gly Ser
        180                 185                 190

TCC CGC GCC ATC TTC TCC GTG GGC CCC GTG AGC CCG AAT CGC AGG TGG   800
Ser Arg Ala Ile Phe Ser Val Gly Pro Val Ser Pro Asn Arg Arg Trp
    195                 200                 205

TCG CAC AGG TGC TAT GGT TAT GAC TTG AAC TCT CCC TAT GTG TGG TCT   848
Ser His Arg Cys Tyr Gly Tyr Asp Leu Asn Ser Pro Tyr Val Trp Ser
210                 215                 220                 225

TCA CCC AGT GAT CTC CTG GAG CTC CTG GTC CCA GGT GTT TCT AAG AAG   896
Ser Pro Ser Asp Leu Leu Glu Leu Leu Val Pro Gly Val Ser Lys Lys
                230                 235                 240

CCA TCA CTC TCA GTG CAG CCG GGT CCT GTC GTG GCC CCT GGG GAA AGC   944
Pro Ser Leu Ser Val Gln Pro Gly Pro Val Val Ala Pro Gly Glu Ser
            245                 250                 255

CTG ACC CTC CAG TGT GTC TCT GAT GTC GGC TAT GAC AGA TTT GTT CTG   992
Leu Thr Leu Gln Cys Val Ser Asp Val Gly Tyr Asp Arg Phe Val Leu
        260                 265                 270

TAC AAG GAG GGG GAA CGT GAC CTT CGC CAG CTC CCT GGC CGG CAG CCC  1040
Tyr Lys Glu Gly Glu Arg Asp Leu Arg Gln Leu Pro Gly Arg Gln Pro
    275                 280                 285

CAG GCT GGG CTC TCC CAG GCC AAC TTC ACC CTG GGC CCT GTG AGC CGC  1088
```

TABLE 3-continued

| | | | | | | | | | | | | |
|---|---|---|---|---|---|---|---|---|---|---|---|---|
|Gln|Ala|Gly|Leu|Ser|Gln|Ala|Asn|Phe|Thr|Leu|Gly|Pro|Val|Ser|Arg|
|290| | | |295| | | |300| | | |305| | | |

```
TCC TAC GGG GGC CAG TAC AGA TGC TAC GGT GCA TAC AAC CTC TCC TCC  1136
Ser Tyr Gly Gly Gln Tyr Arg Cys Tyr Gly Ala Tyr Asn Leu Ser Ser
                310                 315                 320

GAG TGG TCG GCC CCC AGC GAC CCC CTG GAC ATC CTG ATC ACA GGA CAG  1184
Glu Trp Ser Ala Pro Ser Asp Pro Leu Asp Ile Leu Ile Thr Gly Gln
            325                 330                 335

ATC CAT GGC ACA CCC TTC ATC TCA GTG CAG CCA GGC CCC ACA GTG GCC  1232
Ile His Gly Thr Pro Phe Ile Ser Val Gln Pro Gly Pro Thr Val Ala
        340                 345                 350

TCA GGA GAG AAC GTG ACC CTG CTG TGT CAG TCA TGG CGG CAG TTC CAC  1280
Ser Gly Glu Asn Val Thr Leu Leu Cys Gln Ser Trp Arg Gln Phe His
    355                 360                 365

ACT TTC CTT CTG ACC AAG GCG GGA GCA GCT GAT GCC CCA CTC CGT CTA  1328
Thr Phe Leu Leu Thr Lys Ala Gly Ala Ala Asp Ala Pro Leu Arg Leu
370                 375                 380                 385

AGA TCA ATA CAC GAA TAT CCT AAG TAC CAG GCT GAA TTC CCC ATC AGT  1376
Arg Ser Ile His Glu Tyr Pro Lys Tyr Gln Ala Glu Phe Pro Met Ser
                390                 395                 400

CCT GTG ACC TCA GCC CAC GCG GGG ACC TAC AGG ACC CTC CAT GGG TTC  1424
Pro Val Thr Ser Ala His Ala Gly Thr Tyr Arg Thr Leu His Gly Phe
            405                 410                 415

CAG CCC CCC ACC CAC CGG TCC CAT CTC CAC ACC TGC AGG CCC           1466
Gln Pro Pro Thr His Arg Ser His Leu His Thr Cys Arg Pro
        420                 425                 430

TGAGGACCAG CCCCTCACCC CCACTGGGTC GGATCCCCAA AGTGGTCTGG GAAGGCACCT 1526
GGGGGTTGTG ATCGGCATCT TGGTGGCCGT CGTCCTACTG CTCCTCCTCC TCCTCCTCCT 1586
CTTCCTCATC CTCCGACATC GACGTCAGGG CAAACACTGG ACATCGACCC AGAGAAAGGC 1646
TGATTTCCAA CATCCTGCAG GGGCTGTGGG GCCAGAGCCC ACAGACAGAG GCCTGCAGTG 1706
GAGGTCCAGC CCAGCTGCCG ACGCCCAGGA AGAAAACCTC TATGCTGCCG TGAAGGACAC 1766
ACAGCCTGAA GATGGGGTGG AGATGGACAC TCGGGCTGCT GCATCTGAAG CCCCCCAGGA 1826
TGTGACCTAC GCCCAGCTGC ACAGCTTGAC CCTCAGACGG AAGGCAACTG AGCCTCCTCC 1886
ATCCCAGGAA AGGGAACCTC CAGCTGAGCC CAGCATCTAC GCCACCCTGG CCATCCACTA 1946
GCCCGGAGGG TACGCAGACT CCACACTCAG TAGAAGGAGA CTCAGGACTG CTGAAGGCAC 2006
GGGAGCTGCC CCCAGTGGAC ACCAATGAAC CCCAGTCAGC CTGGACCCCT AACAAAGACC 2066
ATGAGGAGAT GCTGGGAACT TTGGGACTCA CTTGATTCTG CAGTCGAAAT AACTAATATC 2126
CCTACATTTT TTAATTAAAG CAACAGACTT CTCAATAATC AATGAGTTAA CCGAGAAAAC 2186
TAAAAAAAA AAAA                                                    2200
```

| A KTEO3 embodiment designated KLM67 (SEQ ID NO: 21 and 22): |
|---|

```
GCCACACGCA GCTCAGCCTG GCGGCACAG CCAGATGCGA GATGCGTCTC TGCTGATCTG   60
AGTCTGCCTG CAGCATGGAC CTGGGTCTTC CCTGAAGCAT CTCCAGGGCT GGAGGGACGA  120
CTGCCATGCA CCGAGGGCTC ATCCATCCAC AGAGCAGGGC AGTGGGAGGA GACGCC      176

ATG ACC CCC ATC CTC ACG GTC CTG ATC TGT CTC GGG CTG AGT CTG GGC   224
Met Thr Pro Ile Leu Thr Val Leu Ile Cys Leu Gly Leu Ser Leu Gly
 1                   5                  10                  15

CCC CGG ACC CAC GTG CAG GCA GGG CAC CTC CCC AAG CCC ACC CTC TGG   272
Pro Arg Thr His Val Gln Ala Gly His Leu Pro Lys Pro Thr Leu Trp
            20                  25                  30

GCT GAA CCA GGC TCT GTG ATC ACC CAG GGG AGT CCT GTG ACC CTC AGC   320
Ala Glu Pro Gly Ser Val Ile Thr Gln Gly Ser Pro Val Thr Leu Arg
```

TABLE 3-continued

```
              35                    40                     45
TGT CAG GGG GGC CAG GAG ACC CAG GAG TAC CGT CTA TAT AGA GAA AAG    368
Cys Gln Gly Gly Gln Glu Thr Gln Glu Tyr Arg Leu Tyr Arg Glu Lys
         50                    55                    60

AAA ACA GCA CCC TGG ATT ACA CGG ATC CCA CAG GAG CTT GTG AAG AAG    416
Lys Thr Ala Pro Trp Ile Thr Arg Ile Pro Gln Glu Leu Val Lys Lys
 65                    70                    75                80

GGC CAG TTC CCC ATC CCA TCC ATC ACC TGG GAA CAT GCA GGG CGG TAT    464
Gly Gln Phe Pro Ile Pro Ser Ile Thr Trp Glu His Ala Gly Arg Tyr
                     85                    90                    95

CGC TGT TAC TAT GGT AGC GAC ACT GCA GGC CGC TCA GAG AGC AGT GAC    512
Arg Cys Tyr Tyr Gly Ser Asp Thr Ala Gly Arg Ser Glu Ser Ser Asp
                100                   105                   110

CCC CTG GAG CTG GTG GTG ACA GGA GCC TAC ATC AAA CCC ACC CTC TCA    560
Pro Leu Glu Leu Val Val Thr Gly Ala Tyr Ile Lys Pro Thr Leu Ser
             115                   120                   125

GCC CAG CCC AGC CCC GTG GTG AAC TCA GGA GGG AAT GTA ACC CTC CAG    608
Ala Gln Pro Ser Pro Val Val Asn Ser Gly Gly Asn Val Thr Leu Gln
         130                   135                   140

TGT GAC TCA CAG GTG GCA TTT GAT GGC TTC ATT CTG TGT AAG GAA GGA    656
Cys Asp Ser Gln Val Ala Phe Asp Cly Phe Ile Leu Cys Lys Glu Gly
145                   150                   155                   160

GAA GAT GAA CAC CCA CAA TGC CTG AAC TCC CAG CCC CAT GCC CGT GGG    704
Glu Asp Glu His Pro Gln Cys Leu Asn Ser Gln Pro His Ala Arg Gly
                 165                   170                   175

TCG TCC CGC GCC ATC TTC TCC GTG GGC CCC GTG AGC CCG AGT CGC AGG    752
Ser Ser Arg Ala Ile Phe Ser Val Gly Pro Val Ser Pro Ser Arg Arg
             180                   185                   190

TGG TGG TAC ACC TGC TAT GCT TAT GAC TCG AAC TCT CCC TAT GAG TGG    800
Trp Trp Tyr Arg Cys Tyr Ala Tyr Asp Ser Asn Ser Pro Tyr Glu Trp
         195                   200                   205

TCT CTA CCC AGT GAT CTC CTG GAG CTC CTG GTC CTA GGT GTT TCT AAG    848
Ser Leu Pro Ser Asp Leu Leu Glu Leu Leu Val Leu Gly Val Ser Lys
     210                   215                   220

AAG CCA TCA CTC TCA GTG CAG CCA GGT CCT ATC GTG CCC CCT GAG GAG    896
Lys Pro Ser Leu Ser Val Gln Pro Gly Pro Ile Val Ala Pro Glu Glu
225                   230                   235                   240

ACC CTG ACT CTG CAG TGT GGC TCT GAT GCT GGC TAC AAC AGA TTT GTT    944
Thr Leu Thr Leu Gln Cys Gly Ser Asp Ala Gly Tyr Asn Arg Phe Val
                 245                   250                   255

CTG TAT AAG GAC GGG GAA CGT GAC TTC CTT CAG CTC GCT GGC GCA CAG    992
Leu Tyr Lys Asp Gly Glu Arg Asp Phe Leu Gln Leu Ala Gly Ala Gln
             260                   265                   270

CCC CAG GCT GGG CTC TCC CAG GCC AAC TTC ACC CTG GGC CCT GTG AGC   1040
Pro Gln Ala Gly Leu Ser Gln Ala Asn Phe Thr Leu Gly Pro Val Ser
         275                   280                   285

CGC TCC TAC GGG GGC CAG TAC AGA TGC TAC GGT GCA CAC AAC CTC TCC   1088
Arg Ser Tyr Gly Gly Gln Tyr Arg Cys Tyr Gly Ala His Asn Leu Ser
     290                   295                   300

TCC GAG TGG TCG GCC CCC AGC GAC CCC CTG GAC ATC CTG ATC GCA GGA   1136
Ser Glu Trp Ser Ala Pro Ser Asp Pro Leu Asp Ile Leu Ile Ala Gly
305                   310                   315                   320

CAG TTC TAT GAC AGA GTC TCC CTC TCG GTG CAG CCG GGC CCC ACG GTG   1184
Gln Phe Tyr Asp Arg Val Ser Leu Ser Val Gln Pro Gly Pro Thr Val
                 325                   330                   335

GCC TCA GGA GAG AAC GTG ACC CTG CTG TGT CAG TCA CAG GGA TGG ATG   1232
Ala Ser Gly Glu Asn Val Thr Leu Leu Cys Gln Ser Gln Gly Trp Met
             340                   345                   350

CAA ACT TTC CTT CTG ACC AAG GAG GGG GCA GCT GAT GAC CCA TGG CGT   1280
```

TABLE 3-continued

```
          Gln Thr Phe Leu Leu Thr Lys Glu Gly Ala Ala Asp Asp Pro Trp Arg
                      355                 360                 365

CTA AGA TCA ACG TAC CAA TCT CAA AAA TAC CAG GCT GAA TTC CCC ATG          1328
Leu Arg Ser Thr Tyr Gln Ser Gln Lys Tyr Gln Ala Glu Phe Pro Met
        370                 375                 380

GGT CCT GTG ACC TCA GCC CAT GCG GGG ACC TAC AGG TGC TAC GGC TCA          1376
Gly Pro Val Thr Ser Ala His Ala Gly Thr Tyr Arg Cys Tyr Gly Ser
385                 390                 395                 400

CAG AGC TCC AAA CCC TAC CTG CTC ACT CAC CCC ACT GAC CCC CTG GAG          1424
Gln Ser Ser Lys Pro Tyr Leu Leu Thr His Pro Ser Asp Pro Leu Glu
                405                 410                 415

CTC GTG GTC TCA GGA CCG TCT GGG GGC CCC AGC TCC CCG ACA ACA GGC          1472
Leu Val Val Ser Gly Pro Ser Gly Gly Pro Ser Ser Pro Thr Thr Gly
                    420                 425                 430

CCC ACC TCC ACA TCT GGC CCT GAG GAC CAG CCC CTC ACC CCC ACC CCC          1520
Pro Thr Ser Thr Ser Gly Pro Glu Asp Gln Pro Leu Thr Pro Thr Gly
                435                 440                 445

TCG GAT CCC CAG AGT GGT CTG GGA AGC CAC CTG GGG GTT GTG ATC GGC          1568
Ser Asp Pro Gln Ser Gly Leu Gly Arg His Leu Gly Val Val Ile Gly
        450                 455                 460

ATC TTG GTG GCC GTC ATC CTA CTG CTC CTC CTC CTC CTC CTC CTC TTC          1616
Ile Leu Val Ala Val Ile Leu Leu Leu Leu Leu Leu Leu Leu Leu Phe
465                 470                 475                 480

CTC ATC CTC CCA CAT CGA CGT CAG GCC AAA CAC TGG ACA TCG ACC CAG          1664
Leu Ile Leu Arg His Arg Arg Gln Cly Lys His Trp Thr Ser Thr Gln
                485                 490                 495

ACA AAG GCT GAT TTC CAA CAT CCT GCA GGG GCT GTC GGG CCA GAG CCC          1712
Arg Lys Ala Asp Phe Gln His Pro Ala Gly Ala Val Gly Pro Glu Pro
                500                 505                 510

ACA GAC AGA CGC CTG CAG TGG AGG TCC AGC CCA GCT GCC GAT GCC CAG          1760
Thr Asp Arg Arg Leu Gln Trp Arg Ser Ser Pro Ala Ala Asp Ala Gln
            515                 520                 525

GAA GAA AAC CTC TAT GCT GCC GTG AAG CAC ACA CAG CCT GAG GAT GGG          1808
Glu Glu Asn Leu Tyr Ala Ala Val Lys His Thr Gln Pro Glu Asp Gly
        530                 535                 540

GTG GAG ATG GAC ACT CGG CAG AGC CCA CAC GAT GAA GAC CCC CAG GCA          1856
Val Glu Met Asp Thr Arg Gln Ser Pro His Asp Glu Asp Pro Gln Ala
545                 550                 555                 560

GTG ACG TAT GCC GAG GTG AAA CAC TCC AGA CCT AGG AGA GAA ATG GCT          1904
Val Thr Tyr Ala Glu Val Lys His Ser Arg Pro Arg Arg Glu Met Ala
                565                 570                 575

TCT CCT CCT TCC CCA CTG TCT GGG GAA TTC CTG GAC ACA AAG GAC AGA          1952
Ser Pro Pro Ser Pro Leu Ser Gly Glu Phe Leu Asp Thr Lys Asp Arg
                580                 585                 590

CAG GCG GAA GAG GAC AGG CAG ATG GAC ACT GAG GCT GCT GCA TCT GAA          2000
Gln Ala Glu Glu Asp Arg Gln Met Asp Thr Glu Ala Ala Ala Ser Glu
            595                 600                 605

GCC CCC CAG GAT GTG ACC TAC GCC CAG CTG CAC AGC TTG ACC CTT AGA          2048
Ala Pro Gln Asp Val Thr Tyr Ala Gln Leu His Ser Leu Thr Leu Arg
        610                 615                 620

CGG AAG GCA ACT GAG CCT CCT CCA TCC CAG GAA GGG CCC TCT CCA GCT          2096
Arg Lys Ala Thr Glu Pro Pro Pro Ser Gln Glu Gly Pro Ser Pro Ala
625                 630                 635                 640

GTG CCC AGC ATC TAC GCC ACT CTG GCC ATC CAC TAG CCCAGGGGGG              2142
Val Pro Ser Ile Tyr Ala Thr Leu Ala Ile His *
                645                 650

GACGCAGACC CCACACTCCA TGGAGTCTGG AATGCATGGG AGCTGCCCCC CCAGTGGACA 2202

CCATTGGACC CCACCCAGCC TGGATCTACC CCAGGAGACT CTGGGAACTT TTAGGGGTCA 2262
```

TABLE 3-continued

```
CTCAATTCTG CAGTATAAAT AACTAATGTC TCTACAATTT TGAAATAAAG CAACAGACTT 2322

CTCAATAATC AATGAAGTAG CTGAGAAAAC TAAGTCAGAA AGTGCATTAA ACTGAATCAC 2382

AATGTAAATA TTACACATCA AGCGATGAAA CTGGAAAACT ACAAGCCACG AATGAATGAA 2442

TTAGGAAAGA AAAAAAGTAG GAAATGAATG ATCTTGGCTT TCCTATAAGA AATTTAGGGC 2502

AGGGCACGGT GGCTCACGCC TGTAATTCCA GCACTTTGGG AGGCCGAGGC GGGCAGATCA 2562

CGAGTTCAGG AGATCGAGAC CATCTTGGCC AACATGGTGA AACCCTGTCT CTCCTAAAAA 2622

TACAAAAATT AGCTGGATGT GGTGGCAGTG CCTGTAATCC CAGCTATTTG GGAGGCTGAG 2682

GCAGGAGAAT CGCTTGAACC AGGGAGTCAG AGGTTTCAGT GAGCCAAGAT CGCACCACTG 2742

CTCTCCAGCC TGGCGACAGA GGGAGACTCC ATCTCAAATT AAAAAAAA             2790
```

The peptide segments can also be used to produce appropriate oligonucleotides to screen a library to determine the presence of a similar gene, e.g., an identical or polymorphic variant, or to identify a monocyte. The genetic code can be used to select appropriate oligonucleotides useful as probes for screening. In combination with polymerase chain reaction (PCR) techniques, synthetic oligonucleotides will be useful in selecting desired clones from a library.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding these monocyte proteins, e.g., subcloning nucleic acid sequences encoding polypeptides into expression vectors, labeling probes, DNA hybridization, and the like are described generally in Sambrook, et al. (1989) *Molecular Cloning: A Laboratory Manual* (2nd ed.) Vol. 1–3, Cold Spring Harbor Laboratory, Cold Spring Harbor Press, NY, which is incorporated herein by reference and hereinafter referred to as "Sambrook, et al." See also, Coligan, et al. (1987 and periodic supplements) *Current Protocols in Molecular Biology* Greene/Wiley, New York, NY, referred to as "Coligan, et al."

There are various methods of isolating the DNA sequences encoding these monocyte proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed with other proteins and selecting specific primers. Such probes can be used directly in hybridization assays to isolate DNA encoding monocyte proteins, or probes can be designed for use in amplification techniques such as PCR, for the isolation of DNA encoding monocyte proteins.

To prepare a cDNA library, mRNA is isolated from cells which express the monocyte protein. cDNA is prepared from the mRNA and ligated into a recombinant vector. The vector is transfected into a recombinant host for propagation, screening and cloning. Methods for making and screening cDNA libraries are well known. See Gubler and Hoffman (1983) *Gene* 25:263–269; Sambrook, et al.; or Coligan, et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described, e.g., in Sambrook, et al. or Coligan, et al. Recombinant phage are analyzed by plaque hybridization as described in Benton and Davis (1977) *Science* 196:180–182. Colony hybridization is carried out as generally described in, e.g., Grunstein, et al. (1975) *Proc. Natl. Acad. Sci. USA* 72:3961–3965.

DNA encoding a monocyte protein can be identified in either cDNA or genomic libraries by its ability to hybridize with the nucleic acid probes described herein, for example in colony or plaque hybridization experiments. The corresponding DNA regions are isolated by standard methods familiar to those of skill in the art. See Sambrook, et al.

Various methods of amplifying target sequences, such as the polymerase chain reaction, can also be used to prepare DNA encoding monocyte proteins. Polymerase chain reaction (PCR) technology is used to amplify such nucleic acid sequences directly from mRNA, from cDNA, and from genomic libraries or cDNA libraries. The isolated sequences encoding monocyte proteins may also be used as templates for PCR amplification.

In PCR techniques, oligonucleotide primers complementary to two 5' regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a selected full-length monocyte protein or to amplify smaller DNA segments as desired. Once such regions are PCR-amplified, they can be sequenced and oligonucleotide probes can be prepared from sequence obtained using standard techniques. These probes can then be used to isolate DNAs encoding other forms of the monocyte proteins.

Oligonucleotides for use as probes are chemically synthesized according to the solid phase phosphoramidite triester method first described by Beaucage and Carruthers (1983) *Tetrahedron Lett.* 22(20):1859–1862, or using an automated synthesizer, as described in Needham-VanDevanter, et al. (1984) *Nucleic Acids Res.* 12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using the chemical degradation method of Maxam and Gilbert in Grossman and Moldave (eds.) (1980) *Methods in Enzymology* 65:499–560 Academic Press, New York.

An isolated nucleic acid encoding a human protein which is a type I transmembrane protein comprising an extracellular portion characterized by Ig-like domains, indicating that this gene encodes a receptor member of the Ig superfamily. This clone has been designated FDF03. Its nucleotide sequence and corresponding open reading frame are provided in SEQ ID NO: 1 and 2, respectively. An N-terminal hydrophobic sequence, e.g., a putative signal sequence, corresponds to about amino acid residues −19 (met) to −1(leu), and a internal hydrophobic segment, corresponding to a putative transmembrane segment runs from around ala177 to leu199. Other mammalian counterparts should become available, e.g., a partial rodent gene is described in SEQ ID NO: 3 and 4. Standard techniques will allow isolation of other counterparts, or to extend partial sequences.

A second human monocyte cell clone was isolated, designated YE01, is related to the receptors for Fc gamma and/or Fc alpha. This has also been referred to as DNAX Leukocyte Associated Immunoglobulin-like Receptor (DLAIR). See also Meyaard, et al. (1997) *Immunity* 7:283–290, which was published by the inventors after the priority date of this application, and is incorporated herein by reference. This protein is referred to herein as an Fc gamma/alpha receptor and is described in SEQ ID NO: 5 and 6. Another human isolate is described in SEQ ID NO: 7 and 8. A soluble form of the receptor is encoded in SEQ ID NO: 9 and 10. While the gene was initially described as a monocyte derived gene, expression analysis indicates that it is more specific for expression on lymphocytes. Thus, in the case of YE01, the descriptor "monocyte gene" may indicate its original identification in a population enriched for that cell type, though it may have also contained some other cell types. Sequence analysis suggests YE01 is a member of the Ig superfamily of receptors, and is closely related to the CD8 family, which contain a V1J -type fold, particularly the Fc receptors alpha and/or gamma. Because it contains an ITAM-like motif, the protein may well be a lymphocyte version of the Killer Inhibitory Receptors (KIR), which send a negative signal to inhibit killer cell function. This protein exhibits similar function in inhibiting lymphocyte effector function, e.g., antigen presentation or subsequent response initiation.

In particular, signaling through the molecule recognized by DX26 mAb (designated DNAX Leukocyte Associated Immunoglobulin-like Receptor (DLAIR)), delivers a negative signal to NK cell clones that prevents their killing specific target cells. However, the molecule is expressed on other lymphocytes, including T cells and monocytes. Thus, the DX26 antibody probably represents an antibody which both inhibits NK and cytotoxic T cell killing, and the monocyte distribution suggests that the molecule may inhibit monocyte-mediated or lymphocyte-mediated effector functions.

A third monocyte gene was isolated and designated KTE03, and is represented by six related embodiments, designated YYB01, YYB04 (forms 1 and 2), (KIR-Like Molecule) KLM63, KLM66, and KLM67. See SEQ ID NO: 11–22. Note that a possible splice variant, which may encode a variant protein form, has been detected.

This invention provides isolated DNA or fragments to encode a monocyte protein, as described. In addition, this invention provides isolated or recombinant DNA which encodes a biologically active protein or polypeptide which is capable of hybridizing under appropriate conditions, e.g., high stringency, with the DNA sequences described herein. Said biologically active protein or polypeptide can be a naturally occurring form, or a recombinant protein or fragment, and have an amino acid sequence as disclosed in SEQ ID NO: 2 or 4; 6, 8, or 10; or 12, 14, 16, 18, 20, or 22. Preferred embodiments will be full length natural isolates, e.g., from a primate. In glycosylated form, the proteins should exhibit larger sizes. Further, this invention encompasses the use of isolated or recombinant DNA, or fragments thereof, which encode proteins which are homologous to each respective monocyte protein. The isolated DNA can have the respective regulatory sequences in the 5' and 3' flanks, e.g., promoters, enhancers, poly-A addition signals, and others.

IV. Making Monocyte Gene Products

DNAs which encode these monocyte proteins or fragments thereof can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can, e.g., be used to generate polyclonal or monoclonal antibodies; for binding studies; for construction and expression of modified molecules; and for structure/function studies. Each of these monocyte proteins or their fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired monocyte gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode the various monocyte proteins, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a monocyte protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a monocyte gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express monocyte proteins or fragments include, but are not limited to, such vectors as those containing the lac promoter (pUC-series); trp promoter (pBR322-trp); Ipp promoter (the pIN-series); lambda-pp or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and Dictyostelium, may be transformed with monocyte gene sequence containing vectors. For purposes of this invention, the most common lower eukaryotic host is the baker's yeast, Saccharomyces cerevisiae. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the monocyte protein. In principle, most any higher eukaryotic tissue culture cell line may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

In certain instances, the monocyte proteins need not be glycosylated to elicit biological responses in certain assays. However, it will often be desirable to express a monocyte polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, a monocyte gene may be co-transformed with one or more genes encoding mammalian or other glycosylating enzymes. It is further understood that over glycosylation may be detrimental to monocyte protein biological activity, and that one of skill may perform routine testing to optimize the degree of glycosylation which confers optimal biological activity.

A monocyte protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; Brunner, et al. (1991) *J. Cell Biol.* 114:1275–1283; and Coligan, et al. (eds.) (1996 and periodic supplements) *Current Protocols in Protein Science*, John Wiley & Sons, New York, N.Y.

Now that these monocyte proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. See also Merrifield (1986) *Science* 232:341–347; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The monocyte proteins of this invention can be obtained in varying degrees of purity depending upon the desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and contacting the linked antibodies with solubilized lysates of appropriate source cells, lysates of other cells expressing the protein, or lysates or supernatants of cells producing the proteins as a result of DNA techniques, see below.

Multiple cell lines may be screened for one which expresses said protein at a high level compared with other cells. Various cell lines, e.g., a mouse thymic stromal cell line TA4, is screened and selected for its favorable handling properties. Natural monocyte cell proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features.

V. Antibodies

Antibodies can be raised to these various monocyte proteins, including individual, polymorphic, allelic, strain, or species variants, and fragments thereof, both in their naturally occurring (full-length) forms and in their recombinant forms. Additionally, antibodies can be raised to monocyte proteins in either their active forms or in their inactive forms. Anti-idiotypic antibodies may also be used.

a. Antibody Production

A number of immunogens may be used to produce antibodies specifically reactive with these monocyte proteins. Recombinant protein is the preferred immunogen for the production of monoclonal or polyclonal antibodies. Naturally occurring protein may also be used either in pure or impure form. Synthetic peptides made using the human monocyte protein sequences described herein may also used as an immunogen for the production of antibodies to the monocyte protein. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the monocyte protein of interest. When appropriately high titers of antibody to the immunogen are obtained, blood is collected from the animal and antisera are prepared. Further fractionation of the antisera to enrich for antibodies reactive to the protein can be done if desired. See, e.g., Harlow and Lane.

Monoclonal antibodies may be obtained by various techniques familiar to those skilled in the art. Briefly, spleen cells from an animal immunized with a desired antigen are immortalized, commonly by fusion with a myeloma cell. See, e.g., Kohler and Milstein (1976) *Eur. J. Immunol.* 6:511–519, which is incorporated herein by reference. Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Antibodies, including binding fragments and single chain versions, against predetermined fragments of these monocyte proteins can be raised by immunization of animals with conjugates of the fragments with carrier proteins as described above. Monoclonal antibodies are prepared from cells secreting the desired antibody. These antibodies can be screened for binding to normal or defective monocyte proteins, or screened for agonistic or antagonistic activity. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better. Standard methods are available for selection of high affinity and selective antibody preparations.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an inmunogen to initiate a humoral immune response. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752;

3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029–10033.

The antibodies of this invention can also be used for affinity chromatography in isolating each monocyte protein. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby purified monocyte protein will be released.

The antibodies may also be used to screen expression libraries for particular expression products. Usually the antibodies used in such a procedure will be labeled with a moiety allowing easy detection of presence of antigen by antibody binding.

Antibodies to monocyte proteins may be used for the analysis or, or identification of specific cell population components which express the respective protein. By assaying the expression products of cells expressing monocyte proteins it is possible to diagnose disease, e.g., immune-compromised conditions, monocyte depleted conditions, or overproduction of monocyte.

Antibodies raised against each monocyte will also be useful to raise anti-idiotypic antibodies. These will be useful in detecting or diagnosing various immunological conditions related to expression of the respective antigens.

b. Immunoassays

A particular protein can be measured by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; and Harlow and Lane *Antibodies, A Laboratory Manual,* supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.). (1988) *Non-isotopic Immunoassays* Plenum Press, NY.

Immunoassays for measurement of these monocyte proteins can be performed by a variety of methods known to those skilled in the art. In brief, immunoassays to measure the protein can be competitive or noncompetitive binding assays. In competitive binding assays, the sample to be analyzed competes with a labeled analyte for specific binding sites on a capture agent bound to a solid surface. Preferably the capture agent is an antibody specifically reactive with the monocyte protein produced as described above. The concentration of labeled analyte bound to the capture agent is inversely proportional to the amount of free analyte present in the sample.

In a competitive binding immunoassay, the monocyte protein present in the sample competes with labeled protein for binding to a specific binding agent, for example, an antibody specifically reactive with the monocyte protein. The binding agent may be bound to a solid surface to effect separation of bound labeled protein from the unbound labeled protein. Alternately, the competitive binding assay may be conducted in liquid phase and any of a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

These monocyte proteins may also be quantitatively determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of monocyte proteins in a sample. Electrophoresis is carried out, e.g., on a tissue sample suspected of containing the protein. Following electrophoresis to separate the proteins, and transfer of the proteins to a suitable solid support such as a nitrocellulose filter, the solid support is incubated with an antibody reactive with the denatured protein. This antibody may be labeled, or alternatively may be it may be detected by subsequent incubation with a second labeled antibody that binds the primary antibody.

The immunoassay formats described above employ labeled assay components. The label can be in a variety of forms. The label may be coupled directly or indirectly to the desired component of the assay according to methods well known in the art. A wide variety of labels may be used. The component may be labeled by any one of several methods. Traditionally a radioactive label incorporating $^3$H, $^{125}$I, $^{35}$S, $^{14}$C, or $^{32}$P is used. Non-radioactive labels include ligands which bind to labeled antibodies, fluorophores, chemiluminescent agents, enzymes, and antibodies which can serve as specific binding pair members for a labeled protein. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For reviews of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay,* supra; and Harlow and Lane *Antibodies, A Laboratory Manual,* supra.

A variety of different immunoassay formats, separation techniques, and labels can be also be used similar to those described above for the measurement of specific proteins. Moreover, many methods are known for evaluating selectivity of binding for specific protein or closely related proteins.

VI. Purified Monocyte Proteins

The human monocyte FDF03 protein amino acid sequence is provided in SEQ ID NO: 2. Partial mouse sequence is provided in SEQ ID NO: 4. Human YE01 amino acid and nucleotide sequences for the Ig-family member are provided in SEQ ID NO: 5–10. The receptor family members, designated KTE03, including the YYB01, YYB04, and KLM63, KLM66, and KLM67 embodiments, are described in SEQ ID NO: 11–22.

The peptide sequences allow preparation of peptides to generate antibodies to recognize such segments, and allow preparation of oligonucleotides which encode such sequences. Moreover, affinity reagents allow detection and purification of more protein, including full length or recombinant forms. And oligonucleotide sequences allow detection of cDNAs encoding, or closely related to, these.

VII. Physical Variants

This invention also encompasses proteins or peptides having substantial amino acid sequence similarity with an amino acid sequence of SEQ ID NO: 2 or 4; 6, 8, or 10; or 12, 14, 16, 18, 20, or 22, especially splice variants. Variants exhibiting substitutions, e.g., 20 or fewer, preferably 10 or fewer, and more preferably 5 or fewer substitutions, are also enabled. Where the substitutions are conservative substitutions, the variants will share immunogenic or antigenic similarity or cross-reactivity with a corresponding natural sequence protein. Natural variants include individual, allelic, polymorphic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural allelic and interspecies variations in each respective protein sequence. Typical homologous proteins or peptides will have from 50–100% similarity (if gaps can be introduced), to 75–100% similarity (if conservative substitutions are included) with the amino acid sequence of the relevant monocyte protein. Identity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) *Time Warps. String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group (GCG), Madison, Wis.

Nucleic acids encoding the corresponding mammalian monocyte proteins will typically hybridize, e.g., to SEQ ID NO 1 and/or 3; 5, 7, and/or 9; or 11, 13, 15, 17, 19, and/or 21 under stringent conditions. For example, nucleic acids encoding the respective monocyte proteins will typically hybridize to the appropriate nucleic acid under stringent hybridization conditions, while providing few false positive hybridization signals. Generally, stringent conditions are selected to be about 10° C. lower than the thermal melting point (Tm) for the sequence being hybridized to at a defined ionic strength and pH. The Tm is the temperature (under defined ionic strength and pH) at which 50% of the target sequence hybridizes to a perfectly matched probe. Typically, stringent conditions will be those in which the salt concentration in wash is about 0.02 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 20–50 mM NaCl at 42° C. In certain cases, the stringency may be relaxed to detect other nucleic acids exhibiting less than complete sequence identity.

An isolated monocyte gene DNA can be readily modified by nucleotide substitutions, nucleotide deletions, nucleotide insertions, and inversions of nucleotide stretches. These modifications result in novel DNA sequences which encode these monocyte antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant monocyte protein derivatives include predetermined or site-specific mutations of the respective protein or its fragments. "Mutant monocyte protein" encompasses a polypeptide otherwise falling within the homology definition of the monocyte protein as set forth above, but having an amino acid sequence which differs from that of the monocyte protein as found in nature, whether by way of deletion, substitution, or insertion. In particular, "site specific mutant monocyte protein" generally includes proteins having significant similarity with a protein having a sequence of SEQ ID NO: 2 or 4; 6, 8, or 10; or 12, 14, 16, 18, 20, or 22. Generally, the variant will share many physicochemical and biological activities, e.g., antigenic or immunogenic, with those sequences, and in preferred embodiments contain most or all of the disclosed sequence. Similar concepts apply to these various monocyte proteins, particularly those found in various warm blooded animals, e.g., primates and mammals.

Although site specific mutation sites are predetermined, mutants need not be site specific. Monocyte protein mutagenesis can be conducted by making amino acid insertions or deletions. Substitutions, deletions, insertions, or any combinations may be generated to arrive at a final construct. Insertions include amino- or carboxyl-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a respective monocyte polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, domains or other segments may be "swapped" between different new fusion polypeptides or fragments, typically with related proteins, e.g., within the Ig family or the Fc receptor family. Preferably, intact structural domains will be used, e.g., intact Ig portions. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains. Also, alanine scanning mutagenesis may be applied, preferably to residues which structurally are exterior to the secondary structure, which will avoid most of the critical residues which generally disrupt tertiary structure.

"Derivatives" of these monocyte antigens include amino acid sequence mutants, glycosylation variants, and covalent or aggregate conjugates with other chemical moieties. Covalent derivatives can be prepared by linkage of functionalities to groups which are found in these monocyte protein amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents. Also, proteins comprising substitutions are encompassed, which should retain substantial immunogenicity, to produce antibodies which recognize a protein of SEQ ID NO: 2 or 4; 6, 8, or 10; or 12, 14, 16, 18, 20, or 22. Alternatively, it may be desired to produce antibodies which recognize all or subsets of SEQ ID NO: 2 and 4; 6, 8, and 10; or 12, 14, 16, 18, 20, and 22. Typically, these proteins will contain less than 20 residue substitutions from the disclosed sequence, more typically less than 10 substitutions, preferably less than 5, and more preferably less than 3. Alternatively, proteins which begin and end at structural domains will usually retain antigenicity and cross immunogenicity.

A major group of derivatives are covalent conjugates of the monocyte proteins or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between these monocyte proteins and other homologous or heterologous proteins are also provided. Heterologous polypeptides may be fusions between different surface markers, resulting in, e.g., a hybrid protein. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of these monocyte proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a monocyte protein antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-monocyte protein antibodies. The monocyte proteins can also be labeled with a detectable group, e.g., radioiodinated by the chloramine T procedure, covalently bound to rare earth chelates, or conjugated to another fluorescent moiety for use in diagnostic assays. Purification of these monocyte proteins may be effected by immobilized antibodies.

Isolated monocyte protein genes will allow transformation of cells lacking expression of a corresponding monocyte protein, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of these monocyte proteins. Subcellular fragments, e.g., cytoplasts or membrane fragments, can be isolated and used.

VIII. Binding Agent:Monocyte Protein Complexes

A monocyte protein that specifically binds to or that is specifically immunoreactive with an antibody generated against a defined immunogen, such as an immunogen consisting of the amino acid sequence of SEQ ID NO: 2 and/or 4; 6, 8, and/or 10; or 12, 14, 16, 18, 20, and/or 22, is determined in an immunoassay. The immunoassay uses a polyclonal antiserum which was raised to the protein of SEQ ID NO: 2, 4, 6, 8, 10, 12, 14, 16, 18, 20, or 22, or appropriate combination. This antiserum is selected to have low cross-reactivity against other members of the related families, and any such crossreactivity is, or may be, removed by immunoabsorption prior to use in the immunoassay.

In order to produce antisera for use in an immunoassay, the protein of SEQ ID NO: 2, 4, 6, 8, 10, 12, 14, 16, 18, 20, or 22 is isolated as described herein. For example, recombinant protein may be produced in a mammalian cell line. An inbred strain of mice such as Balb/c is immunized with the appropriate protein using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other related proteins, using a competitive binding immunoassay such as the one described in Harlow and Lane, supra, at pages 570–573. See also Hertzenberg, et al. (eds. 1996) *Weir's Handbook of Experimental Immunology* vols. 1–4, Blackwell Science; and Coligan (1991) *Current Protocols in Immunology* Wiley/Greene, NY. Preferably two different related proteins are used in this determination in conjunction with a given monocyte protein. For example, with the Ig family protein, at least two other family members are used to absorb out shared epitopes. In conjunction with the Fc family member, two other members of the family are used. These other family members can be produced as recombinant proteins and isolated using standard molecular biology and protein chemistry techniques as described herein.

Immunoassays in the competitive binding format can be used for the crossreactivity determinations. For example, the protein can be immobilized to a solid support. Proteins added to the assay compete with the binding of the antisera to the immobilized antigen. The ability of the above proteins to compete with the binding of the antisera to the immobilized protein is compared to the protein of SEQ ID NO 2 and/or 4; 6, 8, and/or 10; or 12, 14, 16, 18, 20, and/or 22. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein, e.g., the monocyte protein of SEQ ID NO: 2, 4, 6, 8, 10, 12, 14, 16, 18, 20, or 22. In order to make this comparison, the two proteins are each assayed at a wide range of concentrations and the amount of each protein required to inhibit 50% of the binding of the antisera to the immobilized protein is determined. If the amount of the second protein required is less than twice the amount of the protein, e.g., of SEQ ID NO: 2, that is required, then the second protein is said to specifically bind to an antibody generated to the immunogen.

It is understood that monocyte proteins are each a family of homologous proteins that comprise two or more genes. For a particular gene product, such as the human Ig family member protein, the invention encompasses not only the amino acid sequences disclosed herein, but also to other proteins that are allelic, polymorphic, non-allelic, or species variants. It is also understood that the term "human monocyte protein" includes nonnatural mutations introduced by deliberate mutation using conventional recombinant technology such as single site mutation, or by excising short sections of DNA encoding these proteins or splice variants from the gene, or by substituting or adding small numbers of new amino acids. Such minor alterations must substantially maintain the immunoidentity of the original molecule and/or its biological activity. Thus, these alterations include proteins that are specifically immunoreactive with a designated naturally occurring respective monocyte protein, for example, the human monocyte protein exhibiting SEQ ID NO: 4. Particular protein modifications considered minor would include conservative substitution of amino acids with similar chemical properties, as described above for each protein family as a whole. By aligning a protein optimally with the protein of SEQ ID NO 2 and 4; 6, 8, and 10; or 12, 14, 16, 18, 20, and 22, and by using the conventional immunoassays described herein to determine immunoidentity, one can determine the protein compositions of the invention.

IX. Uses

The present invention provides reagents which will find use in diagnostic applications as described elsewhere herein, e.g., in the general description for developmental abnormalities, or below in the description of kits for diagnosis.

Monocyte genes, e.g., DNA or RNA may be used as a component in a forensic assay. For instance, the nucleotide sequences provided may be labeled using, e.g., 32P or biotin and used to probe standard restriction fragment polymorphism blots, providing a measurable character to aid in distinguishing between individuals. Such probes may be used in well-known forensic techniques such as genetic fingerprinting. In addition, nucleotide probes made from monocyte sequences may be used in in situ assays to detect chromosomal abnormalities.

Antibodies and other binding agents directed towards monocyte proteins or nucleic acids may be used to purify the corresponding monocyte protein molecule. As described in the Examples below, antibody purification of monocyte proteins is both possible and practicable. Antibodies and other binding agents may also be used in a diagnostic fashion to determine whether monocyte components are present in a tissue sample or cell population using well-known techniques described herein. The ability to attach a binding agent to a monocyte protein provides a means to diagnose disorders associated with expression misregulation. Antibodies and other monocyte protein binding agents may also be useful as histological markers. As described in the examples below, the expression of each of these proteins is limited to specific tissue types. By directing a probe, such as an antibody or nucleic acid to the respective monocyte protein, it is possible to use the probe to distinguish tissue and cell types in situ or in vitro.

This invention also provides reagents which may exhibit significant therapeutic value. The monocyte proteins (naturally occurring or recombinant), fragments thereof, and antibodies thereto, along with compounds identified as having binding affinity to the monocyte protein, may be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a monocyte, e.g., as an antigen presenting cell, is a target for an agonist or antagonist of the protein. The proteins likely play a role in regulation or development of hematopoietic cells, e.g., lymphoid cells, which affect immunological responses, e.g., antigen presentation and the resulting effector functions.

For example, the DX26 antibody shows that inhibitory antibodies will be useful in modulating NK or T cell functions, e.g., killing. Such modulation will typically be a 20% effect, either increasing or decreasing, e.g., the killing effect, but in preferred embodiments will have a 30%, 40%, 50%, or more. Because the distribution is also in monocytes, the molecule will probably also affect the regulation of monocyte mediated or initiated effector functions of the immune system, e.g., autoimmune responses, transplantation rejection, graft vs. host disease, inflammatory conditions, etc. These molecules may also affect elimination of neoplastic conditions, e.g., tumor rejection.

Other abnormal developmental conditions are known in cell types shown to possess monocyte protein mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, NY. Developmental or functional abnormalities, e.g., of the immune system, cause significant medical abnormalities and conditions which may be susceptible to prevention or treatment using compositions provided herein.

Recombinant monocyte proteins or antibodies might be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. In particular, these may be useful in a vaccine context, where the antigen is combined with one of these therapeutic versions of agonists or antagonists. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to these monocyte proteins, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity might activate the cell through the protein and is thus an agonist in that it simulates the cell. This invention further contemplates the therapeutic use of antibodies to the proteins as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 $\mu$M (picomolar), and most preferably less than about 1 fM (femtomolar), with an appropriate carrier. Slow release formulations, or a slow release apparatus will often be utilized for continuous administration.

The monocyte proteins, fragments thereof, and antibodies to it or its fragments, antagonists, and agonists, could be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, NY.; Lieberman, et al. (eds.) (1990) *Pharmaceutical Dosage Forms: Tablets* Dekker, NY.; and Lieberman, et al. (eds.) (1990) *Pharmaceutical Dosage Forms: Disperse Systems* Dekker, NY. The therapy of this invention may be combined with or used in association with other chemotherapeutic or chemopreventive agents.

Both the naturally occurring and the recombinant form of the monocyte proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, e.g., soluble versions of, monocyte protein as provided by this invention.

For example, antagonists can often be found once the protein has been structurally defined. Testing of potential protein analogs is now possible upon the development of highly automated assay methods using a purified surface protein. In particular, new agonists and antagonists will be discovered by using screening techniques described herein. Of particular importance are compounds found to have a combined binding affinity for multiple related cell surface antigens, e.g., compounds which can serve as antagonists for species variants of a monocyte protein.

This invention is particularly useful for screening compounds by using recombinant monocyte protein in a variety of drug screening techniques. The advantages of using a recombinant protein in screening for specific ligands include: (a) improved renewable source of the protein from a specific source; (b) potentially greater number of antigens per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a monocyte protein. Cells may be isolated which express that protein in isolation from any others. Such cells, either in viable or fixed form, can be used for standard surface protein binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of monocyte protein) are contacted and incubated with an antibody having known binding affinity to the antigen, such as $^{125}$I-antibody, and a test sample whose binding affinity to the binding composition is being measured. The bound and free labeled binding compositions are then separated to assess the degree of protein binding. The amount of test compound bound is inversely proportional to the amount of labeled antibody binding to the known source. Many techniques can be used to separate bound from free reagent to assess the degree of binding. This separation step could typically involve a procedure such as adhesion to filters followed by washing, adhesion to plastic followed by washing, or centrifugation of the cell membranes. Viable cells could also be used to screen for the effects of drugs on these monocyte protein mediated functions, e.g., antigen presentation or helper function.

Another method utilizes membranes from transformed eukaryotic or prokaryotic host cells as the source of a monocyte protein. These cells are stably transformed with DNA vectors directing the expression of the appropriate protein, e.g., an engineered membrane bound form. Essentially, the membranes would be prepared from the cells and used in binding assays such as the competitive assay set forth above.

Still another approach is to use solubilized, unpurified or solubilized, purified monocyte protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to the respective monocyte protein and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified monocyte protein, and washed. The next step involves detecting bound reagent, e.g., antibody.

One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

X. Kits

This invention also contemplates use of these monocyte proteins, fragments thereof, peptides, and their fusion products in a variety of diagnostic kits and methods for detecting the presence of a monocyte protein or message. Typically the kit will have a compartment containing either a defined monocyte peptide or gene segment or a reagent which recognizes one or the other, e.g., antibodies.

A kit for determining the binding affinity of a test compound to the respective monocyte protein would typically comprise a test compound; a labeled compound, for example an antibody having known binding affinity for the protein; a source of the monocyte protein (naturally occurring or recombinant); and a means for separating bound from free labeled compound, such as a solid phase for immobilizing the monocyte protein. Once compounds are screened, those having suitable binding affinity to the protein can be evaluated in suitable biological assays, as are well known in the art, to determine whether they act as agonists or antagonists to regulate monocyte function. The availability of recombinant monocyte polypeptides also provide well defined standards for calibrating such assays.

A preferred kit for determining the concentration of, for example, a monocyte protein in a sample would typically comprise a labeled compound, e.g., antibody, having known binding affinity for the monocyte protein, a source of monocyte protein (naturally occurring or recombinant) and a means for separating the bound from free labeled compound, for example, a solid phase for immobilizing the monocyte protein. Compartments containing reagents, and instructions, will normally be provided.

Antibodies, including antigen binding fragments, specific for the respective monocyte or its fragments are useful in diagnostic applications to detect the presence of elevated levels of the protein and/or its fragments. Such diagnostic assays can employ lysates, live cells, fixed cells, immunofluorescence, cell cultures, body fluids, and further can involve the detection of antigens in serum, or the like. Diagnostic assays may be homogeneous (without a separation step between free reagent and antigen-monocyte protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to the monocyte protein or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY. In particular, the reagents may be useful for diagnosing monocyte populations in biological samples, either to detect an excess or deficiency of monocyte in a sample. The assay may be directed to histological analysis of a biopsy, or evaluation of monocyte numbers in a blood or tissue sample.

Anti-idiotypic antibodies may have similar use to diagnose presence of antibodies against a monocyte protein, as such may be diagnostic of various abnormal states. For example, overproduction of the monocyte protein may result in various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled monocyte protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In many of these assays, the protein, test compound, monocyte protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free protein, or alternatively the bound from the free test compound. The monocyte protein can be immobilized on various matrices followed by washing. Suitable matrices include plastic such as an ELISA plate, filters, and beads. Methods of immobilizing the monocyte protein to a matrix include, without limitation, direct adhesion to plastic, use of a capture antibody, chemical coupling, and biotin-avidin. The last step in this approach involves the precipitation of protein/antibody complex by one of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a respective monocyte protein. These sequences can be used as probes for detecting levels of the message in samples from patients suspected of having an abnormal condition, e.g., cancer or immune problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XI. Binding Partner Isolation

Having isolated one member of a binding partner of a specific interaction, methods exist for isolating the counter-partner. See, Gearing, et al. (1989) *EMBO J.* 8:3667–3676. For example, means to label a monocyte surface protein without interfering with the binding to its receptor can be determined. For example, an affinity label can be fused to either the amino- or carboxyl-terminus of the ligand. An expression library can be screened for specific binding to the monocyte protein, e.g., by cell sorting, or other screening to detect subpopulations which express such a binding component. See, e.g., Ho, et al. (1993) *Proc. Nat'l Acad. Sci. USA* 90:11267–11271. Alternatively, a panning method may be used. See, e.g., Seed and Aruffo (1987) *Proc. Nat'l Acad. Sci. USA* 84:3365–3369. A two-hybrid selection system may also be applied making appropriate constructs with the available monocyte protein sequences. See, e.g., Fields and Song (1989) *Nature* 340:245–246.

Protein cross-linking techniques with label can be applied to isolate binding partners of a monocyte protein. This would allow identification of proteins which specifically interact with the appropriate monocyte protein.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Clonina: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY.

Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1996 and periodic Supplements) *Current Protocols in Protein Science* Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *OIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163. See also, e.g., Paul (ed.) (1993) *Fundamental Immunology* (3d ed.) Raven Press, N.Y.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of Human Monocytes

Healthy donors were subjected to a leukophoresis. Percoll gradients were used to isolate mononuclear cells which were then subject to centrifugal elutriation. See, Figdor, et al. (1982) *Blood* 60:46–53; and Plas, et al. (1988) *Expt'l, Hematol.* 16:355–359. This highly enriched monocyte fraction was cultured for 5–7 days in the presence of GM-CSF (800 U/ml) and IL-4 (500 U/ml), as described in Romani, et al (1994) *J. Exp. Med.* 180:83–93; and Sallusto, et al (1994) *J. Exp. Med.* 179:1109–1118.

For making dendritic cells, human CD34+ cells were obtained as follows. See, e.g., Caux, et al. (1995) pages 1–5 in Banchereau and Schmitt *Dendritic Cells in Fundamental and Clinical Immunology* Plenum Press, NY. Peripheral or cord blood cells, sometimes CD34+ selected, were cultured in the presence of Stem Cell Factor (SCF), GM-CSF, and TNF-α in endotoxin free RPMI 1640 medium (GIBCO, Grand Island, N.Y.) supplemented with 10% (v/v) heat-inactivated fetal bovine serum (FBS; Flow Laboratories, Irvine, Calif.), 10 mM HEPES, 2 mM L-glutamine, $5 \times 10^{-5}$ M 2-mercaptoethanol, penicillin (100 µg/ml). This is referred to as complete medium.

CD34+ cells were seeded for expansion in 25 to 75 $cm^2$ flasks (Corning, N.Y.) at $2 \times 10^4$ cells/ml. Optimal conditions were maintained by splitting these cultures at day 5 and 10 with medium containing fresh GM-CSF and TNF-α (cell concentration: $1-3 \times 10^5$ cells/ml). In certain cases, cells were FACS sorted for CD1a expression at about day 6.

In certain situations, cells were routinely collected 5 after 12 days of culture, eventually adherent cells were recovered using a 5 mM EDTA solution. In other situations, the CD1a+ cells were activated by resuspension in complete. medium at $5 \times 10^6$ cells/ml and activated for the appropriate time (e.g., 1 or 6 h) with 1 µg/ml phorbol 12-myristate 13-acetate (PMA, Sigma) and 100 ng/ml ionomycin (Calbiochem, La Jolla, Calif.). These cells were expanded for another 6 days, and RNA isolated for cDNA library preparation.

III. RNA isolation and library construction

Total RNA is isolated using, e.g., the guanidine thiocyanate/CsCl gradient procedure as described by Chirgwin, et al. (1978) *Biochem.* 18:5294–5299.

Alternatively, poly(A)+ RNA is isolated using the OLIGOTEX mRNA isolation kit (QIAGEN). Double stranded cDNA are generated using, e.g., the SUPERSCRIPT plasmid system (Gibco BRL, Gaithersburg, Md.) for cDNA synthesis and plasmid cloning. The resulting double stranded cDNA is unidirectionally cloned, e.g., into pSport1 and transfected by electroporation into ELECTROMAX DH10BTM Cells (Gibco BRL, Gaithersburg, Md.).

IV. Sequencing

DNA isolated from randomly picked clones, or after subtractive hybridization using unactivated cells, were subjected to nucleotide sequence analysis using standard techniques. A Taq DiDeoxy Terminator cycle sequencing kit. (Applied Biosystems, Foster City, Calif.) can be used. The labeled DNA fragments are separated using a DNA sequencing gel of an appropriate automated sequencer. Alternatively, the isolated clone is sequenced as described, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York. Chemical sequencing methods are also available, e.g., using Maxam and Gilbert sequencing techniques.

V. Isolation of Human Monocyte Protein Genes The FDF03, the YE01, and KTE03 (YYB01 and YYB04) clones were sequenced, and analyzed for open reading frames. The clones were further analyzed to extend the nucleic acid sequence to a full, or nearly full, open reading frame.

mRNA is prepared from appropriate cell populations by the FASTTRACK kit (Invitrogen, Carlsbad, Calif.) from which cDNA is generated using, e.g., SUPERSCRIPT Plasmid System for cDNA synthesis from GIBCO-BRL (Gaithersburg, Md.) essentially as described by the manufacturer. Modification to the procedure may include the substitution of other cloning adapters for the Sal1 adapters provided with the kit. The resultant cDNA from these cells is used to generate libraries, e.g., in the plasmid PCDNA II (Invitrogen, Carlsbad, Calif.). The cDNA is cloned into the polylinker and is used to transform an appropriate strain, e.g., DH10B, of *E. coli.* Plasmid is isolated and purified, e.g., with the QIAGEN system (Qiagen, Inc., Chatsworth, Calif.) which is used to generate RNA probes from, e.g., the SP6 promoter.

RNA probes are labeled, e.g., using the GENIUS SYSTEM (Boehringer-Mannheim, Indianapolis, Ind.) as described by the manufacturer. Filter lifts of the cDNA library can be pre-hybridized, e.g., at 42° C. for 3–6 hours in Church's buffer (50% formamide, 6×SSPE, 50 mM $NaHPO_4$ pH 7.2, 7% SDS, 0.1% N-Lauryl sarcosine, 2% Boehringer-Mannheim blocking reagent). Filters are probed, e.g., overnight in the same buffer containing the appropriate probes. The filters are washed, e.g., as described by the GENIUS SYSTEM. The colonies that hybridize are selected.

The entire cDNA of human monocyte proteins are sequenced, e.g., by the dideoxynucleotide chain termination method with T7 polymerase (U.S. Biochemicals, Cleveland, Ohio) using double-stranded DNA as template. Data base searching and sequence analysis are performed using IntelliGenetics programs (Mountain View, Calif.) to determine if homology exists between previously reported clones.

Table 1 discloses sequence encoding a human FDF03 gene and mouse counterpart sequence, and also shows alignment of available sequence. Likewise, Table 2 discloses three sequences encoding human YE01 gene products, including a splice variant and a transcript which encodes a soluble product. Table 3 provides sequences of embodiments of the KTE03 gene products, and shows evidence of splice variants.

VI. Recombinant Monocyte Gene Constructs

Poly(A)$^+$ RNA is isolated from appropriate cell populations, e.g., using the FASTTRACK mRNA kit (Invitrogen, Carlsbad, Calif.). Samples are electrophoresed, e.g., in a 1% agarose gel containing formaldehyde and transferred to a GENESCREEN membrane (NEN Research Products, Boston, Mass.). Hybridization is performed, e.g., at 65° C. in 0.5 M NaHPO$_4$ pH 7.2, 7% SDS, 1 mM EDTA, and 1% BSA (fraction V) with $^{32}$P-dCTP labeled monocyte gene cDNA at $10^7$ cpm/ml. After hybridization filters are washed three times at 50° C. in 0.2×SSC, 0.1% SDS, and exposed to film for 24 h.

The recombinant gene construct may be used to generate probe for detecting the message. The insert may be excised and used in the detection methods described above.

VII. Expression of Monocyte Gene Protein in *E. coli*

PCR is used to make a construct comprising the open reading frame, preferably in operable association with proper promoter, selection, and regulatory sequences. The resulting expression plasmid is transformed into an appropriate, e.g., the TOPP5, *E. coli* strain (Stratagene, La Jolla, Calif.). Ampicillin resistant (50 µg/ml) transformants are grown in Luria Broth (Gibco, Rockville, Md.) at 37° C. until the optical density at 550 nm is 0.7. Recombinant protein is induced with 0.4 mM isopropyl-βD-thiogalactopyranoside (Sigma, St. Louis, Mo.) and incubation of the cells continued at 20° C. for a further 18 hours. Cells from a 1 liter culture are harvested by centrifugation and resuspended, e.g., in 200 ml of ice cold 30% sucrose, 50 mM Tris HCl pH 8.0, 1 mM ethylenediamine-tetraacetic acid. After 10 min on ice, ice cold water is added to a total volume of 2 liters. After 20 min on ice, cells are removed by centrifugation and the supernatant is clarified by filtration via a 5 µM MILLIPAK 60 (Millipore Corp., Bedford, Mass.).

The recombinant protein is purified via standard purification methods, e.g., various ion exchange chromatography methods. Immunoaffinity methods using antibodies described below can also be used. Affinity methods may be used where an epitope tag is engineered into an expression construct.

VIII. Mapping of human monocyte genes

DNA isolation, restriction enzyme digestion, agarose gel electrophoresis, Southern blot transfer and hybridization are performed according to standard techniques. See Jenkins, et al. (1982) *J. Virol.* 43:26–36. Blots may be prepared with HYBOND-N nylon membrane (Amersham, Piscataway, N.J.). The probe is labeled with $^{32}$P-dCTP; washing is done to a final stringency, e.g., of 0.1×SSC, 0.1% SDS, 65° C.

Alternatively, a BIOS Laboratories (New Haven, Conn.) mouse somatic cell hybrid panel may be combined with PCR methods.

IX. Analysis of Individual Variation

From the distribution data, an abundant easily accessible cell type is selected for sampling from individuals. Using PCR techniques, a large population of individuals are analyzed for this gene. cDNA or other PCR methods are used to sequence the corresponding gene in the different individuals, and their sequences are compared. This indicates both the extent of divergence among racial or other populations, as well as determining which residues are likely to be modifiable without dramatic effects on function.

X. Preparation of Antibodies

Recombinant monocyte proteins are generated by expression in *E. coli* as shown above, and tested for biological activity. Active or denatured proteins may be used for immunization of appropriate mammals for either polyclonal serum production, or for monoclonal antibody production. Antibodies are selected for use in Western blots, against native or denatured antigen, and for those which modulate a biological activity.

Antibodies prepared against the FDF03 have confirmed specific binding on dendritic cells.

XI. Isolation of Counterpart Primate Monocyte Genes

Human cDNA clones encoding these genes are used as probes, or to design PCR primers to find counterparts in various primate species, e.g., chimpanzees.

XII. Use of reagents to analyze cell populations

Detection of the level of monocyte cells present in a sample is important for diagnosis of certain aberrant disease conditions. For example, an increase in the number of monocytes in a tissue or the lymph system can be indicative of the presence of a monocyte hyperplasia, tissue or graft rejection, or inflammation. A low monocyte population can indicate an abnormal reaction to, e.g., a bacterial or viral infection, which may require the appropriate treat to normalize the monocyte response.

FACS analysis using a labeled binding agent specific for a cell surface monocyte protein, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y., is used in determining the number of monocytes present in a cell mixture, e.g., PBMCs, adherent cells, etc. The binding agent is also used for histological analysis of tissue samples, either fresh or fixed, to analyze infiltration of monocyte. Diverse cell populations may also be evaluated, either in a cell destructive assay, or in certain assays where cells retain viability.

Analysis of the presence of soluble intracellular molecules is performed, e.g., with a fluorescent binding agent specific for a monocyte as described in Openshaw, et al. (1995) *J. Exp. Med.* 182:1357–1367. alternatively, tissue or cell fixation methods may be used.

Levels of monocyte transcripts are quantitated, e.g., using semiquantitative PCR as described in Murphy, et al. (1993) *J. Immunol. Methods* 162:211–223. Primers are designed such that genomic DNA is not detected.

Distribution of the FDF03 embodiment has been studied using hybridization and PCR analysis. Northern blot analysis located transcripts in dendritic cells and the JY cell line. There appear to be two transcripts of about 700 bp and 1300 bp, which may be differentially regulated, and an estimated frequency of about 1 in 4000 in resting monocytes or LPS and IFNy activated monocytes. The shorter message does not appear to encode a soluble version of the protein, e.g., lacking the TM and intracellular segments. Southern blot analysis has detected transcripts in monocytes, dendritic cells, PBMC, B cells, and splenic B cells. The message appears to be down-regulated upon monocyte activation.

Distribution of the YE01 embodiment has also been evaluated. The message appears to be monocyte specific, and is a low abundance message. It is detectable in cDNA Southern blots in resting monocytes, and in activated monocytes. Its highest expression was found in 6 hour LPS stimulated monocytes. It is also detectable in anti-CD3 and PMA activated PBMC. It may be faintly detectable in dendritic cells, but this may be due to contamination of the dendritic cell population with residual monocytes. At that level of sensitivity, it is undetectable in NK cells, B or T cells, or any fetal cells examined. However, the YE01 gene product is specifically recognized by a monoclonal antibody DX26. This antibody, when crosslinked, can inhibit NK cell mediated killing of certain targets. The antibody recognizes protein expressed in T cells, B cells, NK cells, and monocytes. The gene encoding the antigen recognized by DX26, which is apparently a polymorphic variant of the YE01 isolate, has been cloned and has essentially the sequence:

The KTE03 expression levels were also investigated. The message appeared to be up-regulated upon IL-10 exposure when the monocytes were activated by LPS and IFNγ.

XIII. Isolation of a Binding Counterpart

A monocyte protein can be used as a specific binding reagent, by taking advantage of its specificity of binding, much like an antibody would be used. A binding reagent is either labeled as described above, e.g., fluorescence or otherwise, or immobilized to a substrate for panning methods.

The monocyte protein is used to screen for a cell line which exhibits binding. Standard staining techniques are used to detect or sort intracellular or surface expressed ligand, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3\times10^5$ cells per chamber in 1.5 ml of growth media. Incubate overnight at 37° C.

On day 1 for each sample, prepare 0.5 ml of a solution of 66 mg/ml DEAE-dextran, 66 mM chloroquine, and 4 mg DNA in serum free DME. For each set, a positive control is prepared, e.g., of human receptor-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin(0.1%) with 32 ml/ml of 1M $NaN_3$ for 20 min. Cells are then washed with HBSS/saponin 1×. Add protein or protein/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90 C.

Alternatively, other monocyte protein specific binding reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a monocyte protein fusion construct, or by use of antibodies raised against the first antibodies. Recursive cycles of selection and amplification lead to enrichment of appropriate clones and eventual isolation of ligand expressing clones.

Phage expression libraries can be screened by monocyte protein. Appropriate label techniques, e.g., anti-FLAG antibodies, will allow specific labeling of appropriate clones.

XIV. Isolation of a Soluble YE01

An additional family member of the previously described YE01, also designated DNAX Leukocyte Associated Immunoglobulin-like Receptor (DLAIR; and now designated DLAIR-1) was cloned by screening a human T cell tumor line cDNA library (TcT). Bacterial colony lift membranes were hybridized with a DLAIR-1 probe comprising a BglII-SphI digestion fragment, spanning the Ig loop in the extracellular domain. Two positives were isolated and sequenced. Sequence analysis revealed that both clones contained identical open reading frames of 414 base pairs, encoding a 135 amino acid protein with a predicted 21 amino acid leader sequence and a predicted molecular weight of 14.7 kDa. This molecule, now referred to as DLAIR-2, contains one Ig loop. See Table 2. The Ig loop has 84% homology with DLAIR-1, indicating that it belongs to the same family, but is encoded by a separate gene. DLAIR-2 lacks a transmembrane region which suggests that it is a secreted protein.

DLAIR-2, as a soluble molecule with similarity to DLAIR-1, may be used as an antagonist to this inhibitory receptor.

XV. Preparation of DX26 Monoclonal Antibody

Mice were immunized with a human NK cell clone and antibodies were screened for their capacity to inhibit NK cell-mediated lysis of FcR bearing targets. Alternatively, antibodies will be raised to purified protein.

XVI. Cross-linking DLAIR-1 with mAb Inhibits NK Cell-mediated Killing

DX26 mAb did not inhibit NK clone killing of the HLA-negative EBV-transformed B cell line 721.221. However, when 721.221 was transfected with the human FcγR-II (CD32) and used as a target, NK cell-mediated cytolysis was inhibited by DX26 mAb. This indicates that signaling through the molecule recognized by DX26 mAb (designated DNAX Leukocyte Associated Immunoglobulin-like Receptor (DLAIR)), delivers a negative signal to NK cell clones that prevents their killing specific target cells. In agreement with this, NK cell-mediated cytotoxicity against Colo-205, PA-1, or FO-1, each an FcR-negative human cell line, was not inhibited by the addition of DX26 mAb. Moreover, lysis of P815 cells, an FcR-expressing mouse mastocytoma cell line, which is killed in vitro by human NK cell clones upon simultaneous cross linking of CD2, CD16, CD69, or DNAM-1 antigen, was also inhibited by DX26 mAb. These results lead to a conclusion that DLAIR delivers a strong inhibitory signal to NK cells, since the positive signal given by potent inducers of NK cell cytotoxicity was overruled by DX26 mAb.

XVII. DLAIR-1 is an Inhibitory Receptor on Resting NK Cells

NK cell clones consist of clonally derived populations of activated NK cells. These cells are potently inhibited by DLAIR signaling. We set out to study whether DLAIR is also functioning as an inhibitory receptor on NK cells that had not been previously activated. Resting NK cells, prepared from peripheral blood by negative depletion using -magnetic beads, were able to lyse P815 target cells when simultaneously activated through CD16. This NK cell mediated cytotoxicity was inhibited by the addition of DX26 mAb. Thus, DLAIR is functional as an inhibitory receptor on both activated and resting NK cells.

XVIII. DLAIR is a Widely Expressed Antigen

Phenotypic analysis of human peripheral blood lymphocytes demonstrated that DLAIR is a widely distributed molecule. In healthy donor PBMC, CD3 CD4 T cells (70–80%), $CD3^+CD8^+$ T cells (80–90%), $CD3^-CD56^-$ NK cells (95–100%), $CD3^-CD19^+$ B cells (80–90%), and $CD3^-CD14^+$ monocytes (99–100%) all expressed the DLAIR molecule. Human fetal thymocytes, both the immature $CD4^+CD8^+$ cells and mature $CD4^-CD8^-$ or $CD4^-CD8^+$ single positive cells also expressed DLAIR. Peripheral blood granulocytes, platelets and erythrocytes did not express DLAIR.

Human NK cell clones and T cell clones all expressed DLAIR, with the exception of the long-term cultured NK clones NKL and NK92 (see Table 4). EBV-transformed B cell lines, the B cell tumor Daudi, and the NK tumor cell line YT and several non-hematopoietic cell lines did not express DLAIR, whereas human T cell lines did show DLAIR expression.

TABLE 4

Expression of DLAIR on human tumor cell lines[1]

| cell line | type | control IgG1 | DX26 mAb |
|---|---|---|---|
| | | (mean fluorescence intensity) | |
| HUT78 | T cell tumor | <5 | 25.8 |
| Peer | T cell tumor | <5 | 29.1 |
| Molt4 | T cell tumor | <5 | 30.7 |
| CEM | T cell tumor | <5 | 92.7 |
| Jurkat | T cell tumor | <5 | 47.1 |
| HL60 | promyeloid tumor | <5 | 46.9 |
| U937 | myeloid tumor | <5 | 49.5 |
| 721.221 | EVB- B cell | <5 | <5 |
| JY | EBV- B cell | <5 | <5 |
| Daudi | B cell tumor | <5 | <5 |
| YT | NK cell tumor | <5 | <5 |
| NKL | NK cell clone | <5 | <5 |
| NK92 | NK cell clone | <5 | <5 |
| Colo205 | colon carcinoma | <5 | <5 |
| 293T | embryonic kidney | <5 | <5 |
| PA-1 | teratocarcinoma | <5 | <5 |
| FO-1 | melanoma | <5 | <5 |

[1]cells were stained with control IgG1 or DX26 mAb and PE-conjugated goat-anti-mouse-IgG as a second step. Cells were analyzed on a FACScan.

XIX. Expression Cloning of the DX26 Antigen

The DX26 antibody was used to expression clone the antigen the antibody recognizes. The expression cloning was performed using standard methods. See, e.g., Sambrook, et al. or Coligan, et al.

DX26 antigen is expression cloned, e.g., from a polyclonal human activated NK cell cDNA library in the pJFE14 expression vector. COS7 cells are transfected with the library and antigen positive cells were selected using phycoerythrin labeled anti-DX26 mAb. The cDNA sequence was determined and found to match much of the YE01 sequence. The DX26 antibody specifically binds to the product of the YE01 gene product.

In another method, oligonucleotides are used to screen a library. In combination with polymerase chain reaction (PCR) techniques, synthetic oligonucleotides in appropriate orientations are used as primers to select correct clones from a library.

Moreover, the YE01 gene product is specifically recognized by a monoclonal antibody DX26. This antibody, when crosslinked, can inhibit NK cell mediated killing of certain targets. The antibody recognizes protein expressed in T cells, B cells, NK cells, and monocytes. The gene encoding the antigen recognized by DX26, which is apparently a polymorphic variant of the YE01 isolate, has been cloned and has essentially the sequence (see SEQ ID NO: 7). This isolate has a different 3' untranslated sequence from the original YE01 transcript, apparently due to use of an alternative polyadenylation site. A soluble form of DLAIR has also been detected (see SEQ ID NO: 9).

Distribution analysis of the DX26 isolate has determined, Northern blot analysis, the distribution as follows. Probing of mRNA of human NK cell clones with DLAIR cDNA, PBMC, the human T cell line Jurkat, and the human myeloid cell line Jurkat results in two bands of approximately 1800 bp and 3000–4000 bp. This indicates that besides the cloned cDNA, another transcript with sequence similarity to DLAIR exists in these cell lines. Whether this contains the same open reading frame is at present unknown, but will be determined upon cloning and sequence analysis of that transcript. The EBV-transformed human B cell line JY did not show transcripts that probed with DLAIR cDNA.

XX. DLAIR-1 Binds SHP-1 and SHP-2

The existence of two consensus sequences for ITIMs within the cytoplasmic domain of DLAIR-1, suggested that the generation of an inhibitory signal in NK cells was manifested by the recruitment of SHP-1 and/or SHP-2. To determine if DLAIR-1 was capable of binding protein tyrosine phosphatases, a NK cell clone was stimulated with pervanadate (an inhibitor of protein tyrosine phosphatases that induces tyrosine phosphorylation (O'Shea, et al. (1992) *Proc. Natl. Acad. Sci. USA* 89:10306–10310), lysed, and immunoprecipitated with DX26 MAb. Immunoprecipitates were then analyzed by Western blot using antibodies specific for SHP-1 and SHP-2. Both SHP-1 and SHP-2 associated with tyrosine phosphorylated DLAIR-1. These results suggest that recruitment of SHP-1 and SHP-2 may be involved in mediating the negative signal transduced via engagement of the DLAIR-1 molecule.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or purified antibody, which specifically binds to a human DNAX Leukocyte Associated Immunoglobin-like Receptor (DLAIR) protein wherein:
   a) said antibody is conjugated to another chemical moiety; or
   b) said antibody:
      i) is raised against a peptide selected from the group consisting of sequence of SEQ ID NOs: 6, 8, and 10;
      ii) is raised against a mature human DLAIR protein;
      iii) is raised to a purified human DLAIR protein;
      iv) is a polyclonal antibody;
      v) binds to a denatured human DLAIR protein;
      vi) exhibits a $K_D$ to antigen of at least 30 μM;
      vii) is attached to a solid substrate, including a bead or plastic membrane;
      viii) is in a sterile composition; or
      ix) is detectably labeled, including a radioactive or fluorescent label.

2. A kit comprising:
   a) a compartment comprising the antibody of claim 1; and
   b) instructions for use or disposal of reagents.

3. The kit of claim 2 capable of making a qualitative or quantitative analysis.

4. A composition comprising:
   a) an antibody of claim 1 in a sterile form; or
   b) an antibody of claim 1 and a carrier, wherein said carrier is water, saline, or buffer.

5. The antibody of claim 1, wherein said antibody comprises a monoclonal antibody, an Fv fragment, Fab fragment, F(ab')$_2$ fragment, or a single chain antibody.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 1249 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 154..1062

(ix) FEATURE:
      (A) NAME/KEY: mat_peptide
      (B) LOCATION: 211..1062

(xi) SEQUENCE DESCRIPTION: SEQ ID NO: 1:

```
GTTTGGGGAA GGCTCCTGGC CCCCACAGCC CTCTTCGGAG CCTGAGCCCG GCTCTCCTCA        60

CTCACCTCAA CCCCCAGGCG GCCCCTCCAC AGGGCCCCTC TCCTGCCTGG ACGGCTCTGC       120

TGGTCTCCCC GTCCCCTGGA GAAGAACAAG GCC ATG GGT CGG CCC CTG CTG CTG       174
                                    Met Gly Arg Pro Leu Leu Leu
                                        -19              -15

CCC CTA CTG CCC CTG CTG CTG CCG CCA GCA TTT CTG CAG CCT AGT GGC        222
Pro Leu Leu Pro Leu Leu Leu Pro Pro Ala Phe Leu Gln Pro Ser Gly
        -10                 -5                   1

TCC ACA GGA TCT GGT CCA AGC TAC CTT TAT GGG GTC ACT CAA CCA AAA        270
Ser Thr Gly Ser Gly Pro Ser Tyr Leu Tyr Gly Val Thr Gln Pro Lys
  5                  10                  15                  20

CAC CTC TCA GCC TCC ATG GGT GGC TCT GTG GAA ATC CCC TTC TCC TTC        318
His Leu Ser Ala Ser Met Gly Gly Ser Val Glu Ile Pro Phe Ser Phe
                     25                  30                  35

TAT TAC CCC TGG GAG TTA GCC ACA GCT CCC GAC GTG AGA ATA TCC TGG        366
Tyr Tyr Pro Trp Glu Leu Ala Thr Ala Pro Asp Val Arg Ile Ser Trp
             40                  45                  50

AGA CGG GGC CAC TTC CAC GGG CAG TCC TTC TAC AGC ACA AGG CCG CCT        414
Arg Arg Gly His Phe His Gly Gln Ser Phe Tyr Ser Thr Arg Pro Pro
         55                  60                  65

TCC ATT CAC AAG GAT TAT GTG AAC CGG CTC TTT CTG AAC TGG ACA GAG        462
Ser Ile His Lys Asp Tyr Val Asn Arg Leu Phe Leu Asn Trp Thr Glu
     70                  75                  80

GGT CAG AAG AGC GGC TTC CTC AGG ATC TCC AAC CTG CAG AAG CAG GAC        510
Gly Gln Lys Ser Gly Phe Leu Arg Ile Ser Asn Leu Gln Lys Gln Asp
 85                  90                  95                 100

CAG TCT GTG TAT TTC TGC CGA GTT GAG CTG GAC ACA CGG AGC TCA GGG        558
Gln Ser Val Tyr Phe Cys Arg Val Glu Leu Asp Thr Arg Ser Ser Gly
                105                 110                 115

AGG CAG CAG TGG CAG TCC ATC GAG GGG ACC AAA CTC TCC ATC ACC CAG        606
Arg Gln Gln Trp Gln Ser Ile Glu Gly Thr Lys Leu Ser Ile Thr Gln
            120                 125                 130

GCT GTC ACG ACC ACC ACC CAG AGG CCC AGC AGC ATG ACT ACC ACC TGG        654
Ala Val Thr Thr Thr Thr Gln Arg Pro Ser Ser Met Thr Thr Thr Trp
        135                 140                 145

AGG CTC AGT AGC ACA ACC ACC ACA ACC GGC CTC AGG GTC ACA CAG GGC        702
Arg Leu Ser Ser Thr Thr Thr Thr Gly Leu Arg Val Thr Gln Gly
    150                 155                 160
```

```
AAA CGA CGC TCA GAC TCT TGG CAC ATA AGT CTG GAG ACT GCT GTG GGG     750
Lys Arg Arg Ser Asp Ser Trp His Ile Ser Leu Glu Thr Ala Val Gly
165             170                 175                 180

GTG GCA GTG GCT GTC ACT GTG CTC GGA ATC ATG ATT TTG GGA CTG ATC     798
Val Ala Val Ala Val Thr Val Leu Gly Ile Met Ile Leu Gly Leu Ile
                185                 190                 195

TGC CTC CTC AGG TGG AGG AGA AGG AAA GGT CAG CAG CGG ACT AAA GCC     846
Cys Leu Leu Arg Trp Arg Arg Arg Lys Gly Gln Gln Arg Thr Lys Ala
                200                 205                 210

ACA ACC CCA GCC AGG GAA CCC TTC CAA AAC ACA GAG GAG CCA TAT GAG     894
Thr Thr Pro Ala Arg Glu Pro Phe Gln Asn Thr Glu Glu Pro Tyr Glu
            215                 220                 225

AAT ATC AGG AAT GAA GGA CAA AAT ACA GAT CCC AAG CTA AAT CCC AAG     942
Asn Ile Arg Asn Glu Gly Gln Asn Thr Asp Pro Lys Leu Asn Pro Lys
        230                 235                 240

GAT GAC GGC ATC GTA TAT GCT TCC CTT GCC CTC TCC AGC TCC ACC TCA     990
Asp Asp Gly Ile Val Tyr Ala Ser Leu Ala Leu Ser Ser Ser Thr Ser
245                 250                 255                 260

CCC AGA GCA CCT CCC AGC CAC CGT CCC CTC AAG AGC CCC CAG AAC GAG    1038
Pro Arg Ala Pro Pro Ser His Arg Pro Leu Lys Ser Pro Gln Asn Glu
                265                 270                 275

ACC CTG TAC TCT GTC TTA AAG GCC TAACCAATGG ACAGCCCTCT CAAGACTGAA    1092
Thr Leu Tyr Ser Val Leu Lys Ala
                280

TGGTGAGGCC AGGTACAGTG GCGCACACCT GTAATCCCAG CTACTCTGAA GCCTGAGGCA   1152

GAATCAAGTG AGCCCAGGAG TTCAGGGCCA GCTTTGATAA TGGAGCGAGA TGCCATCTCT   1212

AGTTAAAAAT ATATATTAAC AATAAAGTAA CAAATTT                           1249

(2) INFORMATION FOR SEQ ID NO: 2:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Arg Pro Leu Leu Leu Pro Leu Leu Leu Pro Pro
-19             -15                 -10             -5

Ala Phe Leu Gln Pro Ser Gly Ser Thr Gly Ser Gly Pro Ser Tyr Leu
                1                   5                   10

Tyr Gly Val Thr Gln Pro Lys His Leu Ser Ala Ser Met Gly Gly Ser
            15                  20                  25

Val Glu Ile Pro Phe Ser Phe Tyr Tyr Pro Trp Glu Leu Ala Thr Ala
30                  35                  40                  45

Pro Asp Val Arg Ile Ser Trp Arg Arg Gly His Phe His Gly Gln Ser
                50                  55                  60

Phe Tyr Ser Thr Arg Pro Pro Ser Ile His Lys Asp Tyr Val Asn Arg
            65                  70                  75

Leu Phe Leu Asn Trp Thr Glu Gly Gln Lys Ser Gly Phe Leu Arg Ile
        80                  85                  90

Ser Asn Leu Gln Lys Gln Asp Gln Ser Val Tyr Phe Cys Arg Val Glu
        95                  100                 105

Leu Asp Thr Arg Ser Ser Gly Arg Gln Gln Trp Gln Ser Ile Glu Gly
110                 115                 120                 125

Thr Lys Leu Ser Ile Thr Gln Ala Val Thr Thr Thr Gln Arg Pro
```

```
                    130              135              140
Ser Ser Met Thr Thr Thr Trp Arg Leu Ser Ser Thr Thr Thr Thr
            145              150              155

Gly Leu Arg Val Thr Gln Gly Lys Arg Arg Ser Asp Ser Trp His Ile
        160              165              170

Ser Leu Glu Thr Ala Val Gly Val Ala Ala Val Thr Val Leu Gly
    175              180              185

Ile Met Ile Leu Gly Leu Ile Cys Leu Leu Arg Trp Arg Arg Arg Lys
190              195              200              205

Gly Gln Gln Arg Thr Lys Ala Thr Thr Pro Ala Arg Glu Pro Phe Gln
                210              215              220

Asn Thr Glu Glu Pro Tyr Glu Asn Ile Arg Asn Glu Gly Gln Asn Thr
                225              230              235

Asp Pro Lys Leu Asn Pro Lys Asp Asp Gly Ile Val Tyr Ala Ser Leu
            240              245              250

Ala Leu Ser Ser Ser Thr Ser Pro Arg Ala Pro Pro Ser His Arg Pro
    255              260              265

Leu Lys Ser Pro Gln Asn Glu Thr Leu Tyr Ser Val Leu Lys Ala
270              275              280
```

(2) INFORMATION FOR SEQ ID NO: 3:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 78..374

(xi) SEQUENCE DESCRIPTION: SEQ ID NO: 3:

```
CCCCAGTGTC CCTAGACAGA GCATCCTTGC CTTCCTGATG GCTTTGCTGA TCTCGCTTCC      60

CTGGAGGGAC TCCAGCC ATG GCT CAG GTC CTG CTT CTG CTC TCA TCA GGC        110
                   Met Ala Gln Val Leu Leu Leu Leu Ser Ser Gly
                    1               5              10

TGT CTG CAT GCT GGA AAT TCA GAA AGA TAC AAC AGA AAA AAT GGC TTT      158
Cys Leu His Ala Gly Asn Ser Glu Arg Tyr Asn Arg Lys Asn Gly Phe
            15                  20                  25

GGG GTC AAC CAA CCT GAA CGC TGC TCT GGA GTC CAG GGT GGC TCC ATC      206
Gly Val Asn Gln Pro Glu Arg Cys Ser Gly Val Gln Gly Gly Ser Ile
        30                  35                  40

GAC ATC CCC TTC TCC TTC TAT TTC CCC TGG AAG TTG GCC AAG GAT CCA      254
Asp Ile Pro Phe Ser Phe Tyr Phe Pro Trp Lys Leu Ala Lys Asp Pro
    45                  50                  55

CAG ATG AGC ATA GCC TGG AAA TGG AAG GAT TTC CAT GGG GAA GTC ATC      302
Gln Met Ser Ile Ala Trp Lys Trp Lys Asp Phe His Gly Glu Val Ile
60                  65                  70                  75

TAC AAC TCC TCC CTG CCT TTC ATA CAT GAG CAC TTC AAG GGC CGG CTC      350
Tyr Asn Ser Ser Leu Pro Phe Ile His Glu His Phe Lys Gly Arg Leu
                80                  85                  90

ATC CTG AAC TGG ACA CAG GGT CAG AC                                    376
Ile Leu Asn Trp Thr Gln Gly Gln
                95
```

(2) INFORMATION FOR SEQ ID NO: 4:

```
    (i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Gln Val Leu Leu Leu Ser Ser Gly Cys Leu His Ala Gly
 1               5                  10                  15

Asn Ser Glu Arg Tyr Asn Arg Lys Asn Gly Phe Gly Val Asn Gln Pro
            20                  25                  30

Glu Arg Cys Ser Gly Val Gln Gly Gly Ser Ile Asp Ile Pro Phe Ser
         35                  40                  45

Phe Tyr Phe Pro Trp Lys Leu Ala Lys Asp Pro Gln Met Ser Ile Ala
     50                  55                  60

Trp Lys Trp Lys Asp Phe His Gly Glu Val Ile Tyr Asn Ser Ser Leu
 65                  70                  75                  80

Pro Phe Ile His Glu His Phe Lys Gly Arg Leu Ile Leu Asn Trp Thr
                 85                  90                  95

Gln Gly Gln (2) INFORMATION FOR SEQ ID NO: 5:

(i) SEQUENCE CHARACTERISTICS:
        (A) LENGTH: 1279 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 155..1015

(ix) FEATURE:
        (A) NAME/KEY: misc_feature
        (B) LOCATION: 1247
        (D) OTHER INFORMATION: /note= "nucleotide 1247 designated
            C, but may be C or T"

(ix) FEATURE:
        (A) NAME/KEY: mat_peptide
        (B) LOCATION: 218..1015

(xi) SEQUENCE DESCRIPTION: SEQ ID NO: 5:

ACCGGTCCGG AATTCCCGGG TCGACCCACG CGTCCGGGAA GCCCCATAGG CAGGAGGCCC        60

CCGGGCAGCA CATCCTGTCT GCTTGTGTCT GCTGCAGAGT TCTGTCCTTG CATTGGTGCG       120

CCTCAGGCCA GGCTGCACTG CTGGGACCTG GGCC ATG TCT CCC CAC CCC ACC          172
                                     Met Ser Pro His Pro Thr
                                     -21 -20

GCC CTC CTG GGC CTA GTG CTC TGC CTG GCC CAG ACC ATC CAC ACG CAG        220
Ala Leu Leu Gly Leu Val Leu Cys Leu Ala Gln Thr Ile His Thr Gln
-15                 -10                 -5                   1

GAG GAA GAT CTG CCC AGA CCC TCC ATC TCG GCT GAG CCA GGC ACC GTG        268
Glu Glu Asp Leu Pro Arg Pro Ser Ile Ser Ala Glu Pro Gly Thr Val
              5                  10                  15

ATC CCC CTG GGG AGC CAT GTG ACT TTC GTG TGC CGG GGC CCG GTT GGG        316
Ile Pro Leu Gly Ser His Val Thr Phe Val Cys Arg Gly Pro Val Gly
             20                  25                  30

GTT CAA ACA TTC CGC CTG GAG AGG GAG AGT AGA TCC ACA TAC AAT GAT        364
Val Gln Thr Phe Arg Leu Glu Arg Glu Ser Arg Ser Thr Tyr Asn Asp
```

|                                                                                      |      |
| ------------------------------------------------------------------------------------ | ---- |
| ACT GAA GAT GTG TCT CAA GCT AGT CCA TCT GAG TCA GAG GCC AGA TTC                      | 412  |
| Thr Glu Asp Val Ser Gln Ala Ser Pro Ser Glu Ser Glu Ala Arg Phe                      |      |
| 50                  55                  60                  65                       |      |
| CGC ATT GAC TCA GTA AGT GAA GGA AAT GCC GGG CCT TAT CGC TGC ATC                      | 460  |
| Arg Ile Asp Ser Val Ser Glu Gly Asn Ala Gly Pro Tyr Arg Cys Ile                      |      |
|                     70                  75                  80                       |      |
| TAT TAT AAG CCC CCT AAA TGG TCT GAG CAG AGT GAC TAC CTG GAG CTG                      | 508  |
| Tyr Tyr Lys Pro Pro Lys Trp Ser Glu Gln Ser Asp Tyr Leu Glu Leu                      |      |
|                 85                  90                  95                           |      |
| CTG GTG AAA GAA ACC TCT GGA GGC CCG GAC TCC CCG GAC ACA GAG CCC                      | 556  |
| Leu Val Lys Glu Thr Ser Gly Gly Pro Asp Ser Pro Asp Thr Glu Pro                      |      |
|             100                 105                 110                              |      |
| GGC TCC TCA GCT GGA CCC ACG CAG AGG CCG TCG GAC AAC AGT CAC AAT                      | 604  |
| Gly Ser Ser Ala Gly Pro Thr Gln Arg Pro Ser Asp Asn Ser His Asn                      |      |
|         115                 120                 125                                  |      |
| GAG CAT GCA CCT GCT TCC CAA GGC CTG AAA GCT GAG CAT CTG TAT ATT                      | 652  |
| Glu His Ala Pro Ala Ser Gln Gly Leu Lys Ala Glu His Leu Tyr Ile                      |      |
| 130                 135                 140                 145                      |      |
| CTC ATC GGG GTC TCA GTG GTC TTC CTC TTC TGT CTC CTC CTC CTG GTC                      | 700  |
| Leu Ile Gly Val Ser Val Val Phe Leu Phe Cys Leu Leu Leu Leu Val                      |      |
|                 150                 155                 160                          |      |
| CTC TTC TGC CTC CAT CGC CAG AAT CAG ATA AAG CAG GGG CCC CCC AGA                      | 748  |
| Leu Phe Cys Leu His Arg Gln Asn Gln Ile Lys Gln Gly Pro Pro Arg                      |      |
|             165                 170                 175                              |      |
| AGC AAG GAC GAG GAG CAG AAG CCA CAG CAG AGG CCT GAC CTG GCT GTT                      | 796  |
| Ser Lys Asp Glu Glu Gln Lys Pro Gln Gln Arg Pro Asp Leu Ala Val                      |      |
|         180                 185                 190                                  |      |
| GAT GTT CTA GAG AGG ACA GCA GAC AAG GCC ACA GTC AAT GGA CTT CCT                      | 844  |
| Asp Val Leu Glu Arg Thr Ala Asp Lys Ala Thr Val Asn Gly Leu Pro                      |      |
| 195                 200                 205                                          |      |
| GAG AAG GAC AGA GAG ACG GAC ACC TCG GCC CTG GCT GCA GGG AGT TCC                      | 892  |
| Glu Lys Asp Arg Glu Thr Asp Thr Ser Ala Leu Ala Ala Gly Ser Ser                      |      |
| 210                 215                 220                 225                      |      |
| CAG GAG GTG ACG TAT GCT CAG CTG GAC CAC TGG GCC CTC ACA CAG AGG                      | 940  |
| Gln Glu Val Thr Tyr Ala Gln Leu Asp His Trp Ala Leu Thr Gln Arg                      |      |
|                 230                 235                 240                          |      |
| ACA GCC CGG GCT GTG TCC CCA CAG TCC ACA AAG CCC ATG GCC GAG TCC                      | 988  |
| Thr Ala Arg Ala Val Ser Pro Gln Ser Thr Lys Pro Met Ala Glu Ser                      |      |
|             245                 250                 255                              |      |
| ATC ACG TAT GCA GCC GTT GCC AGA CAC TGACCCCATA CCCACCTGGC                            | 1035 |
| Ile Thr Tyr Ala Ala Val Ala Arg His                                                  |      |
|         260                 265                                                      |      |
| CTCTGCACCT GAGGGTAGAA AGTCACTCTA GGAAAAGCCT GAAGCAGCCA TTTGGAAGGC                    | 1095 |
| TTCCTGTTGG ATTCCTCTTC ATCTAGAAAG CCAGCCAGGC AGCTGTCCTG GAGACAAGAG                    | 1155 |
| CTGGAGACTG GAGGTTTCTA ACCAGCATCC AGAAGGTTCG TTAGCCAGGT GGTCCCTTCT                    | 1215 |
| ACAATCGGAC AGCTCCTTGG ACAGACTGTT TCTCAGTTAT TTCCAAAAAC CCAGCTACAG                    | 1275 |
| TTCC                                                                                 | 1279 |

(2) INFORMATION FOR SEQ ID NO: 6:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ser Pro His Pro Thr Ala Leu Leu Gly Leu Val Leu Cys Leu Ala
-21 -20              -15              -10

Gln Thr Ile His Thr Gln Glu Glu Asp Leu Pro Arg Pro Ser Ile Ser
 -5              1               5                          10

Ala Glu Pro Gly Thr Val Ile Pro Leu Gly Ser His Val Thr Phe Val
             15              20                      25

Cys Arg Gly Pro Val Gly Val Gln Thr Phe Arg Leu Glu Arg Glu Ser
             30              35                  40

Arg Ser Thr Tyr Asn Asp Thr Glu Asp Val Ser Gln Ala Ser Pro Ser
         45              50                  55

Glu Ser Glu Ala Arg Phe Arg Ile Asp Ser Val Ser Glu Gly Asn Ala
 60              65                  70                      75

Gly Pro Tyr Arg Cys Ile Tyr Tyr Lys Pro Pro Lys Trp Ser Glu Gln
                     80              85                  90

Ser Asp Tyr Leu Glu Leu Leu Val Lys Glu Thr Ser Gly Gly Pro Asp
             95              100                 105

Ser Pro Asp Thr Glu Pro Gly Ser Ser Ala Gly Pro Thr Gln Arg Pro
         110             115                 120

Ser Asp Asn Ser His Asn Glu His Ala Pro Ala Ser Gln Gly Leu Lys
         125             130                 135

Ala Glu His Leu Tyr Ile Leu Ile Gly Val Ser Val Val Phe Leu Phe
140             145                 150                     155

Cys Leu Leu Leu Val Leu Phe Cys Leu His Arg Gln Asn Gln Ile
                 160             165                 170

Lys Gln Gly Pro Pro Arg Ser Lys Asp Glu Glu Gln Lys Pro Gln Gln
             175             180                 185

Arg Pro Asp Leu Ala Val Asp Val Leu Glu Arg Thr Ala Asp Lys Ala
         190             195                 200

Thr Val Asn Gly Leu Pro Glu Lys Asp Arg Glu Thr Asp Thr Ser Ala
         205             210                 215

Leu Ala Ala Gly Ser Ser Gln Glu Val Thr Tyr Ala Gln Leu Asp His
220             225                 230                     235

Trp Ala Leu Thr Gln Arg Thr Ala Arg Ala Val Ser Pro Gln Ser Thr
             240             245                 250

Lys Pro Met Ala Glu Ser Ile Thr Tyr Ala Ala Val Ala Arg His
             255             260                 265
```

(2) INFORMATION FOR SEQ ID NO: 7:

(i) SEQUENCE CHARACTERISTICS:
        (A) LENGTH: 1728 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 69..929

(ix) FEATURE:
        (A) NAME/KEY: mat_peptide
        (B) LOCATION: 132..929

(xi) SEQUENCE DESCRIPTION: SEQ ID NO: 7:

```
AAAGGCTGCA GAGTTCTGTC CTTGCATTGG TGCGCCTCAG GCCAGGCTGC ACTGCTGGGA        60

CCTGGGCC ATG TCT CCC CAC CCC ACC GCC CTC CTG GGC CTA GTG CTC TGC       110
```

```
            Met Ser Pro His Pro Thr Ala Leu Leu Gly Leu Val Leu Cys
            -21 -20             -15                 -10

CTG GCC CAG ACC ATC CAC ACG CAG GAG GAA GAT CTG CCC AGA CCC TCC         158
Leu Ala Gln Thr Ile His Thr Gln Glu Glu Asp Leu Pro Arg Pro Ser
        -5                   1                   5

ATC TCG GCT GAG CCA GGC ACC GTG ATC CCC CTG GGG AGC CAT GTG ACT         206
Ile Ser Ala Glu Pro Gly Thr Val Ile Pro Leu Gly Ser His Val Thr
10              15                  20                  25

TTC GTG TGC CGG GGC CCG GTT GGG GTT CAA ACA TTC CGC CTG GAG AGG         254
Phe Val Cys Arg Gly Pro Val Gly Val Gln Thr Phe Arg Leu Glu Arg
                30                  35                  40

GAG AGT AGA TCC ACA TAC AAT GAT ACT GAA GAT GTG TCT CAA GCT AGT         302
Glu Ser Arg Ser Thr Tyr Asn Asp Thr Glu Asp Val Ser Gln Ala Ser
            45                  50                  55

CCA TCT GAG TCA GAG GCC AGA TTC CGC ATT GAC TCA GTA AGT GAA GGA         350
Pro Ser Glu Ser Glu Ala Arg Phe Arg Ile Asp Ser Val Ser Glu Gly
        60                  65                  70

AAT GCC GGG CCT TAT CGC TGC ATC TAT TAT AAG CCC CCT AAA TGG TCT         398
Asn Ala Gly Pro Tyr Arg Cys Ile Tyr Tyr Lys Pro Pro Lys Trp Ser
75              80                  85

GAG CAG AGT GAC TAC CTG GAG CTG CTG GTG AAA GAA ACC TCT GGA GGC         446
Glu Gln Ser Asp Tyr Leu Glu Leu Leu Val Lys Glu Thr Ser Gly Gly
90                  95                  100                 105

CCG GAC TCC CCG GAC ACA GAG CCC GGC TCC TCA GCT GGA CCC ACG CAG         494
Pro Asp Ser Pro Asp Thr Glu Pro Gly Ser Ser Ala Gly Pro Thr Gln
                110                 115                 120

AGG CCG TCG GAC AAC AGT CAC AAT GAG CAT GCA CCT GCT TCC CAA GGC         542
Arg Pro Ser Asp Asn Ser His Asn Glu His Ala Pro Ala Ser Gln Gly
            125                 130                 135

CTG AAA GCT GAG CAT CTG TAT ATT CTC ATC GGG GTC TCA GTG GTC TTC         590
Leu Lys Ala Glu His Leu Tyr Ile Leu Ile Gly Val Ser Val Val Phe
        140                 145                 150

CTC TTC TGT CTC CTC CTC CTG GTC CTC TTC TGC CTC CAT CGC CAG AAT         638
Leu Phe Cys Leu Leu Leu Leu Val Leu Phe Cys Leu His Arg Gln Asn
155                 160                 165

CAG ATA AAG CAG GGG CCC CCC AGA AGC AAG GAC GAG GAG CAG AAG CCA         686
Gln Ile Lys Gln Gly Pro Pro Arg Ser Lys Asp Glu Glu Gln Lys Pro
170                 175                 180                 185

CAG CAG AGG CCT GAC CTG GCT GTT GAT GTT CTA GAG AGG ACA GCA GAC         734
Gln Gln Arg Pro Asp Leu Ala Val Asp Val Leu Glu Arg Thr Ala Asp
                190                 195                 200

AAG GCC ACA GTC AAT GGA CTT CCT GAG AAG GAC AGA GAG ACG GAC ACC         782
Lys Ala Thr Val Asn Gly Leu Pro Glu Lys Asp Arg Glu Thr Asp Thr
            205                 210                 215

TCG GCC CTG GCT GCA GGG AGT TCC CAG GAG GTG ACG TAT GCT CAG CTG         830
Ser Ala Leu Ala Ala Gly Ser Ser Gln Glu Val Thr Tyr Ala Gln Leu
        220                 225                 230

GAC CAC TGG GCC CTC ACA CAG AGG ACA GCC CGG GCT GTG TCC CCA CAG         878
Asp His Trp Ala Leu Thr Gln Arg Thr Ala Arg Ala Val Ser Pro Gln
235                 240                 245

TCC ACA AAG CCC ATG GCC GAG TCC ATC ACG TAT GCA GCC GTT GCC AGA         926
Ser Thr Lys Pro Met Ala Glu Ser Ile Thr Tyr Ala Ala Val Ala Arg
250                 255                 260                 265

CAC TGACCCCATA CCCACCTGGC CTCTGCACCT GAGGGTAGAA AGTCACTCTA              979
His

GGAAAAGCCT GAAGCAGCCA TTTGGAAGGC TTCCTGTTGG ATTCCTCTTC ATCTAGAAAG       1039

CCAGCCAGGC AGCTGTCCTG GAGACAAGAG CTGGAGACTG GAGGTTTCTA ACCAGCATCC       1099

AGAAGGTTCG TTAGCCAGGT GGTCCCTTCT ACAATCGAGC AGCTCCTTGG ACAGACTGTT      1159
```

```
TCTCAGTTAT TTCCAGAGAC CCAGCTACAG TTCCCTGGCT GTTTCTAGAG ACCCAGCTTT    1219

ATTCACCTGA CTGTTTCCAG AGACCCAGCT AAAGTCACCT GCCTGTTCTA AAGGCCCAGC    1279

TACAGCCAAT CAGCCGATTT CCTGAGCAGT GATGCCACCT CCAAGCTTGT CCTAGGTGTC    1339

TGCTGTGAAC CTCCAGTGAC CCAGAGACT TTGCTGTAAT TATCTGCCCT GCTGACCCTA     1399

AAGACCTTCC TAGAAGTCAA GAGCTAGCCT TGAGACTGTG CTATACACAC ACAGCTGAGA    1459

GCCAAGCCCA GTTCTCTGGG TTGTGCTTTA CTCCAAGCAT CAATAAATAA TTTTGAAGGC    1519

CTCACATCTG GCAGCCCCAG GCCTGGTCCT GGGTGCATAG GTCTCTCGGA CCCACTCTCT    1579

GCCTTCACAG TTGTTCAAAG CTGAGTGAGG GAAACAGGAC TTACGAAAAC GTGTCAGCGT    1639

TTTCTTTTTA AAATTTAATT GATCAGGATT GTACGTAAAA AAAAAAAAAA AAAAAAAAAA    1699

AAAAAAAAAA AAAAAAAAAA AAAAAAGG                                      1728
```

(2) INFORMATION FOR SEQ ID NO: 8:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ser Pro His Pro Thr Ala Leu Leu Gly Leu Val Leu Cys Leu Ala
-21 -20             -15                 -10

Gln Thr Ile His Thr Gln Glu Glu Asp Leu Pro Arg Pro Ser Ile Ser
 -5              1               5                  10

Ala Glu Pro Gly Thr Val Ile Pro Leu Gly Ser His Val Thr Phe Val
             15              20              25

Cys Arg Gly Pro Val Gly Val Gln Thr Phe Arg Leu Glu Arg Glu Ser
             30              35              40

Arg Ser Thr Tyr Asn Asp Thr Glu Asp Val Ser Gln Ala Ser Pro Ser
     45              50              55

Glu Ser Glu Ala Arg Phe Arg Ile Asp Ser Val Ser Glu Gly Asn Ala
 60              65              70              75

Gly Pro Tyr Arg Cys Ile Tyr Tyr Lys Pro Pro Lys Trp Ser Glu Gln
             80              85              90

Ser Asp Tyr Leu Glu Leu Leu Val Lys Glu Thr Ser Gly Gly Pro Asp
             95             100             105

Ser Pro Asp Thr Glu Pro Gly Ser Ser Ala Gly Pro Thr Gln Arg Pro
            110             115             120

Ser Asp Asn Ser His Asn Glu His Ala Pro Ala Ser Gln Gly Leu Lys
        125             130             135

Ala Glu His Leu Tyr Ile Leu Ile Gly Val Ser Val Val Phe Leu Phe
140             145             150             155

Cys Leu Leu Leu Leu Val Leu Phe Cys Leu His Arg Gln Asn Gln Ile
            160             165             170

Lys Gln Gly Pro Pro Arg Ser Lys Asp Glu Glu Gln Lys Pro Gln Gln
            175             180             185

Arg Pro Asp Leu Ala Val Asp Val Leu Glu Arg Thr Ala Asp Lys Ala
        190             195             200

Thr Val Asn Gly Leu Pro Glu Lys Asp Arg Glu Thr Asp Thr Ser Ala
    205             210             215

Leu Ala Ala Gly Ser Ser Gln Glu Val Thr Tyr Ala Gln Leu Asp His
```

```
220                 225                 230                 235
Trp Ala Leu Thr Gln Arg Thr Ala Arg Ala Val Ser Pro Gln Ser Thr
                240                 245                 250

Lys Pro Met Ala Glu Ser Ile Thr Tyr Ala Ala Val Ala Arg His
                255                 260                 265
```

(2) INFORMATION FOR SEQ ID NO: 9:

(i) SEQUENCE CHARACTERISTICS:
        (A) LENGTH: 568 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 24..428

(ix) FEATURE:
        (A) NAME/KEY: mat_peptide
        (B) LOCATION: 87..428

(xi) SEQUENCE DESCRIPTION: SEQ ID NO: 9:

```
CCACGCGTCC GGGGACCGGG GCC ATG TCT CCA CAC CTC ACT GCT CTC CTG          50
                         Met Ser Pro His Leu Thr Ala Leu Leu
                         -21 -20                 -15

GGC CTA GTG CTC TGC CTG GCC CAG ACC ATC CAC ACG CAG GAG GGG GCC        98
Gly Leu Val Leu Cys Leu Ala Gln Thr Ile His Thr Gln Glu Gly Ala
        -10                 -5                   1

CTT CCC AGA CCC TCC ATC TCG GCT GAG CCA GGC ACT GTG ATC TCC CCG       146
Leu Pro Arg Pro Ser Ile Ser Ala Glu Pro Gly Thr Val Ile Ser Pro
 5                  10                  15                  20

GGG AGC CAT GTG ACT TTC ATG TGC CGG GGC CCG GTT GGG GTT CAA ACA       194
Gly Ser His Val Thr Phe Met Cys Arg Gly Pro Val Gly Val Gln Thr
                 25                  30                  35

TTC CGC CTG GAG AGG GAG GAT AGA GCC AAG TAC AAA GAT AGT TAT AAT       242
Phe Arg Leu Glu Arg Glu Asp Arg Ala Lys Tyr Lys Asp Ser Tyr Asn
             40                  45                  50

GTG TTT CGA CTT GGT CCA TCT GAG TCA GAG GCC AGA TTC CAC ATT GAC       290
Val Phe Arg Leu Gly Pro Ser Glu Ser Glu Ala Arg Phe His Ile Asp
         55                  60                  65

TCA GTA AGT GAA GGA AAT GCC GGG CTT TAT CGC TGC CTC TAT TAT AAG       338
Ser Val Ser Glu Gly Asn Ala Gly Leu Tyr Arg Cys Leu Tyr Tyr Lys
     70                  75                  80

CCC CCT GGA TGG TCT GAG CAC AGT GAC TTC CTG GAG CTG CTG GTG AAA       386
Pro Pro Gly Trp Ser Glu His Ser Asp Phe Leu Glu Leu Leu Val Lys
 85                  90                  95                 100

GGG ACT GTG CCA GGC ACT GAA GCC TCC GGA TTT GAT GCA CCA               428
Gly Thr Val Pro Gly Thr Glu Ala Ser Gly Phe Asp Ala Pro
                105                 110

TGAATGAGGA GAAATGGCCT CCCGTCTTGT GAACTTCAAT GGGGAGAAAT AATTAGAATG     488

AGCAATAGAA ATGCACAGAT GCCTATACAT ACATATACAA ATAAAAAGAT ACGATTCGCA     548

AAAAAAAAAA AAAAAAGGGC                                                 568
```

(2) INFORMATION FOR SEQ ID NO: 10:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ser Pro His Leu Thr Ala Leu Leu Gly Leu Val Leu Cys Leu Ala
-21 -20             -15                 -10

Gln Thr Ile His Thr Gln Glu Gly Ala Leu Pro Arg Pro Ser Ile Ser
 -5              1           5                  10

Ala Glu Pro Gly Thr Val Ile Ser Pro Gly Ser His Val Thr Phe Met
            15              20                  25

Cys Arg Gly Pro Val Gly Val Gln Thr Phe Arg Leu Glu Arg Glu Asp
        30              35                  40

Arg Ala Lys Tyr Lys Asp Ser Tyr Asn Val Phe Arg Leu Gly Pro Ser
    45                  50              55

Glu Ser Glu Ala Arg Phe His Ile Asp Ser Val Ser Glu Gly Asn Ala
60              65                  70                      75

Gly Leu Tyr Arg Cys Leu Tyr Tyr Lys Pro Pro Gly Trp Ser Glu His
                80              85              90

Ser Asp Phe Leu Glu Leu Leu Val Lys Gly Thr Val Pro Gly Thr Glu
            95              100             105

Ala Ser Gly Phe Asp Ala Pro
        110
```

(2) INFORMATION FOR SEQ ID NO: 11:

(i) SEQUENCE CHARACTERISTICS:
        (A) LENGTH: 1620 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 81..1397

(xi) SEQUENCE DESCRIPTION: SEQ ID NO: 11:

```
GTCGACCCAC GCGTCCGCCT CTGTCCTGCC AGCACCGAGG GCTCATCCAT CCACAGAGCA         60

GTGCAGTGGG AGGAGACGCC ATG ACC CCC ATC CTC ACG GTC CTG ATC TGT           110
                     Met Thr Pro Ile Leu Thr Val Leu Ile Cys
                      1               5                  10

CTC GGG CTG AGC CTG GAC CCC AGG ACC CAC GTG CAG GCA GGG CCC CTC         158
Leu Gly Leu Ser Leu Asp Pro Arg Thr His Val Gln Ala Gly Pro Leu
                15                  20                  25

CCC AAG CCC ACC CTC TGG GCT GAG CCA GGC TCT GTG ATC ACC CAA GGG         206
Pro Lys Pro Thr Leu Trp Ala Glu Pro Gly Ser Val Ile Thr Gln Gly
        30                  35                  40

AGT CCT GTG ACC CTC AGG TGT CAG GGG AGC CTG GAG ACG CAG GAG TAC         254
Ser Pro Val Thr Leu Arg Cys Gln Gly Ser Leu Glu Thr Gln Glu Tyr
    45                  50                  55

CAT CTA TAT AGA GAA AAG AAA ACA GCA CTC TGG ATT ACA CGG ATC CCA         302
His Leu Tyr Arg Glu Lys Lys Thr Ala Leu Trp Ile Thr Arg Ile Pro
60                  65                  70

CAG GAG CTT GTG AAG AAG GGC CAG TTC CCC ATC CTA TCC ATC ACC TGG         350
Gln Glu Leu Val Lys Lys Gly Gln Phe Pro Ile Leu Ser Ile Thr Trp
75                  80                  85                  90

GAA CAT GCA GGG CGG TAT TGC TGT ATC TAT GGC AGC CAC ACT GCA GGC         398
Glu His Ala Gly Arg Tyr Cys Cys Ile Tyr Gly Ser His Thr Ala Gly
                95                  100                 105
```

-continued

```
CTC TCA GAG AGC AGT GAC CCC CTG GAG CTG GTG GTG ACA GGA GCC TAC       446
Leu Ser Glu Ser Ser Asp Pro Leu Glu Leu Val Val Thr Gly Ala Tyr
        110                 115                 120

AGC AAA CCC ACC CTC TCA GCT CTG CCC AGC CCT GTG GTG ACC TCA GGA       494
Ser Lys Pro Thr Leu Ser Ala Leu Pro Ser Pro Val Val Thr Ser Gly
            125                 130                 135

GGG AAT GTG ACC ATC CAG TGT GAC TCA CAG GTG GCA TTT GAT GGC TTC       542
Gly Asn Val Thr Ile Gln Cys Asp Ser Gln Val Ala Phe Asp Gly Phe
        140                 145                 150

ATT CTG TGT AAG GAA GGA GAA GAT GAA CAC CCA CAA TGC CTG AAC TCC       590
Ile Leu Cys Lys Glu Gly Glu Asp Glu His Pro Gln Cys Leu Asn Ser
155                 160                 165                 170

CAT TCC CAT GCC CGT GGG TCA TCC CGG GCC ATC TTC TCC GTG GGC CCC       638
His Ser His Ala Arg Gly Ser Ser Arg Ala Ile Phe Ser Val Gly Pro
            175                 180                 185

GTG AGC CCA AGT CGC AGG TGG TCG TAC AGG TGC TAT GGT TAT GAC TCG       686
Val Ser Pro Ser Arg Arg Trp Ser Tyr Arg Cys Tyr Gly Tyr Asp Ser
        190                 195                 200

CGC GCT CCC TAT GTG TGG TCT CTA CCC AGT GAT CTC CTG GGG CTC CTG       734
Arg Ala Pro Tyr Val Trp Ser Leu Pro Ser Asp Leu Leu Gly Leu Leu
            205                 210                 215

GTC CCA GGT GTT TCT AAG AAG CCA TCA CTC TCA GTG CAG CCG GGT CCT       782
Val Pro Gly Val Ser Lys Lys Pro Ser Leu Ser Val Gln Pro Gly Pro
        220                 225                 230

GTC GTG GCC CCT GGG GAG AAG CTG ACC TTC CAG TGT GGC TCT GAT GCC       830
Val Val Ala Pro Gly Glu Lys Leu Thr Phe Gln Cys Gly Ser Asp Ala
235                 240                 245                 250

GGC TAC GAC AGA TTT GTT CTG TAC AAG GAG TGG GGA CGT GAC TTC CTC       878
Gly Tyr Asp Arg Phe Val Leu Tyr Lys Glu Trp Gly Arg Asp Phe Leu
            255                 260                 265

CAG CGC CCT GGC CGG CAG CCC CAG GCT GGG CTC TCC CAG GCC AAC TTC       926
Gln Arg Pro Gly Arg Gln Pro Gln Ala Gly Leu Ser Gln Ala Asn Phe
        270                 275                 280

ACC CTG GGC CCT GTG AGC CGC TCC TAC GGG GGC CAG TAC ACA TGC TCC       974
Thr Leu Gly Pro Val Ser Arg Ser Tyr Gly Gly Gln Tyr Thr Cys Ser
            285                 290                 295

GGT GCA TAC AAC CTC TCC TCC GAG TGG TCG GCC CCC AGC GAC CCC CTG      1022
Gly Ala Tyr Asn Leu Ser Ser Glu Trp Ser Ala Pro Ser Asp Pro Leu
        300                 305                 310

GAC ATC CTG ATC ACA GGA CAG ATC CGT GCC AGA CCC TTC CTC TCC GTG      1070
Asp Ile Leu Ile Thr Gly Gln Ile Arg Ala Arg Pro Phe Leu Ser Val
315                 320                 325                 330

CGG CCG GGC CCC ACA GTG GCC TCA GGA GAG AAC GTG ACC CTG CTG TGT      1118
Arg Pro Gly Pro Thr Val Ala Ser Gly Glu Asn Val Thr Leu Leu Cys
            335                 340                 345

CAG TCA CAG GGA GGG ATG CAC ACT TTC CTT TTG ACC AAG GAG GGG GCA      1166
Gln Ser Gln Gly Gly Met His Thr Phe Leu Leu Thr Lys Glu Gly Ala
        350                 355                 360

GCT GAT TCC CCG CTG CGT CTA AAA TCA AAG CGC CAA TCT CAT AAG TAC      1214
Ala Asp Ser Pro Leu Arg Leu Lys Ser Lys Arg Gln Ser His Lys Tyr
            365                 370                 375

CAG GCT GAA TTC CCC ATG AGT CCT GTG ACC TCG GCC CAC GCG GGG ACC      1262
Gln Ala Glu Phe Pro Met Ser Pro Val Thr Ser Ala His Ala Gly Thr
        380                 385                 390

TAC AGG TGC TAC GGC TCA CTC AGC TCC AAC CCC TAC CTG CTG ACT CAC      1310
Tyr Arg Cys Tyr Gly Ser Leu Ser Ser Asn Pro Tyr Leu Leu Thr His
395                 400                 405                 410

CCC AGT GAC CCC CTG GAG CTC GTG GTC TCA GGA GCA GCT GAG ACC CTC      1358
Pro Ser Asp Pro Leu Glu Leu Val Val Ser Gly Ala Ala Glu Thr Leu
            415                 420                 425
```

```
AGC CCA CCA CAA AAC AAG TCC GAC TCC AAG GCT GGT GAG TGAGGAGATG      1407
Ser Pro Pro Gln Asn Lys Ser Asp Ser Lys Ala Gly Glu
            430                     435

CTTGCCGTGA TGACGCTGGG CACAGAGGGT CAGGTCCTGT CAAGAGGAGC TGGGTGTCCT   1467

GGGTGGACAT TTGAAGAATT ATATTCATTC CAACTTGAAG AATTATTCAA CACCTTTAAC   1527

AATGTATATG TGAAGTACTT TATTCTTTCA TATTTTAAAA ATAAAGATA ATTATCCATG    1587

AAAAAAAAAA AAAAAAAAAA AAAGGGCGGC CGC                                 1620
```

(2) INFORMATION FOR SEQ ID NO: 12:

(i) SEQUENCE CHARACTERISTICS:
        (A) LENGTH: 439 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Thr Pro Ile Leu Thr Val Leu Ile Cys Leu Gly Leu Ser Leu Asp
 1               5                  10                  15

Pro Arg Thr His Val Gln Ala Gly Pro Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Ser Leu Glu Thr Gln Glu Tyr His Leu Tyr Arg Glu Lys
        50                  55                  60

Lys Thr Ala Leu Trp Ile Thr Arg Ile Pro Gln Glu Leu Val Lys Lys
 65                  70                  75                  80

Gly Gln Phe Pro Ile Leu Ser Ile Thr Trp Glu His Ala Gly Arg Tyr
                85                  90                  95

Cys Cys Ile Tyr Gly Ser His Thr Ala Gly Leu Ser Glu Ser Ser Asp
                100                 105                 110

Pro Leu Glu Leu Val Val Thr Gly Ala Tyr Ser Lys Pro Thr Leu Ser
            115                 120                 125

Ala Leu Pro Ser Pro Val Val Thr Ser Gly Gly Asn Val Thr Ile Gln
        130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Leu Val Pro Gly Val Ser Lys
    210                 215                 220

Lys Pro Ser Leu Ser Val Gln Pro Gly Pro Val Val Ala Pro Gly Glu
225                 230                 235                 240

Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285
```

```
Arg Ser Tyr Gly Gly Gln Tyr Thr Cys Ser Gly Ala Tyr Asn Leu Ser
    290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
    370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
                405                 410                 415

Leu Val Val Ser Gly Ala Ala Glu Thr Leu Ser Pro Pro Gln Asn Lys
            420                 425                 430

Ser Asp Ser Lys Ala Gly Glu
        435
```

(2) INFORMATION FOR SEQ ID NO: 13:

(i) SEQUENCE CHARACTERISTICS:
        (A) LENGTH: 2197 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 191..1483

(xi) SEQUENCE DESCRIPTION: SEQ ID NO: 13:

```
GTCGACCCAC GCGTCCGGTC AACTTTTCTT CCCCTACTTC CCTGCATTTC TCCTCTGTGC      60

TCACTGCCAC ACGCAGCTCA ACCTGGACGG CACAGCCAGA TGCGAGATGC GTCTCTGCTG     120

ATCTGAGTCT GCCTGCAGCA TGGACCTGGG TCTTCCCTGA AGCATCTCCA GGGCTGGAGG     180

GACGACTGCC ATG CAC CGA GGG CTC ATC CAT CCG CAG AGC AGG GCA GTG        229
            Met His Arg Gly Leu Ile His Pro Gln Ser Arg Ala Val
             1               5                  10

GGA GGA GAC GCC ATG ACC CCC ATC GTC ACA GTC CTG ATC TGT CTC GGG       277
Gly Gly Asp Ala Met Thr Pro Ile Val Thr Val Leu Ile Cys Leu Gly
 15                  20                  25

CTG AGT CTG GGC CCC AGG ACC CAC GTG CAG ACA GGG ACC ATC CCC AAG       325
Leu Ser Leu Gly Pro Arg Thr His Val Gln Thr Gly Thr Ile Pro Lys
 30                  35                  40                  45

CCC ACC CTG TGG GCT GAG CCA GAC TCT GTG ATC ACC CAG GGG AGT CCC       373
Pro Thr Leu Trp Ala Glu Pro Asp Ser Val Ile Thr Gln Gly Ser Pro
                 50                  55                  60

GTC ACC CTC AGT TGT CAG GGG AGC CTT GAA GCC CAG GAG TAC CGT CTA       421
Val Thr Leu Ser Cys Gln Gly Ser Leu Glu Ala Gln Glu Tyr Arg Leu
             65                  70                  75

TAT AGG GAG AAA AAA TCA GCA TCT TGG ATT ACA CGG ATA CGA CCA GAG       469
Tyr Arg Glu Lys Lys Ser Ala Ser Trp Ile Thr Arg Ile Arg Pro Glu
         80                  85                  90

CTT GTG AAG AAC GGC CAG TTC CAC ATC CCA TCC ATC ACC TGG GAA CAC       517
Leu Val Lys Asn Gly Gln Phe His Ile Pro Ser Ile Thr Trp Glu His
```

```
                    95                  100                 105
ACA GGG CGA TAT GGC TGT CAG TAT TAC AGC CGC GCT CGG TGG TCT GAG         565
Thr Gly Arg Tyr Gly Cys Gln Tyr Tyr Ser Arg Ala Arg Trp Ser Glu
110             115                 120                 125

CTC AGT GAC CCC CTG GTG CTG GTG ATG ACA GGA GCC TAC CCA AAA CCC         613
Leu Ser Asp Pro Leu Val Leu Val Met Thr Gly Ala Tyr Pro Lys Pro
                130                 135                 140

ACC CTC TCA GCC CAG CCC AGC CCT GTG GTG ACC TCA GGA GGA AGG GTG         661
Thr Leu Ser Ala Gln Pro Ser Pro Val Val Thr Ser Gly Gly Arg Val
            145                 150                 155

ACC CTC CAG TGT GAG TCA CAG GTG GCA TTT GGC GGC TTC ATT CTG TGT         709
Thr Leu Gln Cys Glu Ser Gln Val Ala Phe Gly Gly Phe Ile Leu Cys
        160                 165                 170

AAG GAA GGA GAA GAT GAA CAC CCA CAA TGC CTG AAC TCC CAG CCC CAT         757
Lys Glu Gly Glu Asp Glu His Pro Gln Cys Leu Asn Ser Gln Pro His
175                 180                 185

GCC CGT GGG TCG TCC CGC GCC ATC TTC TCC GTG GGC CCC GTG AGC CCG         805
Ala Arg Gly Ser Ser Arg Ala Ile Phe Ser Val Gly Pro Val Ser Pro
190                 195                 200                 205

AAT CGC AGG TGG TCG CAC AGG TGC TAT GGT TAT GAC TTG AAC TCT CCC         853
Asn Arg Arg Trp Ser His Arg Cys Tyr Gly Tyr Asp Leu Asn Ser Pro
                210                 215                 220

TAT GTG TGG TCT TCA CCC AGT GAT CTC CTG GAG CTC CTG GTC CCA GGT         901
Tyr Val Trp Ser Ser Pro Ser Asp Leu Leu Glu Leu Leu Val Pro Gly
            225                 230                 235

GTT TCT AAG AAG CCA TCA CTC TCA GTG CAG CCG GGT CCT GTC GTG GCC         949
Val Ser Lys Lys Pro Ser Leu Ser Val Gln Pro Gly Pro Val Val Ala
        240                 245                 250

CCT GGG GAA AGC CTG ACC CTC CAG TGT GTC TCT GAT GTC GGC TAT GAC         997
Pro Gly Glu Ser Leu Thr Leu Gln Cys Val Ser Asp Val Gly Tyr Asp
255                 260                 265

AGA TTT GTT CTG TAC AAG GAG GGG GAA CGT GAC CTT CGC CAG CTC CCT         1045
Arg Phe Val Leu Tyr Lys Glu Gly Glu Arg Asp Leu Arg Gln Leu Pro
270                 275                 280                 285

GGC CGG CAG CCC CAG GCT GGG CTC TCC CAG GCC AAC TTC ACC CTG GGC         1093
Gly Arg Gln Pro Gln Ala Gly Leu Ser Gln Ala Asn Phe Thr Leu Gly
                290                 295                 300

CCT GTG AGC CGC TCC TAC GGG GGC CAG TAC AGA TGC TAC GGT GCA TAC         1141
Pro Val Ser Arg Ser Tyr Gly Gly Gln Tyr Arg Cys Tyr Gly Ala Tyr
            305                 310                 315

AAC CTC TCC TCC GAG TGG TCG GCC CCC AGC GAC CCC CTG GAC ATC CTG         1189
Asn Leu Ser Ser Glu Trp Ser Ala Pro Ser Asp Pro Leu Asp Ile Leu
        320                 325                 330

ATC ACA GGA CAG ATC CAT GGC ACA CCC TTC ATC TCA GTG CAG CCA GGC         1237
Ile Thr Gly Gln Ile His Gly Thr Pro Phe Ile Ser Val Gln Pro Gly
335                 340                 345

CCC ACA GTG GCC TCA GGA GAG AAC GTG ACC CTG CTG TGT CAG TCA TGG         1285
Pro Thr Val Ala Ser Gly Glu Asn Val Thr Leu Leu Cys Gln Ser Trp
350                 355                 360                 365

CGG CAG TTC CAC ACT TTC CTT CTG ACC AAG GCG GGA GCA GCT GAT GCC         1333
Arg Gln Phe His Thr Phe Leu Leu Thr Lys Ala Gly Ala Ala Asp Ala
                370                 375                 380

CCA CTC CGT CTA AGA TCA ATA CAC GAA TAT CCT AAG TAC CAG GCT GAA         1381
Pro Leu Arg Leu Arg Ser Ile His Glu Tyr Pro Lys Tyr Gln Ala Glu
            385                 390                 395

TTC CCC ATG AGT CCT GTG ACC TCA GCC CAC GCG GGA ACC TAC AGG ACC         1429
Phe Pro Met Ser Pro Val Thr Ser Ala His Ala Gly Thr Tyr Arg Thr
        400                 405                 410

CTC CAT GGG TTC CAG CCC CCC ACC CAC GGT CCC ATC TCC ACC TGC              1477
```

```
Leu His Gly Phe Gln Pro Pro Thr His Arg Ser His Leu His Thr Cys
    415                 420                 425

AGG CCC TGAGGACCAG CCCCTCACCC CCACTGGGTC GGATCCCCAA AGTGGTCTGG        1533
Arg Pro
430

GAAGGCACCT GGGGGTTGTG ATCGGCATCT TGGTGGCCGT CGTCCTACTG CTCCTCCTCC    1593

TCCTCCTCCT CTTCCTCATC CTCCGACATC GACGTCAGGG CAAACACTGG ACATCGACCC    1653

AGAGAAAGGC TGATTTCCAA CATCCTGCAG GGGCTGTGGG GCCAGAGCCC ACAGACAGAG    1713

GCCTGCAGTG GAGGTCCAGC CCAGCTGCCG ACGCCCAGGA AGAAACCTC TATGCTGCCG     1773

TGAAGGACAC ACAGCCTGAA GATGGGGTGG AGATGGACAC TCGGGCTGCT GCATCTGAAG    1833

CCCCCCAGGA TGTGACCTAC GCCCAGCTGC ACAGCTTGAC CCTCAGACGG AAGGCAACTG    1893

AGCCTCCTCC ATCCCAGGAA AGGGAACCTC CAGCTGAGCC CAGCATTTAC GCCACCCTGG    1953

CCATCCACTA GCCCGGAGGG TACGCAGACT CCACACTCAG TAGAAGGAGA CTCAGGACTG    2013

CTGAAGGCAC GGGAGCTGCC CCCAGTGGAC ACCAATGAAC CCCAGTCAGC CTGGACCCCT    2073

AACAAAGACC ATGAGGAGAT GCTGGGAACT TTGGGACTCA CTTGATTCTG CAGTGGAAAT    2133

AACTAATATC CCTACATTTT TTAATTAAAG CAACAGACTT CTCAATAATC AATGAGTTAA    2193

CCGA                                                                 2197

(2) INFORMATION FOR SEQ ID NO: 14:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO: 14:

Met His Arg Gly Leu Ile His Pro Gln Ser Arg Ala Val Gly Gly Asp
 1               5                  10                  15

Ala Met Thr Pro Ile Val Thr Val Leu Ile Cys Leu Gly Leu Ser Leu
            20                  25                  30

Gly Pro Arg Thr His Val Gln Thr Gly Thr Ile Pro Lys Pro Thr Leu
        35                  40                  45

Trp Ala Glu Pro Asp Ser Val Ile Thr Gln Gly Ser Pro Val Thr Leu
    50                  55                  60

Ser Cys Gln Gly Ser Leu Glu Ala Gln Glu Tyr Arg Leu Tyr Arg Glu
65                  70                  75                  80

Lys Lys Ser Ala Ser Trp Ile Thr Arg Ile Arg Pro Glu Leu Val Lys
                85                  90                  95

Asn Gly Gln Phe His Ile Pro Ser Ile Thr Trp Glu His Thr Gly Arg
            100                 105                 110

Tyr Gly Cys Gln Tyr Tyr Ser Arg Ala Arg Trp Ser Glu Leu Ser Asp
        115                 120                 125

Pro Leu Val Leu Val Met Thr Gly Ala Tyr Pro Lys Pro Thr Leu Ser
    130                 135                 140

Ala Gln Pro Ser Pro Val Val Thr Ser Gly Gly Arg Val Thr Leu Gln
145                 150                 155                 160

Cys Glu Ser Gln Val Ala Phe Gly Gly Phe Ile Leu Cys Lys Glu Gly
                165                 170                 175

Glu Asp Glu His Pro Gln Cys Leu Asn Ser Gln Pro His Ala Arg Gly
            180                 185                 190
```

```
Ser Ser Arg Ala Ile Phe Ser Val Gly Pro Val Ser Pro Asn Arg Arg
        195                 200                 205

Trp Ser His Arg Cys Tyr Gly Tyr Asp Leu Asn Ser Pro Tyr Val Trp
        210                 215                 220

Ser Ser Pro Ser Asp Leu Leu Glu Leu Leu Val Pro Gly Val Ser Lys
225                 230                 235                 240

Lys Pro Ser Leu Ser Val Gln Pro Gly Pro Val Val Ala Pro Gly Glu
                245                 250                 255

Ser Leu Thr Leu Gln Cys Val Ser Asp Val Gly Tyr Asp Arg Phe Val
                260                 265                 270

Leu Tyr Lys Glu Gly Glu Arg Asp Leu Arg Gln Leu Pro Gly Arg Gln
            275                 280                 285

Pro Gln Ala Gly Leu Ser Gln Ala Asn Phe Thr Leu Gly Pro Val Ser
        290                 295                 300

Arg Ser Tyr Gly Gly Gln Tyr Arg Cys Tyr Gly Ala Tyr Asn Leu Ser
305                 310                 315                 320

Ser Glu Trp Ser Ala Pro Ser Asp Pro Leu Asp Ile Leu Ile Thr Gly
                325                 330                 335

Gln Ile His Gly Thr Pro Phe Ile Ser Val Gln Pro Gly Pro Thr Val
            340                 345                 350

Ala Ser Gly Glu Asn Val Thr Leu Leu Cys Gln Ser Trp Arg Gln Phe
        355                 360                 365

His Thr Phe Leu Leu Thr Lys Ala Gly Ala Ala Asp Ala Pro Leu Arg
        370                 375                 380

Leu Arg Ser Ile His Glu Tyr Pro Lys Tyr Gln Ala Glu Phe Pro Met
385                 390                 395                 400

Ser Pro Val Thr Ser Ala His Ala Gly Thr Tyr Arg Thr Leu His Gly
                405                 410                 415

Phe Gln Pro Pro Thr His Arg Ser His Leu His Thr Cys Arg Pro
            420                 425                 430

(2) INFORMATION FOR SEQ ID NO: 15:

(i) SEQUENCE CHARACTERISTICS:
        (A) LENGTH: 2271 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 191..2035

(xi) SEQUENCE DESCRIPTION: SEQ ID NO: 15:

GTCGACCCAC GCGTCCGGTC AACTTTTCTT CCCCTACTTC CCTGCATTTC TCCTCTGTGC      60

TCACTGCCAC ACGCAGCTCA ACCTGGACGG CACAGCCAGA TGCGAGATGC GTCTCTGCTG     120

ATCTGAGTCT GCCTGCAGCA TGGACCTGGG TCTTCCCTGA AGCATCTCCA GGGCTGGAGG     180

GACGACTGCC ATG CAC CGA GGG CTC ATC CAT CCG CAG AGC AGG GCA GTG        229
            Met His Arg Gly Leu Ile His Pro Gln Ser Arg Ala Val
              1               5                  10

GGA GGA GAC GCC ATG ACC CCC ATC GTC ACA GTC CTG ATC TGT CTC GGG       277
Gly Gly Asp Ala Met Thr Pro Ile Val Thr Val Leu Ile Cys Leu Gly
 15                  20                  25

CTG AGT CTG GGC CCC AGG ACC CAC GTG CAG ACA GGG ACC ATC CCC AAG       325
Leu Ser Leu Gly Pro Arg Thr His Val Gln Thr Gly Thr Ile Pro Lys
 30                  35                  40                  45
```

-continued

| | |
|---|---|
| CCC ACC CTG TGG GCT GAG CCA GAC TCT GTG ATC ACC CAG GGG AGT CCC<br>Pro Thr Leu Trp Ala Glu Pro Asp Ser Val Ile Thr Gln Gly Ser Pro<br>                50                      55                      60 | 373 |
| GTC ACC CTC AGT TGT CAG GGG AGC CTT GAA GCC CAG GAG TAC CGT CTA<br>Val Thr Leu Ser Cys Gln Gly Ser Leu Glu Ala Gln Glu Tyr Arg Leu<br>                65                      70                      75 | 421 |
| TAT AGG GAG AAA AAA TCA GCA TCT TGG ATT ACA CGG ATA CGA CCA GAG<br>Tyr Arg Glu Lys Lys Ser Ala Ser Trp Ile Thr Arg Ile Arg Pro Glu<br>                80                      85                      90 | 469 |
| CTT GTG AAG AAC GGC CAG TTC CAC ATC CCA TCC ATC ACC TGG GAA CAC<br>Leu Val Lys Asn Gly Gln Phe His Ile Pro Ser Ile Thr Trp Glu His<br>     95                     100                    105 | 517 |
| ACA GGG CGA TAT GGC TGT CAG TAT TAC AGC CGC GCT CGG TGG TCT GAG<br>Thr Gly Arg Tyr Gly Cys Gln Tyr Tyr Ser Arg Ala Arg Trp Ser Glu<br>110                  115                    120                  125 | 565 |
| CTC AGT GAC CCC CTG GTG CTG GTG ATG ACA GGA GCC TAC CCA AAA CCC<br>Leu Ser Asp Pro Leu Val Leu Val Met Thr Gly Ala Tyr Pro Lys Pro<br>               130                    135                    140 | 613 |
| ACC CTC TCA GCC CAG CCC AGC CCT GTG GTG ACC TCA GGA GGA AGG GTG<br>Thr Leu Ser Ala Gln Pro Ser Pro Val Val Thr Ser Gly Gly Arg Val<br>           145                    150                    155 | 661 |
| ACC CTC CAG TGT GAG TCA CAG GTG GCA TTT GGC GGC TTC ATT CTG TGT<br>Thr Leu Gln Cys Glu Ser Gln Val Ala Phe Gly Gly Phe Ile Leu Cys<br>           160                    165                    170 | 709 |
| AAG GAA GGA GAA GAT GAA CAC CCA CAA TGC CTG AAC TCC CAG CCC CAT<br>Lys Glu Gly Glu Asp Glu His Pro Gln Cys Leu Asn Ser Gln Pro His<br>175                  180                    185 | 757 |
| GCC CGT GGG TCG TCC CGC GCC ATC TTC TCC GTG GGC CCC GTG AGC CCG<br>Ala Arg Gly Ser Ser Arg Ala Ile Phe Ser Val Gly Pro Val Ser Pro<br>190                  195                    200                  205 | 805 |
| AAT CGC AGG TGG TCG CAC AGG TGC TAT GGT TAT GAC TTG AAC TCT CCC<br>Asn Arg Arg Trp Ser His Arg Cys Tyr Gly Tyr Asp Leu Asn Ser Pro<br>               210                    215                    220 | 853 |
| TAT GTG TGG TCT TCA CCC AGT GAT CTC CTG GAG CTC CTG GTC CCA GGT<br>Tyr Val Trp Ser Ser Pro Ser Asp Leu Leu Glu Leu Leu Val Pro Gly<br>           225                    230                    235 | 901 |
| GTT TCT AAG AAG CCA TCA CTC TCA GTG CAG CCG GGT CCT GTC GTG GCC<br>Val Ser Lys Lys Pro Ser Leu Ser Val Gln Pro Gly Pro Val Val Ala<br>           240                    245                    250 | 949 |
| CCT GGG GAA AGC CTG ACC CTC CAG TGT GTC TCT GAT GTC GGC TAT GAC<br>Pro Gly Glu Ser Leu Thr Leu Gln Cys Val Ser Asp Val Gly Tyr Asp<br>255                  260                    265 | 997 |
| AGA TTT GTT CTG TAC AAG GAG GGG GAA CGT GAC CTT CGC CAG CTC CCT<br>Arg Phe Val Leu Tyr Lys Glu Gly Glu Arg Asp Leu Arg Gln Leu Pro<br>270                  275                    280                  285 | 1045 |
| GGC CGG CAG CCC CAG GCT GGG CTC TCC CAG GCC AAC TTC ACC CTG GGC<br>Gly Arg Gln Pro Gln Ala Gly Leu Ser Gln Ala Asn Phe Thr Leu Gly<br>               290                    295                    300 | 1093 |
| CCT GTG AGC CGC TCC TAC GGG GGC CAG TAC AGA TGC TAC GGT GCA TAC<br>Pro Val Ser Arg Ser Tyr Gly Gly Gln Tyr Arg Cys Tyr Gly Ala Tyr<br>           305                    310                    315 | 1141 |
| AAC CTC TCC TCC GAG TGG TCG GCC CCC AGC GAC CCC CTG GAC ATC CTG<br>Asn Leu Ser Ser Glu Trp Ser Ala Pro Ser Asp Pro Leu Asp Ile Leu<br>           320                    325                    330 | 1189 |
| ATC ACA GGA CAG ATC CAT GGC ACA CCC TTC ATC TCA GTG CAG CCA GGC<br>Ile Thr Gly Gln Ile His Gly Thr Pro Phe Ile Ser Val Gln Pro Gly<br>           335                    340                    345 | 1237 |
| CCC ACA GTG GCC TCA GGA GAG AAC GTG ACC CTG CTG TGT CAG TCA TGG<br>Pro Thr Val Ala Ser Gly Glu Asn Val Thr Leu Leu Cys Gln Ser Trp | 1285 |

-continued

```
350              355              360              365
CGG CAG TTC CAC ACT TTC CTT CTG ACC AAG GCG GGA GCA GCT GAT GCC      1333
Arg Gln Phe His Thr Phe Leu Leu Thr Lys Ala Gly Ala Ala Asp Ala
            370              375              380

CCA CTC CGT CTA AGA TCA ATA CAC GAA TAT CCT AAG TAC CAG GCT GAA      1381
Pro Leu Arg Leu Arg Ser Ile His Glu Tyr Pro Lys Tyr Gln Ala Glu
            385              390              395

TTC CCC ATG AGT CCT GTG ACC TCA GCC CAC GCG GGG ACC TAC AGG TGC      1429
Phe Pro Met Ser Pro Val Thr Ser Ala His Ala Gly Thr Tyr Arg Cys
            400              405              410

TAC GGC TCA CTC AAC TCC GAC CCC TAC CTG CTG TCT CAC CCC AGT GAG      1477
Tyr Gly Ser Leu Asn Ser Asp Pro Tyr Leu Leu Ser His Pro Ser Glu
        415              420              425

CCC CTG GAG CTC GTG GTC TCA GGA CCC TCC ATG GGT TCC AGC CCC CCA      1525
Pro Leu Glu Leu Val Val Ser Gly Pro Ser Met Gly Ser Ser Pro Pro
430              435              440              445

CCC ACC GGT CCC ATC TCC ACA CCT GCA GGC CCT GAG GAC CAG CCC CTC      1573
Pro Thr Gly Pro Ile Ser Thr Pro Ala Gly Pro Glu Asp Gln Pro Leu
                450              455              460

ACC CCC ACT GGG TCG GAT CCC CAA AGT GGT CTG GGA AGG CAC CTG GGG      1621
Thr Pro Thr Gly Ser Asp Pro Gln Ser Gly Leu Gly Arg His Leu Gly
            465              470              475

GTT GTG ATC GGC ATC TTG GTG GCC GTC GTC CTA CTG CTC CTC CTC CTC      1669
Val Val Ile Gly Ile Leu Val Ala Val Val Leu Leu Leu Leu Leu Leu
            480              485              490

CTC CTC CTC TTC CTC ATC CTC CGA CAT CGA CGT CAG GGC AAA CAC TGG      1717
Leu Leu Leu Phe Leu Ile Leu Arg His Arg Arg Gln Gly Lys His Trp
        495              500              505

ACA TCG ACC CAG AGA AAG GCT GAT TTC CAA CAT CCT GCA GGG GCT GTG      1765
Thr Ser Thr Gln Arg Lys Ala Asp Phe Gln His Pro Ala Gly Ala Val
510              515              520              525

GGG CCA GAG CCC ACA GAC AGA GGC CTG CAG TGG AGG TCC AGC CCA GCT      1813
Gly Pro Glu Pro Thr Asp Arg Gly Leu Gln Trp Arg Ser Ser Pro Ala
            530              535              540

GCC GAC GCC CAG GAA GAA AAC CTC TAT GCT GCC GTG AAG GAC ACA CAG      1861
Ala Asp Ala Gln Glu Glu Asn Leu Tyr Ala Ala Val Lys Asp Thr Gln
            545              550              555

CCT GAA GAT GGG GTG GAG ATG GAC ACT CGG GCT GCT GCA TCT GAA GCC      1909
Pro Glu Asp Gly Val Glu Met Asp Thr Arg Ala Ala Ala Ser Glu Ala
            560              565              570

CCC CAG GAT GTG ACC TAC GCC CAG CTG CAC AGC TTG ACC CTC AGA CGG      1957
Pro Gln Asp Val Thr Tyr Ala Gln Leu His Ser Leu Thr Leu Arg Arg
        575              580              585

AAG GCA ACT GAG CCT CCT CCA TCC CAG GAA AGG GAA CCT CCA GCT GAG      2005
Lys Ala Thr Glu Pro Pro Pro Ser Gln Glu Arg Glu Pro Pro Ala Glu
590              595              600              605

CCC AGC ATT TAC GCC ACC CTG GCC ATC CAC TAGCCCGGAG GGTACGCAGA       2055
Pro Ser Ile Tyr Ala Thr Leu Ala Ile His
                610              615

CTCCACACTC AGTAGAAGGA GACTCAGGAC TGCTGAAGGC ACGGGAGCTG CCCCCAGTGG    2115

ACACCAATGA ACCCCAGTCA GCCTGGACCC CTAACAAAGA CCATGAGGAG ATGCTGGGAA    2175

CTTTGGGACT CACTTGATTC TGCAGTGGAA ATAACTAATA TCCCTACATT TTTTAATTAA    2235

AGCAACAGAC TTCTCAATAA TCAATGAGTT AACCGA                              2271
```

(2) INFORMATION FOR SEQ ID NO: 16:

(i) SEQUENCE CHARACTERISTICS:
        (A) LENGTH: 615 amino acids

-continued

```
      (B) TYPE: amino acid
      (D) TOPOLOGY: linear (ii) MOLECULE TYPE: protein (xi) SEQUENCE DESCRIPTION: SEQ ID NO: 16:

Met His Arg Gly Leu Ile His Pro Gln Ser Arg Ala Val Gly Gly Asp
 1               5                  10                  15

Ala Met Thr Pro Ile Val Thr Val Leu Ile Cys Leu Gly Leu Ser Leu
                20                  25                  30

Gly Pro Arg Thr His Val Gln Thr Gly Thr Ile Pro Lys Pro Thr Leu
            35                  40                  45

Trp Ala Glu Pro Asp Ser Val Ile Thr Gln Gly Ser Pro Val Thr Leu
 50                  55                  60

Ser Cys Gln Gly Ser Leu Glu Ala Gln Glu Tyr Arg Leu Tyr Arg Glu
 65                  70                  75                  80

Lys Lys Ser Ala Ser Trp Ile Thr Arg Ile Arg Pro Glu Leu Val Lys
                85                  90                  95

Asn Gly Gln Phe His Ile Pro Ser Ile Thr Trp Glu His Thr Gly Arg
            100                 105                 110

Tyr Gly Cys Gln Tyr Tyr Ser Arg Ala Arg Trp Ser Glu Leu Ser Asp
        115                 120                 125

Pro Leu Val Leu Val Met Thr Gly Ala Tyr Pro Lys Pro Thr Leu Ser
130                 135                 140

Ala Gln Pro Ser Pro Val Val Thr Ser Gly Gly Arg Val Thr Leu Gln
145                 150                 155                 160

Cys Glu Ser Gln Val Ala Phe Gly Gly Phe Ile Leu Cys Lys Glu Gly
                165                 170                 175

Glu Asp Glu His Pro Gln Cys Leu Asn Ser Gln Pro His Ala Arg Gly
            180                 185                 190

Ser Ser Arg Ala Ile Phe Ser Val Gly Pro Val Ser Pro Asn Arg Arg
        195                 200                 205

Trp Ser His Arg Cys Tyr Gly Tyr Asp Leu Asn Ser Pro Tyr Val Trp
    210                 215                 220

Ser Ser Pro Ser Asp Leu Leu Glu Leu Leu Val Pro Gly Val Ser Lys
225                 230                 235                 240

Lys Pro Ser Leu Ser Val Gln Pro Gly Pro Val Val Ala Pro Gly Glu
                245                 250                 255

Ser Leu Thr Leu Gln Cys Val Ser Asp Val Gly Tyr Asp Arg Phe Val
            260                 265                 270

Leu Tyr Lys Glu Gly Glu Arg Asp Leu Arg Gln Leu Pro Gly Arg Gln
        275                 280                 285

Pro Gln Ala Gly Leu Ser Gln Ala Asn Phe Thr Leu Gly Pro Val Ser
290                 295                 300

Arg Ser Tyr Gly Gly Gln Tyr Arg Cys Tyr Gly Ala Tyr Asn Leu Ser
305                 310                 315                 320

Ser Glu Trp Ser Ala Pro Ser Asp Pro Leu Asp Ile Leu Ile Thr Gly
                325                 330                 335

Gln Ile His Gly Thr Pro Phe Ile Ser Val Gln Pro Gly Pro Thr Val
            340                 345                 350

Ala Ser Gly Glu Asn Val Thr Leu Leu Cys Gln Ser Trp Arg Gln Phe
        355                 360                 365

His Thr Phe Leu Leu Thr Lys Ala Gly Ala Ala Asp Ala Pro Leu Arg
370                 375                 380
```

-continued

```
Leu Arg Ser Ile His Glu Tyr Pro Lys Tyr Gln Ala Glu Phe Pro Met
385                 390                 395                 400

Ser Pro Val Thr Ser Ala His Ala Gly Thr Tyr Arg Cys Tyr Gly Ser
            405                 410                 415

Leu Asn Ser Asp Pro Tyr Leu Leu Ser His Pro Ser Glu Pro Leu Glu
            420                 425                 430

Leu Val Val Ser Gly Pro Ser Met Gly Ser Ser Pro Pro Thr Gly
        435                 440                 445

Pro Ile Ser Thr Pro Ala Gly Pro Glu Asp Gln Pro Leu Thr Pro Thr
    450                 455                 460

Gly Ser Asp Pro Gln Ser Gly Leu Gly Arg His Leu Gly Val Val Ile
465                 470                 475                 480

Gly Ile Leu Val Ala Val Val Leu Leu Leu Leu Leu Leu Leu Leu Leu
            485                 490                 495

Phe Leu Ile Leu Arg His Arg Arg Gln Gly Lys His Trp Thr Ser Thr
            500                 505                 510

Gln Arg Lys Ala Asp Phe Gln His Pro Ala Gly Ala Val Gly Pro Glu
    515                 520                 525

Pro Thr Asp Arg Gly Leu Gln Trp Arg Ser Ser Pro Ala Ala Asp Ala
    530                 535                 540

Gln Glu Glu Asn Leu Tyr Ala Ala Val Lys Asp Thr Gln Pro Glu Asp
545                 550                 555                 560

Gly Val Glu Met Asp Thr Arg Ala Ala Ala Ser Glu Ala Pro Gln Asp
                565                 570                 575

Val Thr Tyr Ala Gln Leu His Ser Leu Thr Leu Arg Arg Lys Ala Thr
            580                 585                 590

Glu Pro Pro Pro Ser Gln Glu Arg Glu Pro Pro Ala Glu Pro Ser Ile
        595                 600                 605

Tyr Ala Thr Leu Ala Ile His
        610                 615
```

(2) INFORMATION FOR SEQ ID NO: 17:

(i) SEQUENCE CHARACTERISTICS:
        (A) LENGTH: 2388 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 180..2024

(xi) SEQUENCE DESCRIPTION: SEQ ID NO: 17:

```
AAAGAAGTCA ACTTTTCTTC CCCTACTTCC CTGCATTTCT CCTCTGTGCT CACTGCCACA      60

CGCAGCTCAA CCTGGACGGC ACAGCCAGAT GCGAGATGCG TCTCTGCTGA TCTGAGTCTG     120

CCTGCAGCAT GGACCTGGGT CTTCCCTGAA GCATCTCCAG GGCTGGAGGG ACGACTGCC     179

ATG CAC CGA GGG CTC ATC CAT CCG CAG AGC AGG GCA GTG GGA GGA GAC     227
Met His Arg Gly Leu Ile His Pro Gln Ser Arg Ala Val Gly Gly Asp
  1               5                  10                  15

GCC ATG ACC CCC ATC GTC ACA GTC CTG ATC TGT CTC GGG CTG AGT CTG     275
Ala Met Thr Pro Ile Val Thr Val Leu Ile Cys Leu Gly Leu Ser Leu
             20                  25                  30

GGC CCC AGG ACC CAC GTG CAG ACA GGG ACC ATC CCC AAG CCC ACC CTG     323
Gly Pro Arg Thr His Val Gln Thr Gly Thr Ile Pro Lys Pro Thr Leu
         35                  40                  45
```

-continued

```
TGG GCT GAG CCA GAC TCT GTG ATC ACC CAG GGG AGT CCC GTC ACC CTC         371
Trp Ala Glu Pro Asp Ser Val Ile Thr Gln Gly Ser Pro Val Thr Leu
    50              55                  60

AGT TGT CAG GGG AGC CTT GAA GCC CAG GAG TAC CGT CTA TAT AGG GAG         419
Ser Cys Gln Gly Ser Leu Glu Ala Gln Glu Tyr Arg Leu Tyr Arg Glu
65              70                  75                  80

AAA AAA TCA GCA TCT TGG ATT ACA CGG ATA CGA CCA GAG CTT GTG AAG         467
Lys Lys Ser Ala Ser Trp Ile Thr Arg Ile Arg Pro Glu Leu Val Lys
                85                  90                  95

AAC GGC CAG TTC CAC ATC CCA TCC ATC ACC TGG GAA CAC ACA GGG CGA         515
Asn Gly Gln Phe His Ile Pro Ser Ile Thr Trp Glu His Thr Gly Arg
                    100                 105                 110

TAT GGC TGT CAG TAT TAC AGC CGC GCT CGG TGG TCT GAG CTC AGT GAC         563
Tyr Gly Cys Gln Tyr Tyr Ser Arg Ala Arg Trp Ser Glu Leu Ser Asp
                115                 120                 125

CCC CTG GTG CTG GTG ATG ACA GGA GCC TAC CCA AAA CCC ACC CTC TCA         611
Pro Leu Val Leu Val Met Thr Gly Ala Tyr Pro Lys Pro Thr Leu Ser
130                 135                 140

GCC CAG CCC AGC CCT GTG GTG ACC TCA GGA GGA AGG GTG ACC CTC CAG         659
Ala Gln Pro Ser Pro Val Val Thr Ser Gly Gly Arg Val Thr Leu Gln
145                 150                 155                 160

TGT GAG TCA CAG GTG GCA TTT GGC GGC TTC ATT CTG TGT AAG GAA GGA         707
Cys Glu Ser Gln Val Ala Phe Gly Gly Phe Ile Leu Cys Lys Glu Gly
                165                 170                 175

GAA GAT GAA CAC CCA CAA TGC CTG AAC TCC CAG CCC CAT GCC CGT GGG         755
Glu Asp Glu His Pro Gln Cys Leu Asn Ser Gln Pro His Ala Arg Gly
                180                 185                 190

TCG TCC CGC GCC ATC TTC TCC GTG GGC CCC GTG AGC CCG AAT CGC AGG         803
Ser Ser Arg Ala Ile Phe Ser Val Gly Pro Val Ser Pro Asn Arg Arg
                195                 200                 205

TGG TCG CAC AGG TGC TAT GGT TAT GAC TTG AAC TCT CCC TAT GTG TGG         851
Trp Ser His Arg Cys Tyr Gly Tyr Asp Leu Asn Ser Pro Tyr Val Trp
210                 215                 220

TCT TCA CCC AGT GAT CTC CTG GAG CTC CTG GTC CCA GGT GTT TCT AAG         899
Ser Ser Pro Ser Asp Leu Leu Glu Leu Leu Val Pro Gly Val Ser Lys
225                 230                 235                 240

AAG CCA TCA CTC TCA GTG CAG CCG GGT CCT GTC GTG GCC CCT GGG GAA         947
Lys Pro Ser Leu Ser Val Gln Pro Gly Pro Val Val Ala Pro Gly Glu
                245                 250                 255

AGC CTG ACC CTC CAG TGT GTC TCT GAT GTC GGC TAT GAC AGA TTT GTT         995
Ser Leu Thr Leu Gln Cys Val Ser Asp Val Gly Tyr Asp Arg Phe Val
                260                 265                 270

CTG TAC AAG GAG GGG GAA CGT GAC CTT CGC CAG CTC CCT GGC CGG CAG        1043
Leu Tyr Lys Glu Gly Glu Arg Asp Leu Arg Gln Leu Pro Gly Arg Gln
            275                 280                 285

CCC CAG GCT GGG CTC TCC CAG GCC AAC TTC ACC CTG GGC CCT GTG AGC        1091
Pro Gln Ala Gly Leu Ser Gln Ala Asn Phe Thr Leu Gly Pro Val Ser
290                 295                 300

CGC TCC TAC GGG GGC CAG TAC AGA TGC TAC GGT GCA TAC AAC CTC TCC        1139
Arg Ser Tyr Gly Gly Gln Tyr Arg Cys Tyr Gly Ala Tyr Asn Leu Ser
305                 310                 315                 320

TCC GAG TGG TCG GCC CCC AGC GAC CCC CTG GAC ATC CTG ATC ACA GGA        1187
Ser Glu Trp Ser Ala Pro Ser Asp Pro Leu Asp Ile Leu Ile Thr Gly
                325                 330                 335

CAG ATC CAT GGC ACA CCC TTC ATC TCA GTG CAG CCA GGC CCC ACA GTG        1235
Gln Ile His Gly Thr Pro Phe Ile Ser Val Gln Pro Gly Pro Thr Val
                340                 345                 350

GCC TCA GGA GAG AAC GTG ACC CTG CTG TGT CAG TCA TGG CGG CAG TTC        1283
Ala Ser Gly Glu Asn Val Thr Leu Leu Cys Gln Ser Trp Arg Gln Phe
```

-continued

```
                355                     360                     365
CAC ACT TTC CTT CTG ACC AAG GCG GGA GCA GCT GAT GCC CCA CTC CGT       1331
His Thr Phe Leu Leu Thr Lys Ala Gly Ala Ala Asp Ala Pro Leu Arg
        370                 375                 380

CTA AGA TCA ATA CAC GAA TAT CCT AAG TAC CAG GCT GAA TTC CCC ATG       1379
Leu Arg Ser Ile His Glu Tyr Pro Lys Tyr Gln Ala Glu Phe Pro Met
385                 390                 395                 400

AGT CCC GTG ACC TCA GCC CAC GCG GGG ACC TAC AGG TGC TAC GGC TCA       1427
Ser Pro Val Thr Ser Ala His Ala Gly Thr Tyr Arg Cys Tyr Gly Ser
                405                 410                 415

CTC AAC TCC GAC CCC TAC CTG CTG TCT CAC CCC AGT GAG CCC CTG GAG       1475
Leu Asn Ser Asp Pro Tyr Leu Leu Ser His Pro Ser Glu Pro Leu Glu
            420                 425                 430

CTC GTG GTC TCA GGA CCC TCC ATG GGT TCC AGC CCC CCA CCC ACC GGT       1523
Leu Val Val Ser Gly Pro Ser Met Gly Ser Ser Pro Pro Pro Thr Gly
        435                 440                 445

CCC ATC TCC ACA CCT GCA GGC CCT GAG GAC CAG CCC CTC ACC CCC ACT       1571
Pro Ile Ser Thr Pro Ala Gly Pro Glu Asp Gln Pro Leu Thr Pro Thr
    450                 455                 460

GGG TCG GAT CCC CAA AGT GGT CTG GGA AGG CAC CTG GGG GTT GTG ATC       1619
Gly Ser Asp Pro Gln Ser Gly Leu Gly Arg His Leu Gly Val Val Ile
465                 470                 475                 480

GGC ATC TTG GTG GCC GTC GTC CTA CTG CTC CTC CTC CTC CTC CTC CTC       1667
Gly Ile Leu Val Ala Val Val Leu Leu Leu Leu Leu Leu Leu Leu Leu
                485                 490                 495

TTC CTC ATC CTC CGA CAT CGA CGT CAG GGC AAA CAC TGG ACA TCG ACC       1715
Phe Leu Ile Leu Arg His Arg Arg Gln Gly Lys His Trp Thr Ser Thr
            500                 505                 510

CAG AGA AAG GCT GAT TTC CAA CAT CCT GCA GGG GCT GTG GGG CCA GAG       1763
Gln Arg Lys Ala Asp Phe Gln His Pro Ala Gly Ala Val Gly Pro Glu
        515                 520                 525

CCC ACA GAC AGA GGC CTG CAG TGG AGG TCC AGC CCA GCT GCC GAC GCC       1811
Pro Thr Asp Arg Gly Leu Gln Trp Arg Ser Ser Pro Ala Ala Asp Ala
    530                 535                 540

CAG GAA GAA AAC CTC TAT GCT GCC GTG AAG GAC ACA CAG CCT GAA GAT       1859
Gln Glu Glu Asn Leu Tyr Ala Ala Val Lys Asp Thr Gln Pro Glu Asp
545                 550                 555                 560

GGG GTG GAG ATG GAC ACT CGG GCT GCT GCA TCT GAA GCC CCC CAG GAT       1907
Gly Val Glu Met Asp Thr Arg Ala Ala Ala Ser Glu Ala Pro Gln Asp
                565                 570                 575

GTG ACC TAC GCC CAG CTG CAC AGC TTG ACC CTC AGA CGG AAG GCA ACT       1955
Val Thr Tyr Ala Gln Leu His Ser Leu Thr Leu Arg Arg Lys Ala Thr
            580                 585                 590

GAG CCT CCT CCA TCC CAG GAA AGG GAA CCT CCA GCT GAG CCC AGC ATC       2003
Glu Pro Pro Pro Ser Gln Glu Arg Glu Pro Pro Ala Glu Pro Ser Ile
        595                 600                 605

TAC GCC ACC CTG GCC ATC CAC TAGCCCGGAG GGTACGCAGA CTCCACACTC          2054
Tyr Ala Thr Leu Ala Ile His
    610                 615

AGTAGAAGGA GACTCAGGAC TGCTGAAGGC ACGGGAGCTG CCCCCAGTGG ACACCAATGA    2114

ACCCCAGTCA GCCTGGACCC CTAACAAAGA CCATGAGGAG ATGCTGGGAA CTTTGGGACT    2174

CACTTGATTC TGCAGTCGAA ATAACTAATA TCCCTACATT TTTTAATTAA AGCAACAGAC    2234

TTCTCAATAA TCAATGAGTT AACCGAGAAA ACTAAAATCA GAAGTAAGAA TGTGCTTTAA    2294

ACTGAATCAC AATATAAATA TTACACATCA CACAATGAAA TTGAAAAAGT ACAAACCACA    2354

AATGAAAAAA GTAGAAACGA AAAAAAAAAA AAAA                                2388
```

(2) INFORMATION FOR SEQ ID NO: 18:

(i) SEQUENCE CHARACTERISTICS:
        (A) LENGTH: 615 amino acids
        (B) TYPE: amino acid
        (D) TOPOLOGY: linear (ii) MOLECULE TYPE: protein (xi) SEQUENCE DESCRIPTION: SEQ ID NO: 18:

```
Met His Arg Gly Leu Ile His Pro Gln Ser Arg Ala Val Gly Gly Asp
 1               5                  10                  15

Ala Met Thr Pro Ile Val Thr Val Leu Ile Cys Leu Gly Leu Ser Leu
             20                  25                  30

Gly Pro Arg Thr His Val Gln Thr Gly Thr Ile Pro Lys Pro Thr Leu
         35                  40                  45

Trp Ala Glu Pro Asp Ser Val Ile Thr Gln Gly Ser Pro Val Thr Leu
     50                  55                  60

Ser Cys Gln Gly Ser Leu Glu Ala Gln Glu Tyr Arg Leu Tyr Arg Glu
 65                  70                  75                  80

Lys Lys Ser Ala Ser Trp Ile Thr Arg Ile Arg Pro Glu Leu Val Lys
                 85                  90                  95

Asn Gly Gln Phe His Ile Pro Ser Ile Thr Trp Glu His Thr Gly Arg
            100                 105                 110

Tyr Gly Cys Gln Tyr Tyr Ser Arg Ala Arg Trp Ser Glu Leu Ser Asp
        115                 120                 125

Pro Leu Val Leu Val Met Thr Gly Ala Tyr Pro Lys Pro Thr Leu Ser
    130                 135                 140

Ala Gln Pro Ser Pro Val Val Thr Ser Gly Gly Arg Val Thr Leu Gln
145                 150                 155                 160

Cys Glu Ser Gln Val Ala Phe Gly Gly Phe Ile Leu Cys Lys Glu Gly
                165                 170                 175

Glu Asp Glu His Pro Gln Cys Leu Asn Ser Gln Pro His Ala Arg Gly
            180                 185                 190

Ser Ser Arg Ala Ile Phe Ser Val Gly Pro Val Ser Pro Asn Arg Arg
        195                 200                 205

Trp Ser His Arg Cys Tyr Gly Tyr Asp Leu Asn Ser Pro Tyr Val Trp
    210                 215                 220

Ser Ser Pro Ser Asp Leu Leu Glu Leu Leu Val Pro Gly Val Ser Lys
225                 230                 235                 240

Lys Pro Ser Leu Ser Val Gln Pro Gly Pro Val Val Ala Pro Gly Glu
                245                 250                 255

Ser Leu Thr Leu Gln Cys Val Ser Asp Val Gly Tyr Asp Arg Phe Val
            260                 265                 270

Leu Tyr Lys Glu Gly Glu Arg Asp Leu Arg Gln Leu Pro Gly Arg Gln
        275                 280                 285

Pro Gln Ala Gly Leu Ser Gln Ala Asn Phe Thr Leu Gly Pro Val Ser
    290                 295                 300

Arg Ser Tyr Gly Gly Gln Tyr Arg Cys Tyr Gly Ala Tyr Asn Leu Ser
305                 310                 315                 320

Ser Glu Trp Ser Ala Pro Ser Asp Pro Leu Asp Ile Leu Ile Thr Gly
                325                 330                 335

Gln Ile His Gly Thr Pro Phe Ile Ser Val Gln Pro Gly Pro Thr Val
            340                 345                 350

Ala Ser Gly Glu Asn Val Thr Leu Leu Cys Gln Ser Trp Arg Gln Phe
        355                 360                 365
```

```
His Thr Phe Leu Leu Thr Lys Ala Gly Ala Ala Asp Ala Pro Leu Arg
    370                 375                 380
Leu Arg Ser Ile His Glu Tyr Pro Lys Tyr Gln Ala Glu Phe Pro Met
385                 390                 395                 400
Ser Pro Val Thr Ser Ala His Ala Gly Thr Tyr Arg Cys Tyr Gly Ser
                405                 410                 415
Leu Asn Ser Asp Pro Tyr Leu Leu Ser His Pro Ser Glu Pro Leu Glu
                420                 425                 430
Leu Val Val Ser Gly Pro Ser Met Gly Ser Pro Pro Thr Gly
            435                 440                 445
Pro Ile Ser Thr Pro Ala Gly Pro Glu Asp Gln Pro Leu Thr Pro Thr
    450                 455                 460
Gly Ser Asp Pro Gln Ser Gly Leu Gly Arg His Leu Gly Val Val Ile
465                 470                 475                 480
Gly Ile Leu Val Ala Val Val Leu Leu Leu Leu Leu Leu Leu Leu Leu
                485                 490                 495
Phe Leu Ile Leu Arg His Arg Arg Gln Gly Lys His Trp Thr Ser Thr
                500                 505                 510
Gln Arg Lys Ala Asp Phe Gln His Pro Ala Gly Ala Val Gly Pro Glu
    515                 520                 525
Pro Thr Asp Arg Gly Leu Gln Trp Arg Ser Ser Pro Ala Ala Asp Ala
    530                 535                 540
Gln Glu Glu Asn Leu Tyr Ala Ala Val Lys Asp Thr Gln Pro Glu Asp
545                 550                 555                 560
Gly Val Glu Met Asp Thr Arg Ala Ala Ala Ser Glu Ala Pro Gln Asp
                565                 570                 575
Val Thr Tyr Ala Gln Leu His Ser Leu Thr Leu Arg Arg Lys Ala Thr
                580                 585                 590
Glu Pro Pro Pro Ser Gln Glu Arg Glu Pro Pro Ala Glu Pro Ser Ile
                595                 600                 605
Tyr Ala Thr Leu Ala Ile His
    610                 615

(2) INFORMATION FOR SEQ ID NO: 19:

(i) SEQUENCE CHARACTERISTICS:
        (A) LENGTH: 2200 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 174..1466

(xi) SEQUENCE DESCRIPTION: SEQ ID NO: 19:

GTCAACTTTT CTTCCCCTAC TTCCCTGCAT TTCTCCTCTG TGCTCACTGC CACACGCAGC        60

TCAACCTGGA CGGCACAGCC AGATGCGAGA TGCGTCTCTG CTGATCTGAG TCTGCCTGCA       120

GCATGGACCT GGGTCTTCCC TGAAGCATCT CCAGGGCTGG AGGGACGACT GCC ATG         176
                                                             Met
                                                              1

CAC CGA GGG CTC ATC CAT CCG CAG AGC AGG GCA GTG GGA GGA GAC GCC        224
His Arg Gly Leu Ile His Pro Gln Ser Arg Ala Val Gly Gly Asp Ala
         5                  10                  15

ATG ACC CCC ATC GTC ACA GTC CTG ATC TGT CTC GGG CTG AGT CTG GGC        272
```

```
                                                             -continued

Met Thr Pro Ile Val Thr Val Leu Ile Cys Leu Gly Leu Ser Leu Gly
             20                  25                  30

CCC AGG ACC CAC GTG CAG ACA GGG ACC ATC CCC AAG CCC ACC CTG TGG       320
Pro Arg Thr His Val Gln Thr Gly Thr Ile Pro Lys Pro Thr Leu Trp
     35                  40                  45

GCT GAG CCA GAC TCT GTG ATC ACC CAG GGG AGT CCC GTC ACC CTC AGT       368
Ala Glu Pro Asp Ser Val Ile Thr Gln Gly Ser Pro Val Thr Leu Ser
 50                  55                  60                  65

TGT CAG GGG AGC CTT GAA GCC CAG GAG TAC CGT CTA TAT AGG GAG AAA       416
Cys Gln Gly Ser Leu Glu Ala Gln Glu Tyr Arg Leu Tyr Arg Glu Lys
                 70                  75                  80

AAA TCA GCA TCT TGG ATT ACA CGG ATA CGA CCA GAG CTT GTG AAG AAC       464
Lys Ser Ala Ser Trp Ile Thr Arg Ile Arg Pro Glu Leu Val Lys Asn
             85                  90                  95

GGC CAG TTC CAC ATC CCA TCC ATC ACC TGG GAA CAC ACA GGG CGA TAT       512
Gly Gln Phe His Ile Pro Ser Ile Thr Trp Glu His Thr Gly Arg Tyr
         100                 105                 110

GGC TGT CAG TAT TAC AGC CGC GCT CGG TGG TCT GAG CTC AGT GAC CCC       560
Gly Cys Gln Tyr Tyr Ser Arg Ala Arg Trp Ser Glu Leu Ser Asp Pro
     115                 120                 125

CTG GTG CTG GTG ATG ACA GGA GCC TAC CCA AAA CCC ACC CTC TCA GCC       608
Leu Val Leu Val Met Thr Gly Ala Tyr Pro Lys Pro Thr Leu Ser Ala
130                 135                 140                 145

CAG CCC AGC CCT GTG GTG ACC TCA GGA GGA AGG GTG ACC CTC CAG TGT       656
Gln Pro Ser Pro Val Val Thr Ser Gly Gly Arg Val Thr Leu Gln Cys
                150                 155                 160

GAG TCA CAG GTG GCA TTT GGC GGC TTC ATT CTG TGT AAG GAA GGA GAA       704
Glu Ser Gln Val Ala Phe Gly Gly Phe Ile Leu Cys Lys Glu Gly Glu
            165                 170                 175

GAT GAA CAC CCA CAA TGC CTG AAC TCC CAG CCC CAT GCC CGT GGG TCG       752
Asp Glu His Pro Gln Cys Leu Asn Ser Gln Pro His Ala Arg Gly Ser
        180                 185                 190

TCC CGC GCC ATC TTC TCC GTG GGC CCC GTG AGC CCG AAT CGC AGG TGG       800
Ser Arg Ala Ile Phe Ser Val Gly Pro Val Ser Pro Asn Arg Arg Trp
    195                 200                 205

TCG CAC AGG TGC TAT GGT TAT GAC TTG AAC TCT CCC TAT GTG TGG TCT       848
Ser His Arg Cys Tyr Gly Tyr Asp Leu Asn Ser Pro Tyr Val Trp Ser
210                 215                 220                 225

TCA CCC AGT GAT CTC CTG GAG CTC CTG GTC CCA GGT GTT TCT AAG AAG       896
Ser Pro Ser Asp Leu Leu Glu Leu Leu Val Pro Gly Val Ser Lys Lys
                230                 235                 240

CCA TCA CTC TCA GTG CAG CCG GGT CCT GTC GTG GCC CCT GGG GAA AGC       944
Pro Ser Leu Ser Val Gln Pro Gly Pro Val Val Ala Pro Gly Glu Ser
            245                 250                 255

CTG ACC CTC CAG TGT GTC TCT GAT GTC GGC TAT GAC AGA TTT GTT CTG       992
Leu Thr Leu Gln Cys Val Ser Asp Val Gly Tyr Asp Arg Phe Val Leu
        260                 265                 270

TAC AAG GAG GGG GAA CGT GAC CTT CGC CAG CTC CCT GGC CGG CAG CCC      1040
Tyr Lys Glu Gly Glu Arg Asp Leu Arg Gln Leu Pro Gly Arg Gln Pro
    275                 280                 285

CAG GCT GGG CTC TCC CAG GCC AAC TTC ACC CTG GGC CCT GTG AGC CGC      1088
Gln Ala Gly Leu Ser Gln Ala Asn Phe Thr Leu Gly Pro Val Ser Arg
290                 295                 300                 305

TCC TAC GGG GGC CAG TAC AGA TGC TAC GGT GCA TAC AAC CTC TCC TCC      1136
Ser Tyr Gly Gly Gln Tyr Arg Cys Tyr Gly Ala Tyr Asn Leu Ser Ser
                310                 315                 320

GAG TGG TCG GCC CCC AGC GAC CCC CTG GAC ATC CTG ATC ACA GGA CAG      1184
Glu Trp Ser Ala Pro Ser Asp Pro Leu Asp Ile Leu Ile Thr Gly Gln
            325                 330                 335
```

```
ATC CAT GGC ACA CCC TTC ATC TCA GTG CAG CCA GGC CCC ACA GTG GCC    1232
Ile His Gly Thr Pro Phe Ile Ser Val Gln Pro Gly Pro Thr Val Ala
        340                 345                 350

TCA GGA GAG AAC GTG ACC CTG CTG TGT CAG TCA TGG CGG CAG TTC CAC    1280
Ser Gly Glu Asn Val Thr Leu Leu Cys Gln Ser Trp Arg Gln Phe His
    355                 360                 365

ACT TTC CTT CTG ACC AAG GCG GGA GCA GCT GAT GCC CCA CTC CGT CTA    1328
Thr Phe Leu Leu Thr Lys Ala Gly Ala Ala Asp Ala Pro Leu Arg Leu
370                 375                 380                 385

AGA TCA ATA CAC GAA TAT CCT AAG TAC CAG GCT GAA TTC CCC ATG AGT    1376
Arg Ser Ile His Glu Tyr Pro Lys Tyr Gln Ala Glu Phe Pro Met Ser
            390                 395                 400

CCT GTG ACC TCA GCC CAC GCG GGG ACC TAC AGG ACC CTC CAT GGG TTC    1424
Pro Val Thr Ser Ala His Ala Gly Thr Tyr Arg Thr Leu His Gly Phe
        405                 410                 415

CAG CCC CCC ACC CAC CGG TCC CAT CTC CAC ACC TGC AGG CCC            1466
Gln Pro Pro Thr His Arg Ser His Leu His Thr Cys Arg Pro
    420                 425                 430

TGAGGACCAG CCCCTCACCC CCACTGGGTC GGATCCCCAA AGTGGTCTGG GAAGGCACCT    1526

GGGGGTTGTG ATCGGCATCT TGGTGGCCGT CGTCCTACTG CTCCTCCTCC TCCTCCTCCT    1586

CTTCCTCATC CTCCGACATC GACGTCAGGG CAAACACTGG ACATCGACCC AGAGAAAGGC    1646

TGATTTCCAA CATCCTGCAG GGGCTGTGGG GCCAGAGCCC ACAGACAGAG GCCTGCAGTG    1706

GAGGTCCAGC CCAGCTGCCG ACGCCCAGGA AGAAAACCTC TATGCTGCCG TGAAGGACAC    1766

ACAGCCTGAA GATGGGGTGG AGATGGACAC TCGGGCTGCT GCATCTGAAG CCCCCCAGGA    1826

TGTGACCTAC GCCCAGCTGC ACAGCTTGAC CCTCAGACGG AAGGCAACTG AGCCTCCTCC    1886

ATCCCAGGAA AGGGAACCTC CAGCTGAGCC CAGCATCTAC GCCACCCTGG CCATCCACTA    1946

GCCCGGAGGG TACGCAGACT CCACACTCAG TAGAAGGAGA CTCAGGACTG CTGAAGGCAC    2006

GGGAGCTGCC CCCAGTGGAC ACCAATGAAC CCCAGTCAGC CTGGACCCCT AACAAAGACC    2066

ATGAGGAGAT GCTGGGAACT TTGGGACTCA CTTGATTCTG CAGTCGAAAT AACTAATATC    2126

CCTACATTTT TTAATTAAAG CAACAGACTT CTCAATAATC AATGAGTTAA CCGAGAAAAC    2186

TAAAAAAAAA AAAA                                                       2200

(2) INFORMATION FOR SEQ ID NO: 20:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO: 20:

Met His Arg Gly Leu Ile His Pro Gln Ser Arg Ala Val Gly Gly Asp
1               5                   10                  15

Ala Met Thr Pro Ile Val Thr Val Leu Ile Cys Leu Gly Leu Ser Leu
            20                  25                  30

Gly Pro Arg Thr His Val Gln Thr Gly Thr Ile Pro Lys Pro Thr Leu
        35                  40                  45

Trp Ala Glu Pro Asp Ser Val Ile Thr Gln Gly Ser Pro Val Thr Leu
    50                  55                  60

Ser Cys Gln Gly Ser Leu Glu Ala Gln Glu Tyr Arg Leu Tyr Arg Glu
65                  70                  75                  80

Lys Lys Ser Ala Ser Trp Ile Thr Arg Ile Arg Pro Glu Leu Val Lys
                85                  90                  95
```

```
Asn Gly Gln Phe His Ile Pro Ser Ile Thr Trp Glu His Thr Gly Arg
            100                 105                 110

Tyr Gly Cys Gln Tyr Tyr Ser Arg Ala Arg Trp Ser Glu Leu Ser Asp
            115                 120                 125

Pro Leu Val Leu Val Met Thr Gly Ala Tyr Pro Lys Pro Thr Leu Ser
            130                 135                 140

Ala Gln Pro Ser Pro Val Val Thr Ser Gly Gly Arg Val Thr Leu Gln
145                 150                 155                 160

Cys Glu Ser Gln Val Ala Phe Gly Gly Phe Ile Leu Cys Lys Glu Gly
                165                 170                 175

Glu Asp Glu His Pro Gln Cys Leu Asn Ser Gln Pro His Ala Arg Gly
            180                 185                 190

Ser Ser Arg Ala Ile Phe Ser Val Gly Pro Val Ser Pro Asn Arg Arg
            195                 200                 205

Trp Ser His Arg Cys Tyr Gly Tyr Asp Leu Asn Ser Pro Tyr Val Trp
            210                 215                 220

Ser Ser Pro Ser Asp Leu Leu Glu Leu Leu Val Pro Gly Val Ser Lys
225                 230                 235                 240

Lys Pro Ser Leu Ser Val Gln Pro Gly Pro Val Val Ala Pro Gly Glu
                245                 250                 255

Ser Leu Thr Leu Gln Cys Val Ser Asp Val Gly Tyr Asp Arg Phe Val
            260                 265                 270

Leu Tyr Lys Glu Gly Glu Arg Asp Leu Arg Gln Leu Pro Gly Arg Gln
            275                 280                 285

Pro Gln Ala Gly Leu Ser Gln Ala Asn Phe Thr Leu Gly Pro Val Ser
290                 295                 300

Arg Ser Tyr Gly Gly Gln Tyr Arg Cys Tyr Gly Ala Tyr Asn Leu Ser
305                 310                 315                 320

Ser Glu Trp Ser Ala Pro Ser Asp Pro Leu Asp Ile Leu Ile Thr Gly
                325                 330                 335

Gln Ile His Gly Thr Pro Phe Ile Ser Val Gln Pro Gly Pro Thr Val
            340                 345                 350

Ala Ser Gly Glu Asn Val Thr Leu Leu Cys Gln Ser Trp Arg Gln Phe
            355                 360                 365

His Thr Phe Leu Leu Thr Lys Ala Gly Ala Ala Asp Ala Pro Leu Arg
            370                 375                 380

Leu Arg Ser Ile His Glu Tyr Pro Lys Tyr Gln Ala Glu Phe Pro Met
385                 390                 395                 400

Ser Pro Val Thr Ser Ala His Ala Gly Thr Tyr Arg Thr Leu His Gly
                405                 410                 415

Phe Gln Pro Pro Thr His Arg Ser His Leu His Thr Cys Arg Pro
            420                 425                 430
```

(2) INFORMATION FOR SEQ ID NO: 21:

(i) SEQUENCE CHARACTERISTICS:
        (A) LENGTH: 2790 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 177..2132

(ix) FEATURE:
    (A) NAME/KEY: misc_feature
    (B) LOCATION: 1722
    (D) OTHER INFORMATION: /note= "nucleotide 1722 designated C, may be A, C, G, or T"

(xi) SEQUENCE DESCRIPTION: SEQ ID NO: 21:

```
GCCACACGCA GCTCAGCCTG GGCGGCACAG CCAGATGCGA GATGCGTCTC TGCTGATCTG      60

AGTCTGCCTG CAGCATGGAC CTGGGTCTTC CCTGAAGCAT CTCCAGGGCT GGAGGGACGA     120

CTGCCATGCA CCGAGGGCTC ATCCATCCAC AGAGCAGGGC AGTGGGAGGA GACGCC         176

ATG ACC CCC ATC CTC ACG GTC CTG ATC TGT CTC GGG CTG AGT CTG GGC       224
Met Thr Pro Ile Leu Thr Val Leu Ile Cys Leu Gly Leu Ser Leu Gly
 1               5                  10                  15

CCC CGG ACC CAC GTG CAG GCA GGG CAC CTC CCC AAG CCC ACC CTC TGG       272
Pro Arg Thr His Val Gln Ala Gly His Leu Pro Lys Pro Thr Leu Trp
                 20                  25                  30

GCT GAA CCA GGC TCT GTG ATC ACC CAG GGG AGT CCT GTG ACC CTC AGG       320
Ala Glu Pro Gly Ser Val Ile Thr Gln Gly Ser Pro Val Thr Leu Arg
             35                  40                  45

TGT CAG GGG GGC CAG GAG ACC CAG GAG TAC CGT CTA TAT AGA GAA AAG       368
Cys Gln Gly Gly Gln Glu Thr Gln Glu Tyr Arg Leu Tyr Arg Glu Lys
 50                  55                  60

AAA ACA GCA CCC TGG ATT ACA CGG ATC CCA CAG GAG CTT GTG AAG AAG       416
Lys Thr Ala Pro Trp Ile Thr Arg Ile Pro Gln Glu Leu Val Lys Lys
 65                  70                  75                  80

GGC CAG TTC CCC ATC CCA TCC ATC ACC TGG GAA CAT GCA GGG CGG TAT       464
Gly Gln Phe Pro Ile Pro Ser Ile Thr Trp Glu His Ala Gly Arg Tyr
                 85                  90                  95

CGC TGT TAC TAT GGT AGC GAC ACT GCA GGC CGC TCA GAG AGC AGT GAC       512
Arg Cys Tyr Tyr Gly Ser Asp Thr Ala Gly Arg Ser Glu Ser Ser Asp
                100                 105                 110

CCC CTG GAG CTG GTG GTG ACA GGA GCC TAC ATC AAA CCC ACC CTC TCA       560
Pro Leu Glu Leu Val Val Thr Gly Ala Tyr Ile Lys Pro Thr Leu Ser
            115                 120                 125

GCC CAG CCC AGC CCC GTG GTG AAC TCA GGA GGG AAT GTA ACC CTC CAG       608
Ala Gln Pro Ser Pro Val Val Asn Ser Gly Gly Asn Val Thr Leu Gln
130                 135                 140

TGT GAC TCA CAG GTG GCA TTT GAT GGC TTC ATT CTG TGT AAG GAA GGA       656
Cys Asp Ser Gln Val Ala Phe Asp Gly Phe Ile Leu Cys Lys Glu Gly
145                 150                 155                 160

GAA GAT GAA CAC CCA CAA TGC CTG AAC TCC CAG CCC CAT GCC CGT GGG       704
Glu Asp Glu His Pro Gln Cys Leu Asn Ser Gln Pro His Ala Arg Gly
                165                 170                 175

TCG TCC CGC GCC ATC TTC TCC GTG GGC CCC GTG AGC CCG AGT CGC AGG       752
Ser Ser Arg Ala Ile Phe Ser Val Gly Pro Val Ser Pro Ser Arg Arg
                180                 185                 190

TGG TGG TAC AGG TGC TAT GCT TAT GAC TCG AAC TCT CCC TAT GAG TGG       800
Trp Trp Tyr Arg Cys Tyr Ala Tyr Asp Ser Asn Ser Pro Tyr Glu Trp
            195                 200                 205

TCT CTA CCC AGT GAT CTC CTG GAG CTC CTG GTC CTA GGT GTT TCT AAG       848
Ser Leu Pro Ser Asp Leu Leu Glu Leu Leu Val Leu Gly Val Ser Lys
            210                 215                 220

AAG CCA TCA CTC TCA GTG CAG CCA GGT CCT ATC GTG GCC CCT GAG GAG       896
Lys Pro Ser Leu Ser Val Gln Pro Gly Pro Ile Val Ala Pro Glu Glu
225                 230                 235                 240

ACC CTG ACT CTG CAG TGT GGC TCT GAT GCT GGC TAC AAC AGA TTT GTT       944
Thr Leu Thr Leu Gln Cys Gly Ser Asp Ala Gly Tyr Asn Arg Phe Val
                245                 250                 255

CTG TAT AAG GAC GGG GAA CGT GAC TTC CTT CAG CTC GCT GGC GCA CAG       992
```

-continued

```
                Leu Tyr Lys Asp Gly Glu Arg Asp Phe Leu Gln Leu Ala Gly Ala Gln
                            260                 265                 270

CCC CAG GCT GGG CTC TCC CAG GCC AAC TTC ACC CTG GGC CCT GTG AGC                1040
Pro Gln Ala Gly Leu Ser Gln Ala Asn Phe Thr Leu Gly Pro Val Ser
                275                 280                 285

CGC TCC TAC GGG GGC CAG TAC AGA TGC TAC GGT GCA CAC AAC CTC TCC                1088
Arg Ser Tyr Gly Gly Gln Tyr Arg Cys Tyr Gly Ala His Asn Leu Ser
        290                 295                 300

TCC GAG TGG TCG GCC CCC AGC GAC CCC CTG GAC ATC CTG ATC GCA GGA                1136
Ser Glu Trp Ser Ala Pro Ser Asp Pro Leu Asp Ile Leu Ile Ala Gly
305                 310                 315                 320

CAG TTC TAT GAC AGA GTC TCC CTC TCG GTG CAG CCG GGC CCC ACG GTG                1184
Gln Phe Tyr Asp Arg Val Ser Leu Ser Val Gln Pro Gly Pro Thr Val
                325                 330                 335

GCC TCA GGA GAG AAC GTG ACC CTG CTG TGT CAG TCA CAG GGA TGG ATG                1232
Ala Ser Gly Glu Asn Val Thr Leu Leu Cys Gln Ser Gln Gly Trp Met
                340                 345                 350

CAA ACT TTC CTT CTG ACC AAG GAG GGG GCA GCT GAT GAC CCA TGG CGT                1280
Gln Thr Phe Leu Leu Thr Lys Glu Gly Ala Ala Asp Asp Pro Trp Arg
                355                 360                 365

CTA AGA TCA ACG TAC CAA TCT CAA AAA TAC CAG GCT GAA TTC CCC ATG                1328
Leu Arg Ser Thr Tyr Gln Ser Gln Lys Tyr Gln Ala Glu Phe Pro Met
        370                 375                 380

GGT CCT GTG ACC TCA GCC CAT GCG GGG ACC TAC AGG TGC TAC GGC TCA                1376
Gly Pro Val Thr Ser Ala His Ala Gly Thr Tyr Arg Cys Tyr Gly Ser
385                 390                 395                 400

CAG AGC TCC AAA CCC TAC CTG CTG ACT CAC CCC AGT GAC CCC CTG GAG                1424
Gln Ser Ser Lys Pro Tyr Leu Leu Thr His Pro Ser Asp Pro Leu Glu
                405                 410                 415

CTC GTG GTC TCA GGA CCG TCT GGG GGC CCC AGC TCC CCG ACA ACA GGC                1472
Leu Val Val Ser Gly Pro Ser Gly Gly Pro Ser Ser Pro Thr Thr Gly
                420                 425                 430

CCC ACC TCC ACA TCT GGC CCT GAG GAC CAG CCC CTC ACC CCC ACC GGG                1520
Pro Thr Ser Thr Ser Gly Pro Glu Asp Gln Pro Leu Thr Pro Thr Gly
        435                 440                 445

TCG GAT CCC CAG AGT GGT CTG GGA AGG CAC CTG GGG GTT GTG ATC GGC                1568
Ser Asp Pro Gln Ser Gly Leu Gly Arg His Leu Gly Val Val Ile Gly
        450                 455                 460

ATC TTG GTG GCC GTC ATC CTA CTG CTC CTC CTC CTC CTC CTC CTC TTC                1616
Ile Leu Val Ala Val Ile Leu Leu Leu Leu Leu Leu Leu Leu Leu Phe
465                 470                 475                 480

CTC ATC CTC CGA CAT CGA CGT CAG GGC AAA CAC TGG ACA TCG ACC CAG                1664
Leu Ile Leu Arg His Arg Arg Gln Gly Lys His Trp Thr Ser Thr Gln
                485                 490                 495

AGA AAG GCT GAT TTC CAA CAT CCT GCA GGG GCT GTG GGG CCA GAG CCC                1712
Arg Lys Ala Asp Phe Gln His Pro Ala Gly Ala Val Gly Pro Glu Pro
                500                 505                 510

ACA GAC AGA CGC CTG CAG TGG AGG TCC AGC CCA GCT GCC GAT GCC CAG                1760
Thr Asp Arg Arg Leu Gln Trp Arg Ser Ser Pro Ala Ala Asp Ala Gln
        515                 520                 525

GAA GAA AAC CTC TAT GCT GCC GTG AAG CAC ACA CAG CCT GAG GAT GGG                1808
Glu Glu Asn Leu Tyr Ala Ala Val Lys His Thr Gln Pro Glu Asp Gly
                530                 535                 540

GTG GAG ATG GAC ACT CGG CAG AGC CCA CAC GAT GAA GAC CCC CAG GCA                1856
Val Glu Met Asp Thr Arg Gln Ser Pro His Asp Glu Asp Pro Gln Ala
545                 550                 555                 560

GTG ACG TAT GCC GAG GTG AAA CAC TCC AGA CCT AGG AGA GAA ATG GCT                1904
Val Thr Tyr Ala Glu Val Lys His Ser Arg Pro Arg Arg Glu Met Ala
                565                 570                 575
```

-continued

```
TCT CCT CCT TCC CCA CTG TCT GGG GAA TTC CTG GAC ACA AAG GAC AGA      1952
Ser Pro Pro Ser Pro Leu Ser Gly Glu Phe Leu Asp Thr Lys Asp Arg
            580                 585                 590

CAG GCG GAA GAG GAC AGG CAG ATG GAC ACT GAG GCT GCT GCA TCT GAA      2000
Gln Ala Glu Glu Asp Arg Gln Met Asp Thr Glu Ala Ala Ala Ser Glu
                595                 600                 605

GCC CCC CAG GAT GTG ACC TAC GCC CAG CTG CAC AGC TTG ACC CTT AGA      2048
Ala Pro Gln Asp Val Thr Tyr Ala Gln Leu His Ser Leu Thr Leu Arg
        610                 615                 620

CGG AAG GCA ACT GAG CCT CCT CCA TCC CAG GAA GGG CCC TCT CCA GCT      2096
Arg Lys Ala Thr Glu Pro Pro Pro Ser Gln Glu Gly Pro Ser Pro Ala
625                 630                 635                 640

GTG CCC AGC ATC TAC GCC ACT CTG GCC ATC CAC TAG CCCAGGGGGG           2142
Val Pro Ser Ile Tyr Ala Thr Leu Ala Ile His *
                645                 650

GACGCAGACC CCACACTCCA TGGAGTCTGG AATGCATGGG AGCTGCCCCC CCAGTGGACA    2202

CCATTGGACC CCACCCAGCC TGGATCTACC CCAGGAGACT CTGGGAACTT TTAGGGGTCA    2262

CTCAATTCTG CAGTATAAAT AACTAATGTC TCTACAATTT TGAAATAAAG CAACAGACTT    2322

CTCAATAATC AATGAAGTAG CTGAGAAAAC TAAGTCAGAA AGTGCATTAA ACTGAATCAC    2382

AATGTAAATA TTACACATCA AGCGATGAAA CTGGAAAACT ACAAGCCACG AATGAATGAA    2442

TTAGGAAAGA AAAAAGTAG GAAATGAATG ATCTTGGCTT TCCTATAAGA AATTTAGGGC     2502

AGGGCACGGT GGCTCACGCC TGTAATTCCA GCACTTTGGG AGGCCGAGGC GGGCAGATGC    2562

CGAGTTCAGG AGATCGAGAC CATCTTGGCC AACATGGTGA AACCCTGTCT CTCCTAAAAA    2622

TACAAAAATT AGCTGGATGT GGTGGCAGTG CCTGTAATCC CAGCTATTTG GGAGGCTGAG    2682

GCAGGAGAAT CGCTTGAACC AGGGAGTCAG AGGTTTCAGT GAGCCAAGAT CGCACCACTG    2742

CTCTCCAGCC TGGCGACAGA GGGAGACTCC ATCTCAAATT AAAAAAAA                 2790
```

(2) INFORMATION FOR SEQ ID NO: 22:

(i) SEQUENCE CHARACTERISTICS:
        (A) LENGTH: 651 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Thr Pro Ile Leu Thr Val Leu Ile Cys Leu Gly Leu Ser Leu Gly
 1               5                  10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
                100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Thr Leu Gln
```

```
            130                 135                 140
Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
                195                 200                 205

Ser Leu Pro Ser Asp Leu Leu Glu Leu Leu Val Leu Gly Val Ser Lys
            210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
            290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
            370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
                420                 425                 430

Pro Thr Ser Thr Ser Gly Pro Glu Asp Gln Pro Leu Thr Pro Thr Gly
            435                 440                 445

Ser Asp Pro Gln Ser Gly Leu Gly Arg His Leu Gly Val Val Ile Gly
            450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Arg Leu Gln Trp Arg Ser Ser Pro Ala Ala Asp Ala Gln
            515                 520                 525

Glu Glu Asn Leu Tyr Ala Ala Val Lys His Thr Gln Pro Glu Asp Gly
            530                 535                 540

Val Glu Met Asp Thr Arg Gln Ser Pro His Asp Glu Asp Pro Gln Ala
545                 550                 555                 560
```

```
Val Thr Tyr Ala Glu Val Lys His Ser Arg Pro Arg Arg Glu Met Ala
            565                 570                 575

Ser Pro Pro Ser Pro Leu Ser Gly Glu Phe Leu Asp Thr Lys Asp Arg
            580                 585                 590

Gln Ala Glu Glu Asp Arg Gln Met Asp Thr Glu Ala Ala Ala Ser Glu
            595                 600                 605

Ala Pro Gln Asp Val Thr Tyr Ala Gln Leu His Ser Leu Thr Leu Arg
            610                 615                 620

Arg Lys Ala Thr Glu Pro Pro Pro Ser Gln Glu Gly Pro Ser Pro Ala
625                 630                 635                 640

Val Pro Ser Ile Tyr Ala Thr Leu Ala Ile His
            645                 650
```